「12」 United States Patent
Scott et al.

(10) Patent No.: US 10,517,844 B2
(45) Date of Patent: Dec. 31, 2019

(54) INHIBITION OF PROLINE CATABOLISM FOR THE TREATMENT OF CANCER AND OTHER THERAPEUTIC APPLICATIONS

(71) Applicant: Buck Institute for Research on Aging, Novato, CA (US)

(72) Inventors: Gary K. Scott, Berkeley, CA (US); Christopher C. Benz, Novato, CA (US)

(73) Assignee: Buck Institute for Research on Aging, Novato, CA (US)

( * ) Notice: Subject to any disclaimer, the term of this patent is extended or adjusted under 35 U.S.C. 154(b) by 0 days.

(21) Appl. No.: 15/519,504

(22) PCT Filed: Nov. 12, 2015

(86) PCT No.: PCT/US2015/060458
§ 371 (c)(1),
(2) Date: Apr. 14, 2017

(87) PCT Pub. No.: WO2016/077632
PCT Pub. Date: May 19, 2016

(65) Prior Publication Data
US 2017/0348266 A1 Dec. 7, 2017

Related U.S. Application Data

(60) Provisional application No. 62/079,382, filed on Nov. 13, 2014.

(51) Int. Cl.
*A61K 31/198* (2006.01)
*C07C 229/30* (2006.01)
(Continued)

(52) U.S. Cl.
CPC .......... *A61K 31/198* (2013.01); *A61K 45/06* (2013.01); *C07C 229/06* (2013.01);
(Continued)

(58) Field of Classification Search
CPC ... C07C 229/06; C07C 229/20; C07C 229/30; C07C 229/00; A61K 31/198; A61K 45/06
See application file for complete search history.

(56) References Cited

U.S. PATENT DOCUMENTS

2008/0118589 A1* 5/2008 Schneider .............. A61K 36/41
424/773

FOREIGN PATENT DOCUMENTS

WO    WO 2006/130190 A2    12/2006
WO    WO 2016/077632 A2    5/2016

OTHER PUBLICATIONS

Gu et al (Vascular Cell 2013, 5:9, 12 pages) (Year: 2013).*
(Continued)

*Primary Examiner* — Yate' K Cutliff
(74) *Attorney, Agent, or Firm* — Tom Hunter; Weaver Austin Villeneuve & Sampson LLP

(57) ABSTRACT

In various embodiments a cancer treatment method is provided based on inhibition of proline catabolism. When combined with p53 restoration therapy and/or inhibition of glutaminase, the inhibition of proline catabolism results in a "synthetic lethal" and synergistic anticancer response. Novel suicide inhibitors that induce the degradation of proline dehydrogenase (PRODH) are also provided. Also provided is a method of assaying PRODH to identify responders/non-responders to inhibition of proline catabolism and/or glutaminase.

19 Claims, 13 Drawing Sheets

(51) Int. Cl.
| | |
|---|---|
| C07C 229/20 | (2006.01) |
| C07C 229/06 | (2006.01) |
| A61K 45/06 | (2006.01) |
| G01N 33/574 | (2006.01) |
| A61K 31/341 | (2006.01) |
| A61K 31/365 | (2006.01) |
| A61K 31/496 | (2006.01) |
| A61K 31/501 | (2006.01) |
| A61K 31/5377 | (2006.01) |
| A61K 31/713 | (2006.01) |
| C12N 15/113 | (2010.01) |

(52) U.S. Cl.
CPC ......... *C07C 229/20* (2013.01); *C07C 229/30* (2013.01); *G01N 33/57484* (2013.01); *A61K 31/341* (2013.01); *A61K 31/365* (2013.01); *A61K 31/496* (2013.01); *A61K 31/501* (2013.01); *A61K 31/5377* (2013.01); *A61K 31/713* (2013.01); *C12N 15/1137* (2013.01); *C12N 2310/14* (2013.01); *C12N 2320/31* (2013.01); *G01N 33/57415* (2013.01); *G01N 2333/9065* (2013.01); *G01N 2800/52* (2013.01)

(56) References Cited

OTHER PUBLICATIONS

Li et al (J. Biol. Chem. 286(39): 34164-34174, 2011) (Year: 2011).*
Kraus, J.L., et al., The Bioorganic Chemistry of N-Allyl and N-Propargyl substituents in drug interactions with Flavin-linked Oxidases, 1975, Canadian Journal of Chemistry, vol. 53, No. 20, pp. 3141-3144 (Year: 1975).*
Gross, M. I., et al., Anttumor activity of the glutaminase inhibitor CB-839 in triple-negative breast cancer, 2014, Molecular Cancer Therapeutics,13(4), pp. 890-901 (Year: 2014).*
Liu, W., et al., Proline Oxidase promotes tumor cess survival in hypoxic tumor microenvironments, 2012, Cancer Research , 72(14), pp. 3677-3686 (Year: 2012).*
Chemical Abstract Services, Chemical Compund, STN files: Ca, Caplus, Chemcats, Toxcenter, USPATFULL; RN 1592850-54-8, Entered STN: Apr. 29, 2014, 1 page (Year: 2014).*
White, T.A., et al., Structural basis for the inactivation of Themus thermophilus Proline Dehydrogenase by N-Propargylglycine, 2008, Biochemistry, vol. 47, No. 20, pp. 5573-5580 (Year: 2008).*
Yardley, D., Drug resistance and the role of combination chemotherapy in improving patient outcomes, 2013, International Journal of Breast Cancer, vol. 2013, pp. 1-15 (Year: 2013).*
PCT International Search Report and Written Opinion dated Jun. 29, 2016 issued in PCT/US2015/060458.
PCT International Preliminary Report on Patentability dated May 16, 2017 issued in PCT/US2015/060458.
Burmakin, et al. (2013) "Dual targeting of wild-type and mutant p53 by small molecule RITA results in the inhibition of N-Myc and key survival oncogenes and kills neuroblastoma cells in vivo and in vitro." *Clin Cancer Res* 19(18): 5092-5103.
Chemical Abstract compounds, STN express, See RN 1592850-54-8 (Entered STN: Apr. 29, 2014).
Chemical Abstract compounds, STN express, See RN 1693640-63-9 (Entered STN: Apr. 28, 2015), RN 1693594-98-7 (Entered STN: Apr. 28, 2015), and RN 1691004-76-8 (Entered STN: Apr. 24, 2015).
Gross, et al. (2014) "Antitumor activity of the glutaminase inhibitor CB-839 in triple-negative breast cancer," *Molecular Cancer Therapeutics,* 13(4): 890-901.
Hilbert (1995) "Synthesis of Fluorinated Proline Analogs for the Potential Inhibition of Proline Oxidase" *A THESIS—The Honors Program, College of St. Benedict/St. John's University* 29 pages.
Liu, et al. (2012) "Proline dehydrogenase (oxidase), a mitochondrial tumor suppressor, and autophagy under the hypoxia microenvironment." *Autophagy* 8(9): 1407-1409.
Liu, et al. (2012) "Proline oxidase promotes tumor cell survival in hypoxic tumor microenvironments," *Cancer Research,* 72(14): 3677-3686.
Liu, et al. (2012) "Reprogramming of proline and glutamine metabolism contributes to the proliferative and metabolic responses regulated by oncogenic transcription factor c-MYC." *Proc Natl Acad Sci USA* 109: 8983-8988.
Luo, et al. (2012) "Crystal Structures and Kinetics of Monofunctional Proline Dehydrogenase Provide Insight into Substrate Recognition and Conformational Changes Associated with Flavin Reduction and Product Release" *Biochemistry* 51:10099-10108.
O'Quinn, et al. (2002) "Arginine catabolism in lactating porcine mammary tissue." *J Anim Sci* 80:467-474.
Phang, et al. (2012) "The proline regulatory axis and cancer." *Front Oncol* 2:60 (12 pages).
Polyak, et al. (1997) "A model for p53-induced apoptosis." *Nature* 389:300-5.
Possemato, et al. (2011) "Functional genomics reveal that the serine synthesis pathway is essential in breast cancer." *Nature* 476: 346-350 [with Supplementary Information—Total 9 pages].
Ray-Coquard, et al. (2012) "Effect of the MDM2 antagonist RG7112 on the P53 pathway in patients with MDM2-amplified, well-differentiated or dedifferentiated liposarcoma: an exploratory proof-of-mechanism study." *Lancet Oncol* 13:1133-1140.
Saha, et al. (2010) "Pharmacological activation of the p53 pathway in haematological malignancies." *J Clin Pathol* 63:204-209.
Scott, et al. (2015) "A new anticancer strategy based on inhibiting mitochondrial proline dehydrogenase (PRODH) and exploiting synthetic lethal interactions with p53 restoration and/or glutaminase (GLS1) inhibition," *Proceedings: AACR 106th Annual Meeting 2015;* Apr. 18-22, 2015; Philadelphia, PA, Cancer Res 75(15 Suppl) Abstract 5402, 1 page.
Shangary, et al. (2008) "Targeting the MDM2-p53 interaction for cancer therapy." *Clin Cancer Res* 14:5318-5324.
Shangary, et al. (2008) "Temporal activation of p53 by a specific MDM2 inhibitor is selectively toxic to tumors and leads to complete tumor growth inhibition." *Proc Natl Acad Sci* 105: 3933-3938.
TCGA Network (2012) "Comprehensive molecular portraits of human breast tumours." *Nature* 490: 61-70.
Vassilev, et al. (2004) "In vivo activation of the p53 pathway by small-molecule antagonists of MDM2." *Science* 303:844-848.
Wade, et al. (2013) "MDM2, MDMX and p53 in oncogenesis and cancer therapy." *Nature Rev Cancer* 13: 83-96.
Wang, et al. (2011) "Restoring expression of wild-type p53 suppresses tumor growth but does not cause tumor regression in mice with a p53 missense mutation" *The Journal of Clinical Investigation* 21(3): 893-904.
White, et al. (2008) "Structural Basis for the Inactivation of Thermus thermophilus Proline Dehydrogenase by N-Propargylglycine," *Biochemistry,* 47(20): 5573-5580. [NIH Public Access, Author Manuscript, 19pages].
Yau, et al. (2011) "Wildtype p53 upregulation induces contrasting bioenergetics and metabolic responses in malignant and non-malignant mammary epithelial cells." *Amer Assoc Cancer Res* 52: a3797. (PMC Exempt—Conference Proceedings) Abstract—2 pages.
Yau, et al. (2012) "Global metabolomics profiles distinguish malignant from non-malignant human mammary epithelial cell responses to endogenous p53 upregulation by MDM2 antagonism." *Amer Assoc Cancer Res* 53: a5160. (PMC Exempt—Conference Proceedings) Abstract—2 pages.

* cited by examiner

PRODH bound to (S) 5-oxo isomer

5-oxo-tetrahydrofurancarboxylic acid

Pre-reactive PPG in PRODH

Postreactive PPG in PRODH

INHIBITION OF PROLINE CATABOLISM FOR THE TREATMENT OF CANCER AND OTHER THERAPEUTIC APPLICATIONS

CROSS-REFERENCE TO RELATED APPLICATIONS

This application is a U.S. 371 National Phase application of PCT/US2015/060458, filed on Nov. 12, 2015, which claims benefit of and priority to U.S. Ser. No. 62/079,382, filed on Nov. 13, 2014, both of which are incorporated herein by reference for all purposes.

STATEMENT AS TO RIGHTS TO INVENTIONS MADE UNDER FEDERALLY SPONSORED RESEARCH AND DEVELOPMENT

[Not applicable]

BACKGROUND

The tumor suppressor p53 (protein expressed from TP53) has been shown to be downregulated in numerous cancers. The p53 protein exerts its tumor suppressive function acting primarily as a transcription factor, that controls the expression of a large and ever increasing number of target genes in response to a variety of signals (Beckerman and Prives (2010) Cold Spring Harbor Perspectives in Biology 2; Riley et al. (2008) Nat. Rev. Mol. Cell. Biol. 9: 402-412; Brady and Attardi (2010) J. Cell Sci. 123: 2527-2532. Well known outcomes are cell cycle arrest, DNA repair, apoptosis, but more recently p53 involvement in the induction of autophagy and regulation of metabolism and mitochodrial function have also been described (Vousden and Ryan (2009) Nat. Rev. Cancer, 9: 691-700; Gottlieb and Vousden (2010) 53. Regulation of Metabolic Pathways Cold Spring Harbor Perspectives in Biology 2).

The tumor suppressing protein p53 represents an underexplored therapeutic opportunity to develop new treatments with low host toxicity to reverse the abnormal metabolic and bioenergetic programs that are a hallmark feature of cancer. In this regard, mall molecule restoration of p53 function represents a exciting new approach, with the clinical emergence of MDM2 inhibitors like the spiro-oxindole MI-63 and other p53 reactivating drugs especially promising for the treatment of malignancies like breast cancer where up to 75% of all new cases express wildtype (wt) p53.

PIG6, also known as PRODH/POX, is among the apoptotic genes induced by p53 after adriamycin treatment (Polyak et al. (1997) Nature, 389: 300-305.). Since its discovery, evidence has been accumulating on the role that proline dehydrogenase, the protein encoded by the PRODH gene, could play in suppressing tumorigenesis, suggesting its contribution as an apoptosis effector through reactive oxygen species (ROS) induction (Donald et al. (2001) Cancer Res. 61: 1810-1815). Thus, for example, J W Phang's lab (NCI) identified PIG6 as mitochondrial proline oxidase/dehydrogenase (POX/PRODH) whose ROS production was thought to induce apoptosis and mediate tumor suppression.

SUMMARY

It was a surprising discovery that the p53-inducible gene and mitochondrial enzyme, proline dehydrogenase (PRODH), supports breast cancer cell survival by supplying much needed energy and carbon nutrients, especially under nutritional and hypoxic stress conditions, using proline for anaplerotic glutamate production and bypassing glutaminase (GLS1), to fuel oxidative phosphorylation and sustain ATP levels. Our study of MDM2-inhibiting anticancer agents like MI-63 that restore wildtype p53 expression indicates that p53 transcriptional induction of PRODH serves to support breast cancer survival and, by implication, survival of other cancers.

Furthermore, it was discovered that PRODH knockdown, or its enzymatic inhibition by either proline competitive inhibitors like L-THFA and 5-oxo-2-tetrahydrofurancarboxylic acid (5-oxo) or the more potent mechanism-based PRODH "suicide" inhibitor, N-propargylglycine (PPG), not only impairs breast cancer growth by itself, but when combined with either a p53 restoring drug (e.g., MI-63 or nutlin-3a) or a clinical GLS1 inhibitor (e.g. CB-839) produces a "synthetic lethal" and synergistic anticancer response against malignant but not normal breast epithelial cells.

Various embodiments contemplated herein may comprise, but need not be limited to, one or more of the following:

Embodiment 1

A method of treating cancer in a subject, said method comprising treating the subject with a therapy comprising inhibition of proline catabolism.

Embodiment 2

The method of embodiment 1, wherein the therapy comprises a combination therapy additionally comprising: p53 restoration therapy; and/or inhibition of glutaminase (GLS).

Embodiment 3

The method according to any one of embodiments 1-2, wherein the inhibition of proline catabolism comprises inhibition of an enzyme selected from the group consisting of proline dehydrogenase (PRODH), P5C dehydrogenase (PC5DH), glutamate dehydrogenase (GLDH), and any combination thereof.

Embodiment 4

The method of embodiment 3, wherein the inhibition of proline catabolism comprises inhibition of PRODH.

Embodiment 5

The method of embodiment 4, wherein the inhibition of proline catabolism comprises inhibition of PRODH and inhibition of PC5DH.

Embodiment 6

The method of embodiments 4 or 5, wherein the inhibition of PRODH comprises administration to the subject of a molecule that is capable of occupying the proline binding pocket of PRODH and forming a covalent bond with PRODH and/or a flavin adenine dinucleotide (FAD) cofactor of PRODH.

Embodiment 7

The method of embodiment 6, wherein the molecule that is capable of occupying the proline binding pocket of PRODH and forming a covalent bond with PRODH or FAD comprises N-propargylglycine (PPG) or a PPG analog, wherein said analog has the formula:

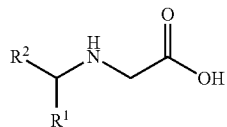

wherein $R^1$ is selected from the group consisting of H, $C_1$-$C_4$ alkyl, halogen, and $C_1$-$C_4$ haloalkyl; $R^2$ is selected from the group consisting of

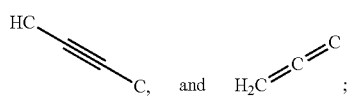

and provided compound is not PPG.

Embodiment 8

The method of embodiment 7, wherein $R^1$ is selected from the group consisting of H, methyl, ethyl, isopropyl, isobutyl, Br, Cl, F, $CF_3$, and $CCl_3$.

Embodiment 9

The method of embodiment 7, wherein $R^1$ is selected from the group consisting of H, methyl, ethyl, isopropyl, and isobutyl.

Embodiment 10

The method according to any one of embodiments 7-9, wherein said analog has the formula:

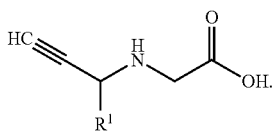

Embodiment 11

The method according to any one of embodiments 7-9, wherein said analog has the formula:

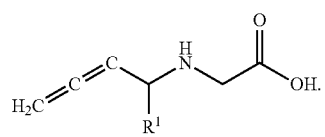

Embodiment 12

The method according to any one of embodiments 7-11, wherein $R^1$ is methyl.

Embodiment 13

The method according to any one of embodiments 7-11, wherein $R^1$ is H.

Embodiment 14

The method according to any one of embodiments 7-13, wherein The method is an S-enantiomer.

Embodiment 15

The method according to any one of embodiments 7-14, wherein the analog induces PRODH degradation.

Embodiment 16

The method according to any one of embodiments 7-15, wherein the analog is an S-enantiomer.

Embodiment 17

The method according to any one of embodiments 6-7, wherein the molecule that is capable of occupying the proline binding pocket of PRODH and forming a covalent bond with PRODH or FAD is an irreversible inhibitor.

Embodiment 18

The method according to any one of embodiments 4-17, wherein the inhibition induces PRODH degradation.

Embodiment 19

The method according to any one of embodiments 4-18, wherein the inhibition of PRODH induces dysfunction and/or degradation of a mitochondrion.

Embodiment 20

The method of embodiments 4 or 5, wherein the inhibition of PRODH comprises administration to the subject of a molecule that is capable of occupying the proline binding pocket of PRODH and forming a hydrogen bond with PRODH at a residue selected from tyrosine 548, arginine 563, arginine 564, and combinations thereof.

Embodiment 21

The method of embodiments 4 or 5, wherein the inhibition of PRODH comprises administration to the subject of a molecule listed in Table 1.

Embodiment 22

The method of embodiments 4 or 5, wherein the inhibition of PRODH comprises administration to the subject of a molecule selected from the group consisting of L-tetrahydro-2-furoic acid (L-THFA), L-4-thiazolidine carboxylic acid, L-3,4-dehydroproline, 4-methylene-L-proline, (E)- and (Z)-4-(fluoromethylene)-L-proline, cis- and trans-5-ethynyl-(+)-proline, cis-5-vinyl-L-proline, trans-5-vinyl-L-proline, cis-4-fluoro-L-proline, trans-4-fluoro-L-proline, 4,4-difluoro-L-proline, 5-fluoro-L-proline, derivatives thereof, and any combination thereof.

Embodiment 23

The method according to any one of embodiments 1-22, wherein the inhibition of proline catabolism comprises antisense therapy or siRNA therapy comprising administration of an antisense nucleic acid or siRNA directed against PRODH, PC5DH, and/or GLDH.

Embodiment 24

The method according to any one of embodiments 2-23, wherein the therapy comprises p53 restoration therapy.

Embodiment 25

The method of embodiment 24, wherein the p53 restoration therapy comprises administration of a p53-activating drug to the subject.

Embodiment 26

The method of embodiment 25, wherein the p53-activating drug comprises a drug selected from the group consisting of a drug that inhibits Mdm2 or Mdmx, a drug that activates p53 directly, a drug that inhibits deacetylation of p53, a drug that inhibits nuclear export of p53, and any combination thereof.

Embodiment 27

The method of embodiment 26, wherein the drug comprises an Mdm2 inhibitor selected from the group consisting of a stapled p53-binding peptide, a nutlin, a benzodiazepinedione, a spiro-oxindole, and any combination thereof.

Embodiment 28

The method of embodiment 27, wherein the Mdm2 inhibitor comprises an inhibitor selected from the group consisting of MI-63, MI-219, MI-888, MI-77301/SAR405838, nutlin-3a, RG7112, RO5963, JNJ-26854165, roscovitine, flavopiridol, DRB, n-phosphonacetyl-1-aspartate PALA), pyrazofurin, actinomycin D, and any combination thereof.

Embodiment 29

The method of embodiment 26, wherein the drug comprises a direct p53 activator selected from the group consisting of CP-31398, PRIMA-1, PhiKan083, RITA, and any combination thereof.

Embodiment 30

The method of embodiment 26, wherein the drug comprises a p53 deacetylation inhibitor selected from the group consisting of sirtinol, suramin, a tenovin, 3,2',3',4'-tetrahydroxychalcone, and any combination thereof.

Embodiment 31

The method of embodiment 26, wherein the drug comprises a drug that inhibits nuclear export of p53 selected from the group consisting of leptomycin B (LMB) derivatives, and any combination thereof.

Embodiment 32

The method of embodiments 2-31, wherein the p53 restoration therapy is selected from the group consisting of gene therapy, antisense therapy, and siRNA therapy.

Embodiment 33

The method according to any one of embodiments 2-32, wherein the therapy comprises inhibition of GLS.

Embodiment 34

The method of embodiment 33, wherein the inhibition of GLS comprises inhibition of GLS1.

Embodiment 35

The method of embodiment 34, wherein the inhibition of GLS1 comprises administration to the subject of a molecule selected from CB-839/Calithera, 968, BPTES, or DON.

Embodiment 36

The method or formulation of embodiment 33, wherein the inhibition of GLS comprises antisense therapy or siRNA therapy.

Embodiment 37

The method of embodiment 1, wherein the therapy comprises administering to said subject an effective amount of a formulation according to embodiment 70 or 77.

Embodiment 38

The method according to any one of embodiments 1-37, wherein the cancer comprises a cancer that contains detectable PRODH.

Embodiment 39

The method according to any one of embodiments 1-38, wherein the cancer comprises a cancer known to be amenable to p53 restoration therapy.

Embodiment 40

The method according to any one of embodiments 1-38, wherein the cancer comprises cells having at least one functional p53 allele.

Embodiment 41

The method according to any one of embodiments 1-38, wherein the cancer comprises cells having no functional p53 alleles.

Embodiment 42

The method according to any one of embodiments 1-41, wherein the cancer comprises a cancer known to be amenable to inhibition of glutaminase (GLS).

Embodiment 43

The method according to any one of embodiments 1-42, wherein the cancer comprises cells subject to hypoxic conditions.

Embodiment 44

The method according to any one of embodiments 1-43, wherein the cancer comprises a solid tumor.

Embodiment 45

The method according to any one of embodiments 1-43, wherein the cancer comprise cancer stem cells.

Embodiment 46

The method according to any one of embodiments 1-45, wherein said cancer comprises a cancer selected from the group consisting of breast cancer, prostate cancer, colon cancer, cervical cancer, ovarian cancer, pancreatic cancer, renal cell (kidney) cancer, glioblastoma, acute lymphoblastic leukemia (ALL), acute myeloid leukemia (AML), Adrenocortical carcinoma, AIDS-related cancers (e.g., kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, bronchial tumors, burkitt lymphoma, carcinoid tumors (e.g., childhood, gastrointestinal), cardiac tumors, chordoma, chronic lymphocytic leukemia (CLL), chronic myelogenous leukemia (CML), chronic myeloproliferative disorders, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CML), multiple myeloma, nasal cavity and paranasal sinus cancer, nasopharyngeal cancer, neuroblastoma, oral cavity cancer, lip and oropharyngeal cancer, osteosarcoma, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, nonmelanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

Embodiment 47

The method according to any one of embodiments 1-45, wherein the cancer comprises breast cancer.

Embodiment 48

The method according to any one of embodiments 1-47, wherein the subject comprises a mammal.

Embodiment 49

The method of embodiment 48, wherein the subject comprises a human.

Embodiment 50

The method of embodiment 48, wherein the subject comprises a non-human mammal.

Embodiment 51

The method according to any one of embodiments 2-50, wherein the combination therapy produces a synergistic effect.

Embodiment 52

The method according to any one of embodiments 2-50, wherein the combination therapy produces a synthetic lethal effect.

Embodiment 53

The method according to any one of embodiments 2-52, wherein the combination therapy permits the use of a lower dose of one or more drug(s) than the effective amount of that drug when administered alone.

Embodiment 54

The method according to any one of embodiments 1-53, wherein said method further comprises administering an anti-angiogenesis drug to said subject.

Embodiment 55

The method of embodiment 54, wherein said anti-angiogenesis drug comprises a drug selected from the group consisting of bevacizumab, aflibercept, ramucirumab, axtinib, cabozantinib, everolimus, pazopanib, regorafanib, sorafenib, suntinib, and vendatanib.

Embodiment 56

The method according to any one of embodiments 1-55, wherein said method further comprises determining the PRODH expression level in said cancer and administering said method to subjects whose cancer shows elevated PRODH levels.

Embodiment 57

The method according to any one of embodiments 1-56, wherein said method further comprises determining the level of hypoxia of cells comprising said cancer and administering said method to subjects whose cancer comprises hypoxic cells.

Embodiment 58

An analog of N-propargylglycine (PPG) that is capable of occupying the proline binding pocket of proline dehydrogenase (PRODH) and forming a covalent bond with PRODH or a flavin adenine dinucleotide (FAD) cofactor of PRODH, wherein the PPG analog has the formula:

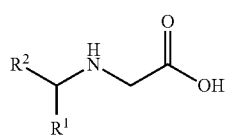

wherein $R^1$ is selected from the group consisting of H, $C_1$-$C_4$ alkyl, halogen, and $C_1$-$C_4$ haloalkyl; $R^2$ is selected from the group consisting of

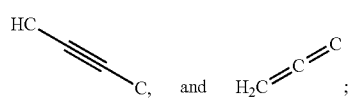

and provided the PPG analog is not PPG.

Embodiment 59

The PPG analog of embodiment 58, wherein $R^1$ is selected from the group consisting of H, methyl, ethyl, isopropyl, isobutyl, Br, Cl, F, $CF_3$, and $CCl_3$.

Embodiment 60

The PPG analog of embodiment 58, wherein $R^1$ is selected from the group consisting of H, methyl, ethyl, isopropyl, and isobutyl.

Embodiment 61

The PPG analog according to any one of embodiments 58-60, wherein said analog has the formula

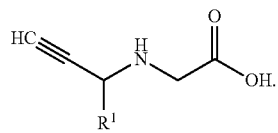

Embodiment 62

The PPG analog according to any one of embodiments 58-60, wherein said analog has the formula:

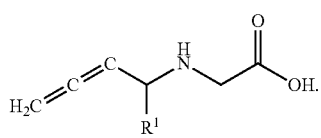

Embodiment 63

The PPG analog according to any one of embodiments 58-62, wherein $R^1$ is methyl.

Embodiment 64

The PPG analog according to any one of embodiments 58-62, wherein $R^1$ is H.

Embodiment 65

The PPG analog according to any one of embodiments 58-64, wherein the PPG analog is an S-enantiomer.

Embodiment 66

The PPG analog according to any one of embodiments 58-65, wherein the analog is capable of occupying the proline binding pocket of PRODH and forming a covalent bond with PRODH or FAD and is an irreversible inhibitor.

Embodiment 67

The PPG analog according to any one of embodiments 58-66, wherein the analog induces PRODH degradation.

Embodiment 68

The PPG analog according to any one of embodiments 58-67, wherein the analog induces degradation of a mitochondrion.

Embodiment 69

The PPG analog according to any one of embodiments 58-68, wherein the PPG analog is an S-enantiomer.

Embodiment 70

A pharmaceutical formulation comprising the PPG analog according to any one of embodiments 58-69 in a pharmaceutically acceptable carrier.

Embodiment 71

The pharmaceutical formulation of embodiments 70, wherein said formulation is a unit dosage formulation.

Embodiment 72

The pharmaceutical formulation according to any one of embodiments 70-71, wherein said formulation is formulated for administration via a route selected from the group consisting of oral administration, transdermal administration, parenteral administration, aerosol administration, administration via inhalation, intravenous or intra-arterial administration, local administration via injection or cannula, and rectal administration.

Embodiment 73

The pharmaceutical formulation according to any one of embodiments 70-71, wherein said formulation is formulated for oral administration.

Embodiment 74

The pharmaceutical formulation according to any one of embodiments 70-71, wherein said formulation is formulated for administration into or near a solid tumor.

Embodiment 75

The pharmaceutical formulation according to any one of embodiments 70-74, wherein said formulation further comprises a drug that promotes p53 restoration.

Embodiment 76

The pharmaceutical formulation according to any one of embodiments 70-75, wherein said formulation further comprises a drug that inhibits glutaminase (GLS).

Embodiment 77

A pharmaceutical formulation comprising: a drug that inhibits proline catabolism; and a drug that promotes p53 restoration; and/or a drug that inhibits glutaminase (GLS).

Embodiment 78

The pharmaceutical formulation of embodiment 76, wherein said drug that inhibits proline catabolism comprises N-propargylglycine (PPG) or a PPG analog according to any one of embodiments 58-69.

Embodiment 79

The pharmaceutical formulation of embodiment 78, wherein said drug that inhibits proline catabolism comprises PPG.

Embodiment 80

The pharmaceutical formulation of embodiment 78, wherein said drug that inhibits proline catabolism comprises a PPG analog according to any one of embodiments 58-69.

Embodiment 81

The pharmaceutical formulation of embodiment 76, wherein said drug that inhibits proline catabolism comprises a compound in Table 1.

Embodiment 82

The pharmaceutical formulation of embodiment 76, wherein said drug that inhibits proline catabolism comprises a molecule selected from the group consisting of L-tetrahydro-2-furoic acid (L-THFA), L-4-thiazolidine carboxylic acid, L-3,4-dehydroproline, 4-methylene-L-proline, (E)- and (Z)-4-(fluoromethylene)-L-proline, cis- and trans-5-ethynyl-(+)-proline, cis-5-vinyl-L-proline, trans-5-vinyl-L-proline, cis-4-fluoro-L-proline, trans-4-fluoro-L-proline, 4,4-difluoro-L-proline, 5-fluoro-L-proline, derivatives thereof, and any combination thereof.

Embodiment 83

The pharmaceutical formulation of embodiment 76, wherein said drug that inhibits proline catabolism comprises an siRNA directed against PRODH, PC5DH, and/or GLDH.

Embodiment 84

The pharmaceutical formulation according to any one of embodiments 76-83, wherein said formulation comprises a drug that promotes p53 restoration.

Embodiment 85

The pharmaceutical formulation of embodiment 84, wherein said drug that promotes p53 restoration comprises a p53-activating drug.

Embodiment 86

The pharmaceutical formulation of embodiment 85, wherein the p53-activating drug comprises a drug selected from the group consisting of a drug that inhibits Mdm2 or Mdmx, a drug that activates p53 directly, a drug that inhibits deacetylation of p53, a drug that inhibits nuclear export of p53, and any combination thereof.

Embodiment 87

The pharmaceutical formulation of embodiment 86, wherein the p53-activating drug comprises an Mdm2 inhibitor selected from the group consisting of a stapled p53-binding peptide, a nutlin, a benzodiazepinedione, a spirooxindole, and any combination thereof.

Embodiment 88

The pharmaceutical formulation of embodiment 87, wherein the Mdm2 inhibitor comprises an inhibitor selected from the group consisting of MI-63, MI-219, MI-888, MI-77301/SAR405838, nutlin-3a, RG7112, Ro5963, JNJ-26854165, roscovitine, flavopiridol, DRB, n-phosphonacetyl-1-aspartate PALA), pyrazofurin, actinomycin D, and any combination thereof.

Embodiment 89

The pharmaceutical formulation of embodiment 84, wherein the drug that promotes p53 restoration comprises a direct p53 activator selected from the group consisting of CP-31398, PRIMA-1, PhiKan083, RITA, and any combination thereof.

Embodiment 90

The pharmaceutical formulation of embodiment 84, wherein the drug that promotes p53 restoration comprises a p53 deacetylation inhibitor selected from the group consisting of sirtinol, suramin, a tenovin, 3,2',3',4'-tetrahydroxychalcone, and any combination thereof.

Embodiment 91

The pharmaceutical formulation of embodiment 84, wherein the drug that promotes p53 restoration comprises a drug that inhibits nuclear export of p53 selected from the group consisting of leptomycin B (LMB) derivatives and any combination thereof.

Embodiment 92

The pharmaceutical formulation according to any one of embodiments 76-91, wherein said formulation comprises a drug that inhibits glutaminase (GLS).

Embodiment 93

The method or formulation of embodiment 92, wherein the drug that inhibits GLS is an inhibitor of GLS1.

Embodiment 94

The method or formulation of embodiment 93, wherein the inhibitor of GLS1 comprises a molecule selected from the group consisting of CB-839/Calithera, 968, BPTES, and DON.

Embodiment 95

The method or formulation of embodiment 92, wherein the inhibitor of GLS comprises an siRNA that inhibits GLS.

Embodiment 96

The pharmaceutical formulation according to any one of embodiments 76-95, wherein said formulation is a unit dosage formulation.

Embodiment 97

The pharmaceutical formulation according to any one of embodiments 76-96, wherein said formulation is formulated for administration via a route selected from the group consisting of oral administration, transdermal administration, parenteral administration, aerosol administration, administration via inhalation, intravenous or intra-arterial administration, local administration via injection or cannula, and rectal administration.

Embodiment 98

The pharmaceutical formulation according to any one of embodiments 76-96, wherein said formulation is formulated for oral administration.

Embodiment 99

The pharmaceutical formulation according to any one of embodiments 76-96, wherein said formulation is formulated for administration into or near a solid tumor.

Embodiment 100

A method for determining whether a subject with cancer is a candidate for a cancer treatment method comprising inhibition of proline catabolism or inhibition of glutaminase (GSL), the method comprising:
(a) assaying a sample of the cancer for proline dehydrogenase (PRODH) level; and
(b) if PRODH is elevated relative to a normal level, identifying the subject as one who is a candidate for a cancer treatment method comprising inhibition of proline catabolism and/or as one who is likely to have a reduced response to a cancer treatment method consisting of inhibition of GLS1 alone; and (c) if PRODH is not elevated relative to a normal level, identifying the subject as one who is a candidate for a cancer treatment method comprising inhibition of GLS.

Embodiment 101

The method of embodiment 100, wherein the method additionally comprises assaying the sample for one or more of: P5C dehydrogenase (PC5DH), glutamate dehydrogenase (GLDH), and P5C reductase-1 (PYCR1).

Embodiment 102

The method of embodiment 100, wherein if PRODH is elevated relative to a normal level, the method comprises identifying the subject as one who is a candidate for the treatment method according to any one of embodiments 1-57.

Embodiment 103

The method of embodiment 100, wherein if PRODH is elevated relative to a normal level, the method further comprises treating the subject according to the treatment method according of any one of embodiments 1-57.

Embodiment 104

The method of embodiment 100, wherein the method additionally comprises testing a sample of the cancer to determine whether cancer cells comprise at least one functional p53 allele.

Embodiment 105

The method of embodiment 104, wherein if the cancer cells are determined to comprise at least one functional p53 allele, the method comprises identifying the subject as one who is a candidate for the treatment method of embodiments 2-57.

Embodiment 106

The method of embodiment 104, wherein if the cancer cells are determined to comprise at least one functional p53 allele, the method comprises treating said subject using a treatment method according to any one of embodiments 2-57.

Embodiment 107

The method of embodiment 104, wherein if the cancer cells are determined to comprise no functional p53 alleles, the treatment method comprises identifying the subject as one who is a candidate for the method of embodiments 24-57.

Embodiment 108

The method of embodiment 104, wherein if the cancer cells are determined to comprise no functional p53 alleles, the treatment method comprises treating said subject using a treatment method according to any one of embodiments 24-57.

Embodiment 109

The method of embodiment 100, wherein the method additionally comprises assaying the sample for GLS level; and if GLS is elevated relative to a normal level, identifying the subject as one who is a candidate for a cancer treatment method comprising inhibition of GLS and/or as one who is likely to have a reduced response to a cancer therapy consisting of inhibition of proline catabolism alone; and if GLS is not elevated relative to a normal level, identifying the subject as one who is a candidate for a cancer treatment method comprising inhibition of proline catabolism.

Embodiment 110

The method of embodiment 109, wherein the GLS level comprises a GLS1 level.

Embodiment 111

The method of embodiments 109 or 110, wherein the GLS level comprises a GLS2 level.

Embodiment 112

The method of embodiments 100-111 wherein the PRODH level comprises a PRODH protein level assayed by immunohistochemistry.

Embodiment 113

The method of embodiments 101-112, wherein the method comprises additionally assaying the sample for one or more of GLS, P5C dehydrogenase (PC5DH), glutamate dehydrogenase (GLDH), and P5C reductase-1 (PYCR1), wherein said additional assay comprises an immunohistochemistry assay.

Embodiment 114

A method comprising:
(a) assaying a sample of cancer obtained from a subject for proline dehydrogenase (PRODH) level; and
(b) if, based on said PRODH assay, the PRODH level is elevated relative to a normal level, treating the subject with a drug that inhibits proline catabolism.

Embodiment 115

The method of embodiment 114, wherein if PRODH is elevated relative to a normal level, the method comprises treating the subject according to the treatment method of embodiments 1-57.

Embodiment 116

The method of embodiment 114, wherein the method comprises additionally testing a sample of the cancer to determine whether cancer cells comprise at least one functional p53 allele.

Embodiment 117

The method of embodiment 116, wherein if the cancer cells are determined to comprise at least one functional p53 allele, the method comprises identifying the subject as one who is a candidate for the treatment method of embodiments 2-57.

Embodiment 118

The method of embodiment 116, wherein if the cancer cells are determined to comprise at least one functional p53 allele, the method comprises treating said subject using a treatment method according to any one of embodiments 2-57.

Embodiment 119

The method of embodiment 116, wherein if the cancer cells are determined to comprise no functional p53 alleles, the treatment method comprises identifying the subject as one who is a candidate for the method of embodiments 24-57.

Embodiment 120

The method of embodiment 116, wherein if the cancer cells are determined to comprise no functional p53 alleles, the treatment method comprises treating said subject using a treatment method according to any one of embodiments 24-57.

Embodiment 121

The method of embodiment 114, wherein the method comprises additionally assaying the sample for GLS level; and if, based on said GLS assay, the GLS level is elevated relative to a normal level, treating the subject with a drug that inhibits GLS.

Embodiment 122

The method of embodiment 121, wherein if the GLS is elevated relative to a normal level, the method comprises treating the subject according to the treatment method of embodiments 33-57.

Embodiment 123

The method of embodiment 122, wherein the GLS level comprises a GLS1 level.

Embodiment 124

The method of embodiments 122 or 123, wherein the GLS level comprises a GLS2 level.

Embodiment 125

The method of embodiments 114-124, wherein the PRODH level comprises a PRODH protein level assayed by immunohistochemistry.

Embodiment 126

The method of embodiment 121-125, wherein the GLS comprises a GLS protein level assayed by immunohistochemistry.

Embodiment 127

A method of improving a measure of lifespan and/or healthspan, and/or improving physiological stress response in a subject, said method comprising treating the subject with a therapy comprising administration of an irreversible inhibitor of PRODH.

Embodiment 128

The method embodiment 127, wherein the inhibition of PRODH comprises administration to the subject of a molecule that is capable of occupying the proline binding pocket of PRODH and forming a covalent bond with PRODH and/or a flavin adenine dinucleotide (FAD) cofactor of PRODH.

Embodiment 129

The method of embodiment 128, wherein the molecule that is capable of occupying the proline binding pocket of PRODH and forming a covalent bond with PRODH or FAD comprises N-propargylglycine (PPG) or a PPG analog according to any one of embodiments 58-69.

Embodiment 130

The method of embodiment 129, wherein the irreversible inhibitor induces PRODH degradation.

Embodiment 131

The method of embodiment 127, wherein the inhibition of PRODH comprises administration to the subject of a molecule that is capable of occupying the proline binding pocket of PRODH and forming a hydrogen bond with PRODH at a residue selected from tyrosine 548, arginine 563, arginine 564, and combinations thereof.

Embodiment 132

The method of embodiment 127, wherein the inhibition of PRODH comprises administration to the subject of a molecule listed in Table 1.

Embodiment 133

The method of embodiment 127, wherein the inhibition of PRODH comprises administration to the subject of a molecule selected from the group consisting of L-tetrahydro-2-furoic acid (L-THFA), L-4-thiazolidine carboxylic acid, L-3,4-dehydroproline, 4-methylene-L-proline, (E)- and (Z)-4-(fluoromethylene)-L-proline, cis- and trans-5-ethynyl-(+)-proline, cis-5-vinyl-L-proline, trans-5-vinyl-L-proline, cis-4-fluoro-L-proline, trans-4-fluoro-L-proline, 4,4-difluoro-L-proline, 5-fluoro-L-proline, derivatives thereof, and any combination thereof.

Embodiment 134

The method of embodiment 127, wherein the inhibition of proline catabolism comprises antisense therapy or siRNA therapy comprising administration of an antisense nucleic acid or siRNA directed against PRODH.

Embodiment 135

The method according to any one of embodiments 127-134, wherein said method comprises improving a measure of lifespan and/or healthspan of said subject.

Embodiment 136

The method of embodiment 135, wherein the improved measure of life span and/or health span comprises a reduction in frailty, an improvement in function in an age-related disability, the mitigation of a symptom of an age-related disease, and/or a delay in onset of frailty, age-related disability, or age-related disease, relative to the condition of the subject before administration of PRODH inhibition therapy or relative to a control population.

Embodiment 137

The method of embodiment 136, wherein the reduction in frailty comprises an improvement in a measure selected from the group consisting of increased strength, weight gain, faster mobility, increased energy, increased levels of activity, increased endurance, and enhanced behavioral response to a sensory cue, wherein the reduction is relative to the condition of the subject before administration of PRODH inhibition therapy or relative to a control population.

Embodiment 138

The method of embodiment 136, wherein the reduction in frailty comprises an improvement in a measure selected from the group consisting of a decrease in one or more inflammatory biomarkers, an improvement in glucose homeostasis, and a decrease in one of more biomarkers of clotting activation.

Embodiment 139

The method of embodiment 136 wherein the age-related disease is selected from the group consisting of osteoporosis, arthritis, cataracts, macular degeneration, and cardiovascular disease.

Embodiment 140

The method of embodiment 135, wherein the improved measure of life span and/or health span comprises an improvement in one or more parameters selected from the group consisting of cholesterol level, triglyceride level, high density lipoprotein level, and blood pressure.

Embodiment 141

The method of embodiment 135, wherein the improved measure of life span and/or health span comprises a reduction in, a reversal of, or delay in onset of sarcopenia, relative to the condition of the subject before administration PRODH inhibition therapy or relative to a control population.

Embodiment 142

The method of embodiment 135, wherein the improved measure of life span and/or health span comprises a reduction in, a reversal of, or delay in onset of an age-related increase in lipofuscin accumulation in one or more tissues selected from the group consisting of brain, heart, liver, spleen, and kidney, relative to the condition of the subject before administration PRODH inhibition therapy or relative to a control population.

Embodiment 143

The method according to any one of embodiments 127-142, wherein the subject is suffering from, or determined to be at risk for, frailty, an age-related disability, or an age-related disease.

Embodiment 144

The method of embodiment 143, wherein the subject is suffering from, or determined to be at risk for, frailty.

Embodiment 145

The method of embodiment 144, wherein the subject is determined to have at least three symptoms selected from the group consisting of weakness, weight loss, slowed mobility, fatigue, low levels of activity, poor endurance, and impaired behavioral response to a sensory cue.

Embodiment 146

The method of embodiment 144, wherein the subject is determined to have one or more symptoms selected from the group consisting of an increase in one or more inflammatory biomarkers, glucose homeostasis impairment, and an increase in one of more biomarkers of clotting activation.

Embodiment 147

The method of embodiment 143, wherein the subject is suffering from sarcopenia.

Embodiment 148

The method of embodiment 143, wherein the subject has lipofuscin accumulation in one or more tissues selected from the group consisting of brain, heart, liver, spleen, and kidney.

Embodiment 149

The method of embodiment 135, wherein the improvement in a measure of life span and/or health span comprises an enhanced ability to maintain homeostasis during the application of a stressor and/or a reduced time required to return to homeostasis after the application of a stressor.

Embodiment 150

The method of embodiment 149, wherein the stressor is selected from drug-induced oxidative stress, exposure to heat, and exposure to cold.

Embodiment 151

The method of embodiment 149, wherein the subject has been determined to have a reduced ability to maintain homeostasis during the application of a stressor and/or an extended time required to return to homeostasis after the application of a stressor, wherein the reduced ability or extended time is relative to the condition of the subject at a previous time or relative to a normal ability or time.

Embodiment 152

The method of embodiment 135, wherein the measure of life span and/or health span comprises the level and/or activity of a molecule that plays a role in protein trafficking, the autophagy pathway, ubiquitination, and/or lysozomal degradation of proteins.

Embodiment 153

The method of embodiment 152, wherein the molecule comprises lysosome-associated membrane protein-2 (LAMP-2).

Embodiment 154

The method of embodiment 135, wherein the measure of life span and/or health span comprises the number of inclusion bodies in muscle tissue.

Embodiment 155

The method of embodiment 135, wherein the measure of life span and/or health span comprises mitochondrial function and/or morphology.

Embodiment 156

The method according to any one of embodiments 135-155, wherein the subject has been determined to have an abnormal level and/or activity of a molecule that plays a role in protein trafficking, the autophagy pathway, ubiquitination, and/or lysozomal degradation of proteins.

Embodiment 157

The method of embodiment 156, wherein the molecule comprises lysosome-associated membrane protein-2 (LAMP-2).

Embodiment 158

The method according to any one of embodiments 135-157, wherein the subject has been determined to have abnormal inclusion bodies in muscle tissue; and/or the subject has been determined to have an abnormality in mitochondrial function and/or morphology.

Embodiment 159

The method according to any one of embodiments 127-134, wherein said method comprises reducing the physiological stress.

Embodiment 160

The method of embodiment 135, wherein said improvement in physiological stress response comprises improving one or more measures of physiological stress response selected from the group consisting of respiratory levels, blood pressure, cardiac rate and output levels, cortisol level, cortisol/DHEA ratio, Th1 immunity activity (NK cells, killer T cells), catecholamine levels, chromogranin A levels, free radicals or reactive oxygen species, N-acetylaspartate levels, and expression of heat shock proteins relative to the condition of the subject before administration PRODH inhibition therapy or relative to a control population.

Embodiment 161

The method according to any one of embodiments 127-160, wherein the improvement in the measure of life span and/or health span and/or physiological stress response is at least about 40 percent, relative to the condition of the subject before administration PRODH inhibition therapy or relative to a control population.

Embodiment 162

The method of embodiment 161, wherein the improvement is at least about 50%.

Embodiment 163

The method of embodiment 162, wherein the improvement is at least about 60%.

Embodiment 164

The method according to any one of embodiments 127-163, further comprising administering to said subject, an effective amount of an additional agent that is useful for increasing a measure of life span and/or health span.

Embodiment 165

The method of embodiment 164, wherein said additional agent is selected from the group consisting of a compound selected from the group consisting of an antioxidant, rapamycin, metformin, valproic acid, ethosuximide, trimethadione, 3,3-diethyl-2-pyrrolidinone, lithium, resveratrol, and derivatives thereof.

Embodiment 166

The method according to any one of embodiments 127-165, wherein the subject comprises a mammal.

Embodiment 167

The method of embodiment 166, wherein the subject comprises a human.

Embodiment 168

The method of embodiment 166, wherein the subject comprises a non-human mammal.

Embodiment 169

A method of treating cancer in a subject, the method comprising treating the subject with a therapy comprising inhibition of proline catabolism.

Embodiment 170

The method of embodiment 169, wherein the therapy comprises a combination therapy additionally comprising: p53 restoration therapy; and/or inhibition of glutaminase (GLS).

Embodiment 171

A pharmaceutical formulation comprising: a drug that inhibits proline catabolism; and a drug that promotes p53 restoration; and/or a drug that inhibits glutaminase (GLS).

Embodiment 172

The method or formulation of any preceding embodiment, wherein the inhibition of proline catabolism comprises inhibition of an enzyme selected from the group consisting of proline dehydrogenase (PRODH), P5C dehydrogenase (PC5DH), glutamate dehydrogenase (GLDH), and any combination thereof.

Embodiment 173

The method or formulation of embodiment 172, wherein the inhibition of proline catabolism comprises inhibition of PRODH.

Embodiment 174

The method or formulation of embodiment 173, wherein the inhibition of proline catabolism comprises inhibition of PRODH and inhibition of PC5DH.

Embodiment 175

The method or formulation of embodiments 173 or 174, wherein the inhibition of PRODH comprises administration to the subject of a molecule that is capable of occupying the proline binding pocket of PRODH and forming a covalent bond with PRODH or a flavin adenine dinucleotide (FAD) cofactor of PRODH.

Embodiment 176

The method or formulation of embodiment 175, wherein the molecule that is capable of occupying the proline binding pocket of PRODH and forming a covalent bond with PRODH or FAD comprises N-propargylglycine (PPG) or an analog thereof, wherein the PPG analog has the formula:

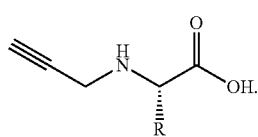

Embodiment 177

The method or formulation of embodiment 176, wherein R is selected from the group consisting of: methyl, isopropyl, and isobutyl.

Embodiment 178

The method or formulation of embodiments 175 or 176, wherein the PPG analog is an S-enantiomer.

Embodiment 179

The method or formulation of embodiments 175-178, wherein the molecule that is capable of occupying the proline binding pocket of PRODH and forming a covalent bond with PRODH or FAD is an irreversible inhibitor.

Embodiment 180

The method or formulation of embodiment 179, wherein the irreversible inhibitor induces PRODH degradation.

Embodiment 181

The method or formulation of embodiments 175-180, wherein the PPG analog is produced by the synthetic scheme:

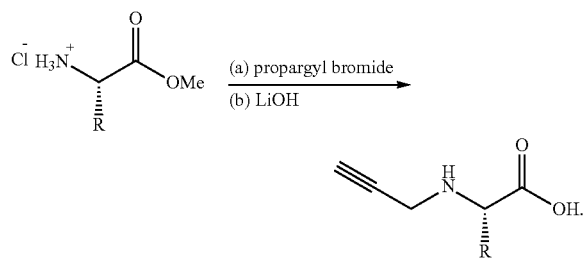

Embodiment 182

The method or formulation of embodiments 173 or 174, wherein the inhibition of PRODH comprises administration to the subject of a molecule that is capable of occupying the proline binding pocket of PRODH and forming a hydrogen bond with PRODH at a residue selected from tyrosine 548, arginine 563, arginine 564, and combinations thereof.

Embodiment 183

The method or formulation of embodiment 182, wherein the molecule that is capable of occupying the proline binding pocket of PRODH and forming a hydrogen bond with PRODH comprises (S)-5-oxo-tetrahydrofuran carboxylic acid.

Embodiment 184

The method or formulation of embodiments 173 or 174, wherein the inhibition of PRODH comprises administration to the subject of a molecule selected from the group consisting of L-tetrahydro-2-furoic acid (L-THFA), L-4-thiazolidine carboxylic acid, L-3,4-dehydroproline, 4-methylene-L-proline, (E)- and (Z)-4-(fluoromethylene)-L-proline, cis- and trans-5-ethynyl-(+)-proline, cis-5-vinyl-L-proline, trans-5-vinyl-L-proline, cis-4-fluoro-L-proline, trans-4-fluoro-L-proline, 4,4-difluoro-L-proline, 5-fluoro-L-proline, derivatives thereof, and any combination thereof.

Embodiment 185

The method or formulation of embodiments 172-184, wherein the inhibition of proline catabolism comprises antisense therapy or siRNA therapy comprising administration of an antisense nucleic acid or siRNA directed against PRODH, PC5DH, and/or GLDH.

Embodiment 186

The method or formulation of embodiments 170-185, wherein the therapy comprises p53 restoration therapy, or the formulation comprises a drug that promotes p53 restoration.

Embodiment 187

The method or formulation of embodiments 170-186, wherein the p53 restoration therapy comprises administration of a p53-activating drug to the subject, or wherein the drug that promotes p53 restoration comprises a p53-activating drug.

Embodiment 188

The method or formulation of embodiment 187, wherein the p53-activating drug comprises a drug selected from the group consisting of a drug that inhibits Mdm2 or Mdmx, a drug that activates p53 directly, a drug that inhibits deacetylation of p53, a drug that inhibits nuclear export of p53, and any combination thereof.

Embodiment 189

The method or formulation of embodiment 188, wherein the drug comprises an Mdm2 inhibitor selected from the group consisting of a stapled p53-binding peptide, a nutlin, a benzodiazepinedione, a spiro-oxindole, and any combination thereof.

Embodiment 190

The method or formulation of embodiment 189, wherein the Mdm2 inhibitor comprises an inhibitor selected from the group consisting of MI-63, MI-219, MI-888, MI-77301/SAR405838, nutlin-3a, RG7112, RO5963, JNJ-26854165, roscovitine, flavopiridol, DRB, n-phosphonacetyl-1-aspartate PALA), pyrazofurin, actinomycin D, and any combination thereof.

Embodiment 191

The method or formulation of embodiment 188, wherein the drug comprises a direct p53 activator selected from the group consisting of CP-31398, PRIMA-1, PhiKan083, RITA, and any combination thereof.

Embodiment 192

The method or formulation of embodiment 188, wherein the drug comprises a p53 deacetylation inhibitor selected from the group consisting of sirtinol, suramin, a tenovin, 3,2',3',4'-tetrahydroxychalcone, and any combination thereof.

Embodiment 193

The method or formulation of embodiment 188, wherein the drug comprises a drug that inhibits nuclear export of p53 selected from the group consisting of leptomycin B (LMB) derivatives and any combination thereof.

Embodiment 194

The method or formulation of embodiments 170-193, wherein the p53 restoration therapy is selected from the group consisting of gene therapy, antisense therapy, and siRNA therapy.

Embodiment 195

The method or formulation of embodiments 170-194, wherein the therapy comprises inhibition of GLS, or the formulation comprises a drug that inhibits GLS.

Embodiment 196

The method or formulation of embodiment 195, wherein the inhibition of GLS comprises inhibition of GLS1.

Embodiment 197

The method or formulation of embodiment 196, wherein the inhibition of GLS1 comprises administration to the subject of a molecule selected from CB-839/Calithera, 968, BPTES, or DON.

Embodiment 198

The method or formulation of embodiment 195, wherein the inhibition of GLS comprises antisense therapy or siRNA therapy.

Embodiment 199

The method of embodiments 173-198, wherein the cancer comprises a cancer that contains detectable PRODH.

Embodiment 200

The method of embodiments 170 and 172-199, wherein the cancer comprises a cancer known to be amenable to p53 restoration therapy.

Embodiment 201

The method of embodiments 170 and 172-199, wherein the cancer comprises cells having at least one functional p53 allele.

Embodiment 202

The method of embodiments 170 and 172-199, wherein the cancer comprises cells having no functional p53 alleles.

Embodiment 203

The method of embodiments 170 and 172-202, wherein the cancer comprises a cancer known to be amenable to inhibition of glutaminase (GLS).

Embodiment 204

The method of embodiments 169, 170 and 172-202, wherein the cancer comprises breast cancer.

Embodiment 205

The method of embodiments 169, 170 and 172-202, wherein the subject comprises a mammal.

Embodiment 206

The method of embodiment 205, wherein the subject comprises a human.

Embodiment 207

The method of embodiments 170 and 172-206, wherein the combination therapy produces a synergistic effect.

Embodiment 208

The method of embodiments 170 and 172-207, wherein the combination therapy produces a synthetic lethal effect.

Embodiment 209

The method of embodiments 170 and 172-208, wherein the combination therapy permits the use of a lower dose of one or more drug(s) than the effective amount of that drug when administered alone.

Embodiment 210

An analog of N-propargylglycine (PPG) that is capable of occupying the proline binding pocket of proline dehydrogenase (PRODH) and forming a covalent bond with PRODH or a flavin adenine dinucleotide (FAD) cofactor of PRODH, wherein the PPG analog has the formula:

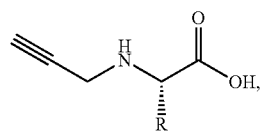

provided the PPG analog is not PPG.

Embodiment 211

The PPG analog of embodiment 210, wherein R is selected from the group consisting of: methyl, isopropyl, and isobutyl.

Embodiment 212

The PPG analog of embodiments 210 or 211, wherein the PPG analog is an S-enantiomer.

Embodiment 213

The PPG analog of embodiments 210-212, wherein the PPG analog is an irreversible inhibitor of PRODH.

Embodiment 214

The PPG analog of embodiment 213, wherein the irreversible inhibitor induces PRODH degradation.

Embodiment 215

The PPG analog of embodiments 210-214, wherein the PPG analog is produced by the synthetic scheme:

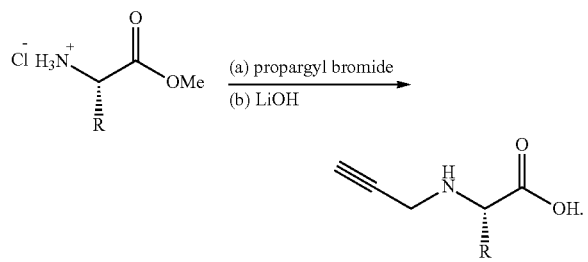

Embodiment 216

A pharmaceutical formulation comprising the PPG analog of any of embodiments 210-215 in a pharmaceutically acceptable carrier.

Embodiment 217

A method for determining whether a subject with cancer is a candidate for a cancer treatment method comprising inhibition of proline catabolism or inhibition of glutaminase (GSL), the method comprising:
- (a) assaying a sample of the cancer for proline dehydrogenase (PRODH) level; and
- (b) if PRODH is elevated relative to a normal level, identifying the subject as one who is a candidate for a cancer treatment method comprising inhibition of proline catabolism and/or as one who is likely to have a reduced response to a cancer treatment method consisting of inhibition of GLS1 alone; and
- (c) if PRODH is not elevated relative to a normal level, identifying the subject as one who is a candidate for a cancer treatment method comprising inhibition of GLS.

Embodiment 218

The method of embodiment 217, wherein the method additionally comprises assaying the sample for one or more of P5C dehydrogenase (PC5DH), glutamate dehydrogenase (GLDH), and P5C reductase-1 (PYCR1).

Embodiment 219

The method of embodiment 217, wherein if PRODH is elevated relative to a normal level, the method comprises identifying the subject as one who is a candidate for the treatment method of embodiments 169, 170 and 172-209.

Embodiment 220

The method of embodiment 217, wherein the method additionally comprises testing a sample of the cancer to determine whether cancer cells comprise at least one functional p53 allele.

Embodiment 221

The method of embodiment 220, wherein if the cancer cells are determined to comprise at least one functional p53 allele, the method comprises identifying the subject as one who is a candidate for the treatment method of embodiments 170 and 172-209.

Embodiment 222

The method of embodiment 220, wherein if the cancer cells are determined to comprise no functional p53 alleles, the treatment method comprises identifying the subject as one who is a candidate for the method of embodiments 194-209.

Embodiment 223

The method of embodiment 217, wherein the method additionally comprises assaying the sample for GLS level; and if GLS is elevated relative to a normal level, identifying the subject as one who is a candidate for a cancer treatment method comprising inhibition of GLS and/or as one who is likely to have a reduced response to a cancer therapy consisting of inhibition of proline catabolism alone; and if GLS is not elevated relative to a normal level, identifying the subject as one who is a candidate for a cancer treatment method comprising inhibition of proline catabolism.

Embodiment 224

The method of embodiment 223, wherein the GLS level comprises a GLS1 level.

Embodiment 225

The method of embodiments 223-224, wherein the GLS level comprises a GLS2 level.

Embodiment 226

The method of embodiments 217-225, wherein the PRODH level comprises a PRODH protein level assayed by immunohistochemistry.

Embodiment 227

The method of embodiments 218-226, wherein the method comprises additionally assaying the sample for one or more of GLS, P5C dehydrogenase (PC5DH), glutamate dehydrogenase (GLDH), and P5C reductase-1 (PYCR1), wherein said additional assay comprises an immunohistochemistry assay.

Embodiment 228

A method comprising: (a) assaying a sample of cancer obtained from a subject for proline dehydrogenase (PRODH) level; and (b) if, based on said PRODH assay, the PRODH level is elevated relative to a normal level, treating the subject with a drug that inhibits proline catabolism.

Embodiment 229

The method of embodiment 228, wherein if PRODH is elevated relative to a normal level, the method comprises treating the subject according to the treatment method of embodiments 169, 170 and 172-209.

Embodiment 230

The method of embodiment 228, wherein the method comprises additionally testing a sample of the cancer to determine whether cancer cells comprise at least one functional p53 allele.

Embodiment 231

The method of embodiment 230, wherein if the cancer cells are determined to comprise at least one functional p53 allele, the method comprises treating the subject according to the treatment method of embodiments 170 and 172-209.

Embodiment 232

The method of embodiment 230, wherein if the cancer cells are determined to comprise no functional p53 alleles, the treatment method comprises treating the subject according to the treatment method of embodiments 194-209.

Embodiment 233

The method of embodiment 228, wherein the method comprises additionally assaying the sample for GLS level; and if, based on said GLS assay, the GLS level is elevated relative to a normal level, treating the subject with a drug that inhibits GLS.

Embodiment 234

The method of embodiment 233, wherein if the GLS is elevated relative to a normal level, the method comprises treating the subject according to the treatment method of embodiments 195-209.

Embodiment 235

The method of embodiment 234, wherein the GLS level comprises a GLS1 level.

Embodiment 236

The method of embodiments 234-235, wherein the GLS level comprises a GLS2 level.

Embodiment 237

The method of embodiments 228-232, wherein the PRODH level comprises a PRODH protein level assayed by immunohistochemistry.

Embodiment 238

The method of embodiment 233-237, wherein the GLS comprises a GLS protein level assayed by immunohistochemistry.

Definitions

The terms "subject", "individual", and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments the subject may not be under the care or prescription of a physician or other health worker.

The phrases "an effective amount" and "an amount sufficient to" refer to amounts of a biologically active agent that produce an intended biological result or activity.

The term "co-administer" indicates that the two agents are administered so that there is at least some chronological overlap in their physiological activity on the organism. Thus, a first agent can be administered simultaneously and/or sequentially with a second agent. In sequential administration, there may even be some substantial delay (e.g., minutes or even hours or days) before administration of the second agent as long as the first-administered agent is exerting some physiological effect on the organism when the second administered agent is administered or becomes active in the organism.

As used herein, "a combination therapy" refers to a therapy in which at least two therapeutic targets are addressed by the therapy.

As used herein, "p53 restoration therapy" includes any treatment that enhances the normal function of the tumor suppressor protein, p53.

The following terms encompass polypeptides that are identified in Genbank by the following designations, as well as their orthologs: p53, glutaminase (GLS, e.g., GLS1, GLS2), proline dehydrogenase (PRODH), P5C dehydrogenase (PC5DH), glutamate dehydrogenase (GLDH), Mdm2, and Mdmx.

As used herein, the term "synergistic effect" refers to an effect produced by two agents that is greater than, or otherwise different from, the sum of their individual effects.

As used herein, the term "synthetic lethal effect" refers to a lethal effect (e.g., cell death) produced by addressing two therapeutic targets simultaneously, where addressing either target alone may be non-lethal (e.g., may not lead to cell death).

As used herein, the term "pharmaceutically acceptable" refers to an agent that is bioavailable and sufficiently well-tolerated by subjects for pharmaceutical use.

The term "derivative" refers to any salt, ester, amide, prodrug, or other derivative of any compound that has at least one pharmacological effect of that compound that renders it useful in one or more of the therapeutic and/or prophylactic methods described herein and is pharmaceutically acceptable.

As used herein with respect to an analyte in a cell or tissue, the term "normal level" refers to the typical level (or range) at which the analyte is present in a normal (non-cancerous) cell or tissue. The term "normal level" may, in some cases be "zero" or "undetectable" in a particular assay.

The phrase "elevated relative to a normal level" is used herein to describe an analyte that is present in a cell or tissue at level that is higher than the normal level. Where the normal level is zero or undetectable in a particular assay, the mere detection of the analyte may qualify as "elevated."

The term "health span" refers to the period of time during which an individual meets one or more selected measures of health span. An increase in "health span" refers to an extension in the period of health, according to such measures, as compared to the period of health in a control population. An increase in health span can be measured, e.g., by determining the length of time that an individual continues to meet the one or more selected measure(s) of health span. In certain embodiments an increase in health span can be determined by measuring a degree of improvement in one or more selected measures of health span that are correlated with an increase in the length of time that an individual continues to meet the selected measures of health span.

The term "frailty" refers to a condition that can be characterized by (typically, three or more) symptoms selected from weakness, weight loss, slowed mobility, fatigue, low levels of activity, poor endurance; and impaired behavioral response to a sensory cue. Frailty can also be characterized by an increase in one or more inflammatory biomarkers, glucose homeostasis impairment, and/or an increase in one or more biomarkers of clotting activation. Another hallmark of frailty is "sarcopenia," which refers to age-related loss of muscle mass." Frailty can also refer to a reduced ability to maintain homeostasis during the application of a stressor and/or an increase in the time required to return to homeostasis after the application of a stressor. Frailty can also include a decline in mitochondrial function, typically with changes in respiration, and/or morphological aberrations in mitochondria.

An "age-related disability," refers to any physical or mental incapacity associated with normal aging, such as, for example, an age-related decline in near vision.

An "age-related disease" refers an abnormal condition characterized by a disordered or incorrectly functioning organ, part, structure, or system of the body that occurs more frequently in the aged.

As used herein, a "control population," refers to a population that has not been to inhibit proline catabolism, wherein the members of that population have one or more characteristics and/or conditions of a subject being treated to inhibit proline catabolism as described herein. Thus, for example, if a subject is being treated for frailty, the relevant control population would have frailty; and if a subject is being treated for and age-related disability or disease, the relevant control population would have the same disability or disease.

The term "inflammatory biomarker" refers to an endogenous condition, often the presence, level, and/or form of a molecule, that indicates the presence of inflammation. For, example, C-reactive protein (CRP), is an inflammatory biomarker that has been shown to predict future cardiovascular events in individuals with and without established cardiovascular disease (CVD). Biomarkers implicated in the inflammatory process leading to atherothrombosis, include, for example, CRP, adiponectin, monocyte chemoattractant protein 1 (MCP-1), CD40 ligand and lipoprotein-associated phospholipase A(2) (Lp-PLA(2)).

The term "glucose homeostasis" refers to the state of, or tendency toward, normal (non-pathological) glucose levels, which vary appropriately in response to various stimuli. Illustrative measure of glucose homeostasis include meal-stimulated insulin, glucose, and glucagon-like peptide-1 (GLP-1) levels.

The term "biomarker of clotting activation" refers to an endogenous condition, often the presence, level, and/or form of a molecule, that indicates activation of the pathway leading to the formation of a blood clot. Illustrative biomarkers of clotting activation include, for example, pro-thrombin fragments 1 and 2 (F1+2), thrombin-antithrombin complex (TAT), and fibrin degradation products (D-dimer)

The term "lipofuscin" refers to lipopigments that are made up of fats and proteins. Lipofuscin take on a greenish-yellow color when viewed under an ultraviolet light microscope. Lipofuscins can build up in neuronal cells and many organs, including the brain, liver, spleen, myocardium, and kidneys, excessive accumulation can lead to neurodegenerative disorders, such as neuronal ceroid lipofuscinoses.

The term "autophagy pathway" refers to a self-cannibalisation pathway that is one of the main mechanisms for maintaining cellular homeostasis. Mediated via the lysosomal degradation pathway, autophagy is responsible for degrading cellular proteins and cellular organelles (including mitochondria, when it is referred to as mitophagy), recycling them to ensure cell survival. Autophagy includes three processes: microautophagy, macroautophagy and chaperone-mediated autophagy. "Microautophagy" is the transfer of cytosolic components into the lysosome by direct invagination of the lysosomal membrane and subsequent budding of vesicles into the lysosomal lumen. "Macroautophagy" involves formation of a double-membrane structure called the autophagosome which sequesters cytosolic material and delivers it to the lysosome for degradation. This degradation can be selective (i.e., specifically removing damaged mitochondria, while sparing normal functioning ones); however, degradation of soluble cytosolic proteins is non-selective. "Chaperone-mediated autophagy" (CMA) is characterized by its selectivity in degrading specific substrates (cytosolic proteins). Genetic screens in yeast (*S. cerevisiae*) have led to the identification of over ~30 autophagy-related genes (ATG-genes), many of which have identified mammalian homologues. Examples of the latter include hAPG5, Beclin-1, HsGSA7/haPG7, MAP1LC3, hAPG12, PTEN, and LAMP-2

The term "ubinquitination" refers to the tagging of proteins for selective destruction in proteolytic complexes called proteasomes by covalent attachment of ubiquitin, a small, highly conserved protein. An isopeptide bond links the terminal carboxyl of ubiquitin to the g-amino group of a lysine residue of a "condemned" protein. Three enzymes are involved. Initially, the terminal carboxyl group of ubiquitin is joined in a thioester bond to a cysteine residue on ubiquitin-activating enzyme (E1). This step is dependent on ATP. The ubiquitin is then transferred to a sulfhydryl group on a ubiquitin-conjugating enzyme (E2). A ubiquitin-protein ligase (E3) the transfers ubiquitin from E2 to the ε-amino group of a lysine residue of a protein recognized by that E3, forming an isopeptide bond. More ubiquitins may be added to form a chain of ubiquitins. The terminal carboxyl of each ubiquitin is linked to the g-amino group of a lysine residue (Lys29 or Lys48) of the adjacent ubiquitin in the chain. A chain of four or more ubiquitins targets proteins for degradation in proteasomes.

As used herein, "inclusion bodies" refer to nuclear or cytoplasmic aggregates of stainable substances, typically proteins. Proteins in inclusion bodies may be misfolded. "Inclusion body myocitis" refers to an age-related, inflammatory muscle disease, characterized by slowly progressive weakness and wasting of both distal and proximal muscles, most apparent in the muscles of the arms and legs. In sporadic inclusion body myositis, two processes, one autoimmune and the other degenerative, appear to occur in the muscle cells in parallel. The inflammation aspect is characterized by the cloning of T cells that appear to be driven by specific antigens to invade muscle fibers. The degenerative aspect is characterized by the appearance of vacuoles and deposits of abnormal proteins in muscle cells and filamentous inclusions.

The term "protein trafficking" refers to the movement of proteins within a cell. For example, nascent proteins may be targeted to the cytosol, mitochondria, peroxisomes or chloroplasts. These proteins (if encoded in the nucleus) are synthesized on free ribosomes. However, proteins destined for secretion, for the lumen of the endoplasmic reticulum (ER), Golgi or lysosomes, or for the membrane of any of these organelles or the plasma membrane, are synthesized on the membrane-bound ribosomes of the rough ER. They are then targeted to the appropriate cellular compartment. It is estimated that over 100 inherited human diseases, such as cystic fibrosis, lysosomal storage diseases, and long QT syndrome, are due to protein trafficking defects, typically caused by mutations in secreted proteins which prevent proper folding of the protein. These mutant proteins fold inefficiently and, thus, fail to exit the ER. This produces a "loss of function" phenotype. The misfolded proteins are detected by a quality control system in the ER and are degraded by the ubiquitin proteasome system.

BRIEF DESCRIPTION OF THE DRAWINGS

FIG. 4A. PRODH mRNA expression levels (normalized, log 2-scaled) across 51 different human breast cancer cell lines determined from published microarrays (Neve et al. (2006) Cancer Cell. 10: 515-527) and color coded by intrinsic subtype, highest in luminal and lowest in triple-negative breast cancers. FIG. 4B. PRODH and GLS1 mRNA levels are strongly inversely correlated; the indicated models are among those being evaluated for combination therapy with PRODH and GLS1 inhibitors. FIG. 4C. MCF7 single dose and time point cell viability assay showing additive interactions at 48 h after combined treatment with a GLS1 inhibitor (CB-839) and two different PRODH inhibitors (5-oxo or PPG). FIG. 4D. Similar cell viability study in non-malignant MCF10A cells showing no treatment effects.

FIG. 5A, top left: We structurally modeled both the pre- and post-reactive PPG inhibitor within the human PRODH enzymatic pocket showing its covalent linkage with FAD and pocket distortion, and also proving irreversibility. We also modeled human PRODH's catalytic site containing the tyrosine (Y548) and arginine (R564, R563) H-bonded to the competitive inhibitor, (S)-(+)-5-oxo-2-tetrahydrofurancarboxylic acid (5-oxo). The FAD moiety and intercalated water molecule are shown. FIG. 5A, top right: Structure of 5-oxo. FIG. 5A, lower: Since the N-propargyl moiety has been successfully used to develop irreversible (suicide) flavin-enzyme inhibitors and drugs (e.g. rasagiline to treat Parkinson's), we synthesized N-propargylglycine (PPG) and produced models of both the pre- and post-reactive PPG structure within the human PRODH enzymatic pocket showing its covalent linkage with FAD and resulting pocket distortion. We proved irreversibility. FIG. 5B: To test our human PRODH structural model, improve upon the enzymatic pocket affinity and reactivity based on the PPG scaffold, and to generate more potent PRODH suicide inhibitors being synthesized, we modeled and evaluated new chemical entities such as the related structures shown below both as free compounds and in their predicted post-reactive FAD-bound state within PRODH. Our model predicted that the (S) enantiomer of PPG-Me might interfere with Y560 (dash circle), and following synthesis of this entity we confirmed its lack of PRODH inhibiting activity using our mitochondrial PRODH assay. In contrast, upon synthesis of (R/S)-PPG we have shown that it retains PRODH inhibiting activity in this same assay, demonstrating our model's prediction that the placement of the methyl group in this PPG-like scaffold strongly influences the inhibitor's pocket affinity.

DETAILED DESCRIPTION

Figure 1:
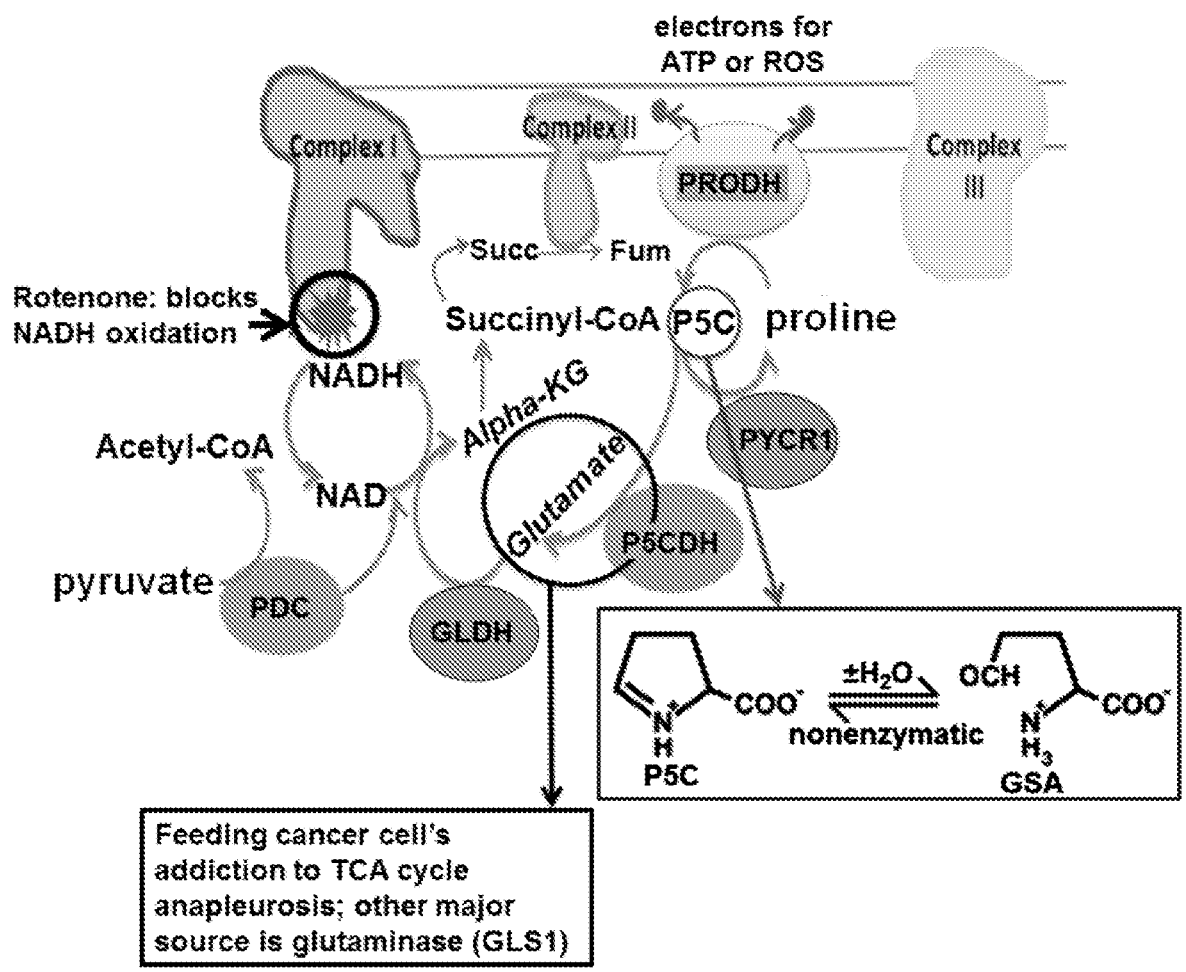
FIG. 1: Induced by p53, mitochondrial PRODH catalyzes the first step of proline oxidation to produce the unstable metabolic intermediate, P5C, with two electrons transferred into the electron transport chain for either ATP production or ROS generation, and downstream mitochondrial reactions generating glutamate, $\alpha$-KG, and NADH. Pyruvate oxidation by PDC produces acetyl Co-A and also increases the NADH pool. Rotenone blocks all Complex 1 oxidation of NADH to NAD.

It was a surprising discovery that the p53-inducible gene and mitochondrial enzyme, proline dehydrogenase (PRODH), supports breast cancer cell survival by supplying much needed energy and mitochondrial carbon nutrients, especially under nutritional and hypoxic stress conditions, using proline for anaplerotic glutamate production and bypassing glutaminase (GLS1), to fuel oxidative phosphorylation and sustain ATP levels. Our study of MDM2-inhibiting anticancer agents like MI-63 that restore wildtype p53 expression indicates that p53 induction of PRODH serves to support breast cancer survival and, by implication, survival of other cancers.

Furthermore, it was discovered that PRODH knockdown, or its enzymatic inhibition by either proline competitive inhibitors like L-THFA and 5-oxo-2-tetrahydrofurancarboxylic acid (5-oxo) or the more potent mechanism-based PRODH "suicide" inhibitor, N-propargylglycine (PPG), not only impairs breast cancer growth by itself, but when combined with either a p53 restoring drug (e.g., MI-63 or nutlin-3a) or a clinical GLS1 inhibitor (e.g. CB-839) produces a "synthetic lethal" and synergistic anticancer response against malignant but not normal breast epithelial cells. The data described herein show that a sustained and full inhibition of proline catabolism (e.g., by inhibition of PRODH) induces cancer cell (but not normal cell) apoptosis offering a new cancer therapeutic strategy, Accordingly, in various embodiments, methods of treating cancer in a subject are provided where the methods involve inhibiting proline catabolism in the subject. Enzymes that participate in proline catabolism include proline dehydrogenase (PRODH), P5C dehydrogenase (PC5DH), glutamate dehydrogenase (GLDH), and any of these can be inhibited alone or in any combination to inhibit proline catabolism. In some embodiments, PRODH is inhibited alone (i.e., PRODH is the only proline catabolic enzyme inhibited) or in some embodiments, PRODH is inhibited in combination with inhibition of PC5DH or GLDH or both. In certain embodiments, PC5DH is inhibited alone (i.e., PC5DH is the only proline catabolic enzyme inhibited) or in some embodiments PC5DH is inhibited in combination with GLDH. In certain embodiments GLDH alone is inhibited (i.e., GLDH is the only proline catabolic enzyme inhibited).

Any of these therapies can be combined with another cancer therapy, such as p53 restoration therapy and/or inhibition of glutaminase (GLS).

In certain embodiments, the combination therapies of inhibition of proline catabolism and p53 restoration or inhibition of proline catabolism and glutaminase produce a synergistic effect. In particular embodiments, the combination therapies produce a synthetic lethal effect, i.e., induce additive or synergistic apoptosis, when neither therapy alone may be capable of doing so. In some embodiments, a combination therapy described herein permits the use of a lower dose of one or both drugs administered in the combination therapy than the effective amount of that drug when administered alone.

It was also discovered that inhibition of proline catabolism provides an even more striking effect in cells subject to hypoxia (see, e.g., FIG. 3) thus, the methods are expected to prove even more effective in cancer characterized by hypoxic cells (e.g., as in a solid tumor). It is also believed that the anti-cancer effect can be improved by administration with agents that increase tumor hypoxia (e.g., anti-angiogenic drugs).

Additionally, assay methods are provided that identify cancers in which the methods described herein are expected to show increased efficacy. For example in a cancer associated with reduced p53 a therapy comprising inhibition of proline catabolism combined with p53 rescue therapy is expected to show improved efficacy. Similarly where glutaminase is upregulated in the cancer, a therapy comprising inhibition of proline catabolism combined glutaminase inhibition is expected to show improved efficacy.

It was also a surprising discovery that appropriately timed and transient (hormetic) dosing with a cancer treating irreversible ("suicide") inhibitor of PRODH can also activate healthspan-inducing mitohormesis in a normal organism increasing its resistance to stress and disease and significantly enhancing its median and overall lifespan. Accordingly, in certain embodiments, methods of improving lifespan/healthspan and/or reducing biological stress in an organism are provided where the methods involve inhibiting PRODH, preferably with a suicide inhibitor.

Inhibition of Proline Catabolism.

As explained above, inhibition of proline catabolism can provide an effective method of treating a cancer, and/or improving lifespan/healthspan, and/or more resiliently adapting to physiological stress. Enzymes that participate in proline catabolism include proline dehydrogenase (PRODH), P5C dehydrogenase (PC5DH), glutamate dehydrogenase (GLDH), and any of these can be inhibited alone or in any combination to inhibit proline catabolism.

In certain embodiments PRODH is inhibited and may be irreversibly inhibited. It was discovered that irreversible PRODH inhibition has little or no adverse impact on healthy cells and, as noted above, may activate healthspan-inducing mitohormesis in a normal organism. In certain embodiments PRODH can be inhibited in a subject by administering to the subject any pharmaceutically acceptable PRODH inhibitor.

In some embodiments, suitable PRODH inhibitors are capable of occupying the proline binding pocket of PRODH and forming one or more hydrogen bonds with the residue corresponding to tyrosine 548, arginine 563, and/or arginine 564 of mature human PRODH (numbered according to Bender et al. (2005) *Am. J. Hum. Genet.* 76:409-420). Examples of this type of inhibitor include (S)-5-oxo-tetrahydrofuran carboxylic acid and derivatives thereof. Based on this structure, additional molecules can be designed and tested to identify further such inhibitors. Other PRODH inhibitors include tetrahydro-2-furoic acid (L-THFA), L-4-thiazolidine carboxylic acid, L-3,4-dehydroproline, 4-methylene-L-proline, (E)- and (Z)-4-(fluoromethylene)-L-proline, cis- and trans-5-ethynyl-(+)-proline, cis-5-vinyl-L-proline, trans-5-vinyl-L-proline, cis-4-fluoro-L-proline, trans-4-fluoro-L-proline, 4,4-difluoro-L-proline, 5-fluoro-L-proline, and derivatives thereof. In some embodiments, two or more of these compounds are administered in combination.

In certain embodiments, PRODH inhibitors are capable of occupying the proline binding pocket of PRODH and forming a covalent bond with PRODH or a flavin adenine dinucleotide (FAD) cofactor of PRODH. Such inhibitors are extremely effective because they are not reversible and, in fact, have been found to induce degradation of PRODH. Examples of inhibitors believed to operate by this mechanism include N-propargylglycine (PPG) and novel analogs thereof. Novel PPG analogs include PPG-like structures that may preserve the reactive propargylic mechanism but include hydrophobic substituents, while, in certain embodiments, also creating chiral α-carbon structures for stereospecificity. In some embodiments, such analogs have the formula:

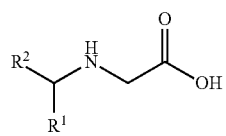

where $R^1$ is a hydrophobic moiety (including $R^1$=H) and $R^2$ is selected from the group consisting of

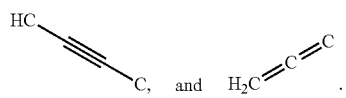

In certain embodiments $R^1$ is a hydrophobic moiety that can be accommodated in the proline binding pocket of PRODH. In certain particular embodiments $R^1$ is selected from the group consisting of H, $C_1$-$C_4$ alkyl, halogen, and $C_1$-$C_4$ haloalkyl. In certain embodiments $R^1$ is selected from the group consisting of H, methyl, ethyl, isopropyl, isobutyl, Br, Cl, F, $CF_3$, and $CCl_3$. In certain embodiments $R^1$ is selected from the group consisting of H, methyl, ethyl, isopropyl, and isobutyl.

In certain embodiment the analog has the formula:

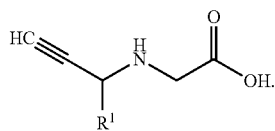

or the analog has the formula:

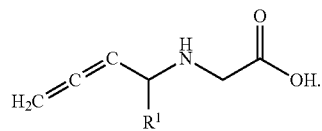

In certain embodiments $R^1$ is methyl. In certain particular embodiments, the analog has the formula:

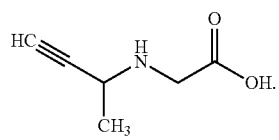

In certain embodiments $R^1$ is H. In certain particular embodiments, the analog has the formula:

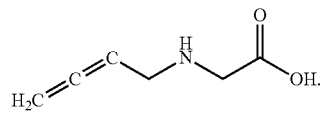

Synthesis of N-propargylglycine (PPG) can be achieved following a previously reported method (Dietrich et al. (1980) Organic Magnetic Resonance 13: 79-88). In brief, to a 1:1 volume mixture of propargylamine (Sigma) and water a 0.1 M amount (relative to propargylamine) of iodoacetic acid is slowly added. The resulting solution is incubated at room temperature for 24 h, followed by speedyvac removal of the water. To the residual brown viscous liquid is added 0.5 volumes of ethanol followed by the slow addition of 6 volumes of acetone mixed together with 0.65 volumes of ethanol. The resulting N-propargylglycine precipitate is collected and washed extensively with acetone/ethanol using a Buchner funnel. The dried power (light beige color) can be confirmed as N-propargylglycine by H-NMR spectroscopy.

Synthesis of (R/S)-PPG and AG (FIG. 5B) can be accomplished using the same iodoacetate method outlined above for PPG where, instead of propargylamine, the beginning compound is 1-methyl-prop-2-ynylamine (Combi-Blocks, San Diego, Calif.) to generate (R/S)-PPG, or 2,3-butadien-1-amine (Sigma) to generate AG.

Figure 8:
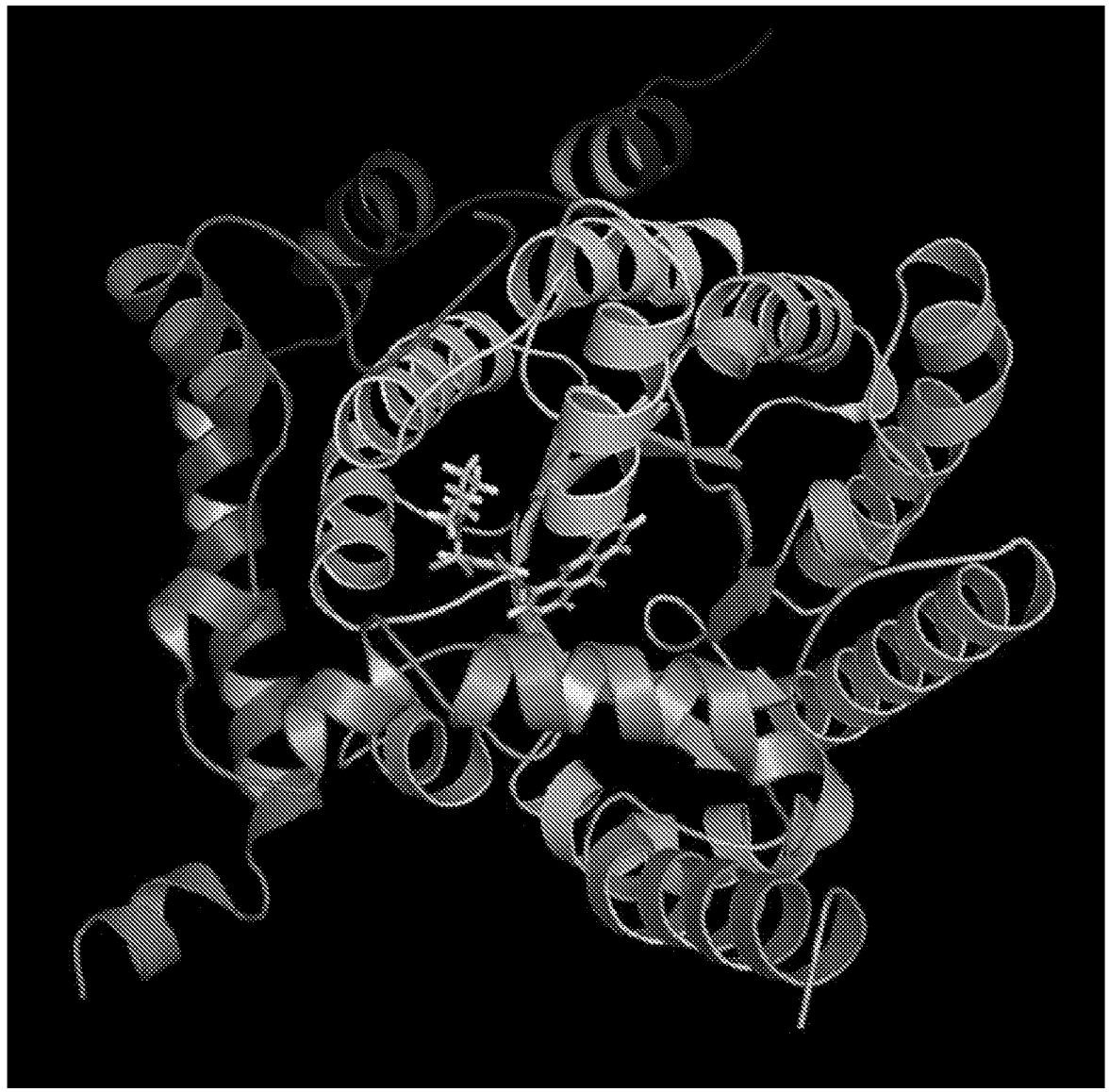
FIG. 8: Model of PRODH's entire catalytic pocket largely occupied by one structural candidate from Table 1 (compound 40); all such candidates designed for maximal fit and specific PRODH pocket binding such that the co-factor FAD is replaced.
Figure 9:
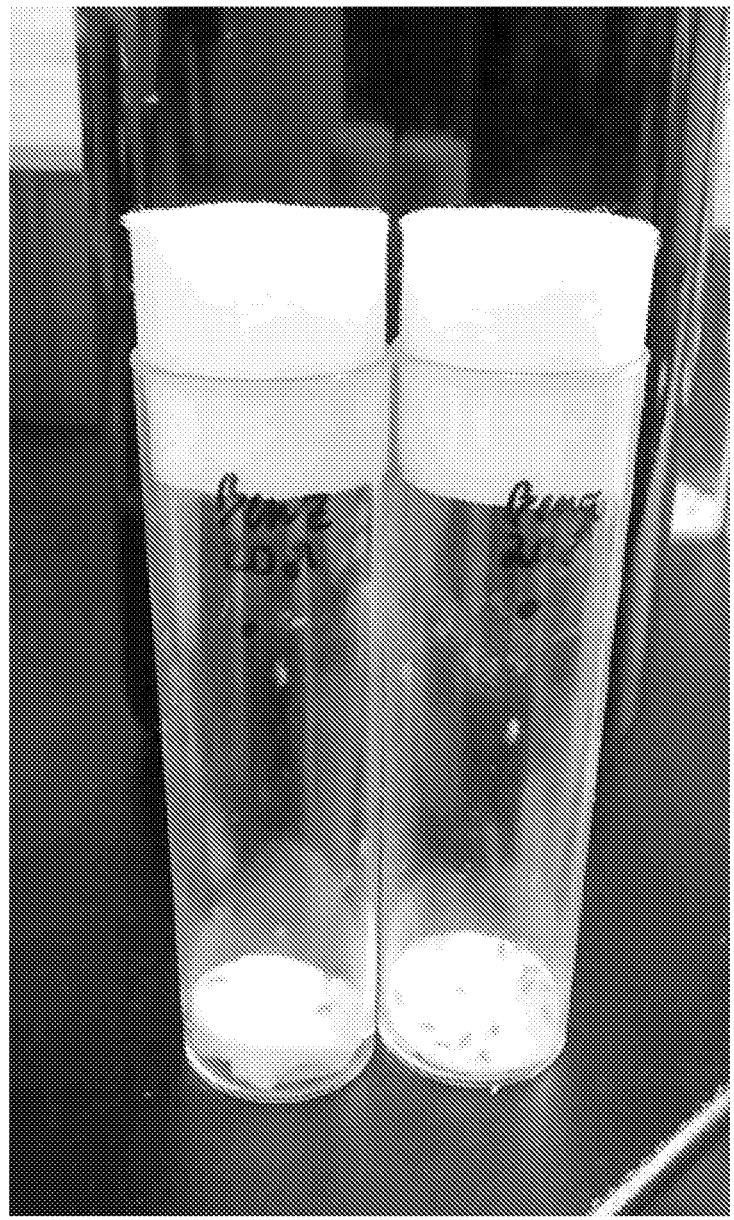
FIG. 9: Dietary PPG completely inhibits PRODH in vivo: Adult *Drosophila* PPG intake (5 mM×48 h, right tube) fully mimicks "Sluggish-A" (PRODH gene knockout) phenotype without loss of fly viability (control treated flies in left tube).
Figure 10:
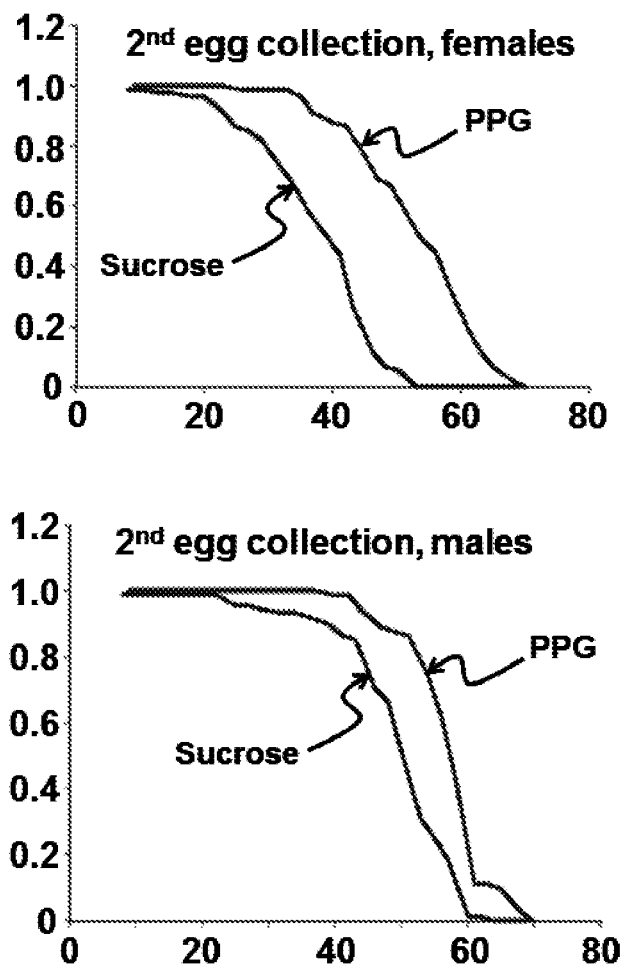
FIG. 10: Dietary PPG (5 mM×24 h) given during a critical phase of *Drosophila* oogenesis significantly extends median and maximum lifespan of the flies. Female *Drosophila* were starved for 4 h, then combined with males on liquid 5% sucrose food with or without 5 mM PPG. After 24 h, females were transferred to egg collection containers, and eggs collected after 1, 2, and 3 days. Collected eggs were transferred to bottles of regular food, separately for each collection day. Larvae developed normally, were transferred to vials after eclosion; vials were exchanged thrice weekly throughout life. Data shows lifespan plots over 70 days for enclosed $2^{nd}$ day collected fertilized eggs (90 females, 90 males).

Additional small-molecule PRODH inhibitors are shown below in Table 1. These PRODH inhibitors were derived from molecular modeling to identify compounds that fully occupy the PRODH catalytic pocket, including replacement of the pocket-bound FAD, and thereby prevent enzyme activity. FIG. 8 illustrates the proposed configuration of one of these candidates within the PRODH pocket. These compounds are commercially available, and the vendors are indicated in Table 1. Their inhibitory activity can be quantified using any of the PRODH assays described herein.

TABLE 1

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
|---|---|---|---|
| 1 | [structure] | 409.439<br>3.944<br>85.959<br>5* | ChemDiv<br>G725-1440 |
| 2 | [structure] | 548.59<br>0.192<br>142.93<br>2 | Vitas-M<br>STK88654<br>Pharmeks<br>PHAR140148 |
| 3 | [structure] | 467.562<br>3.68<br>0<br>5 | Aldrich<br>117386808 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
|---|---|---|---|
| 4 | 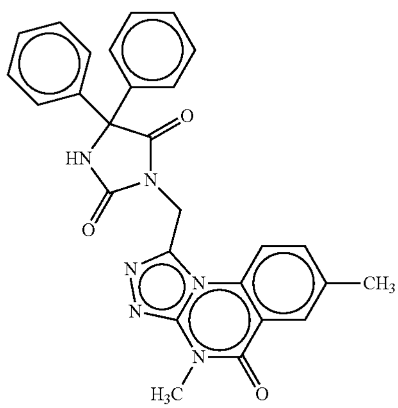 | 478.501 2.41 0 4 | UkrOrg-Synthesis PB424888234 |
| 5 | 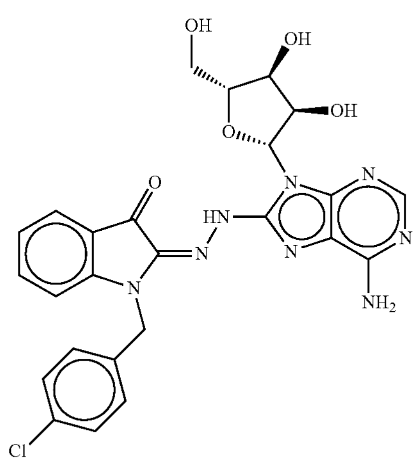 | 550.953 2.38 0 6 | Aldrich 23407751 Pharmeks PHAR117156 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
|---|---|---|---|
| 6 | 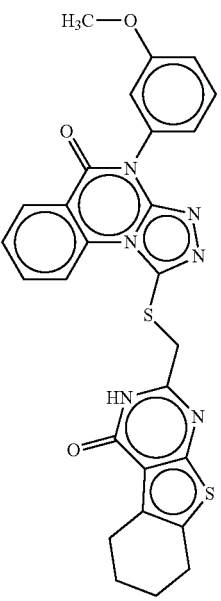 | 542.631 3.273 155.25 5 | Enamine T5271947 |
| 7 | 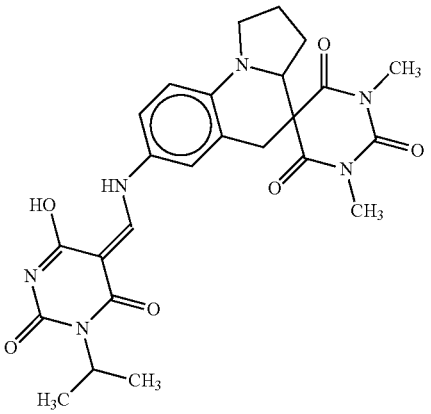 | 508.526 −0.988 142.93 2 | Vitas-M STK573905 Pharmeks PHAR125812 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
|---|---|---|---|
| 8 | 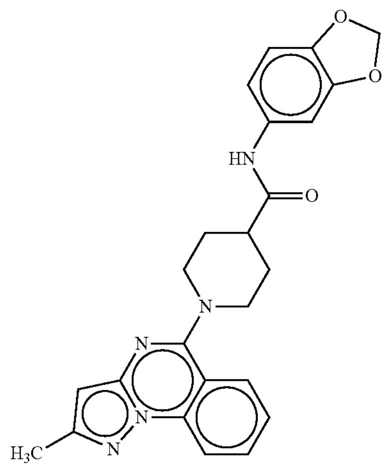 | 429.471 3.99 80.989 4 | Enamine T6322336 UkrOrg-Synthesis PB424863934 Enamine Z354282546 Aldrich 18070120 |
| 9 | 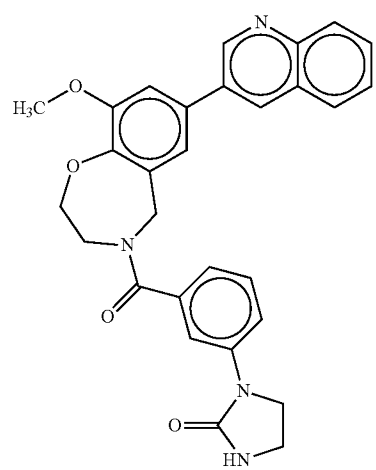 | 494.541 3.82 84 5 | ChemBridge 77982657 Aldrich 181369800 |
| 10 | 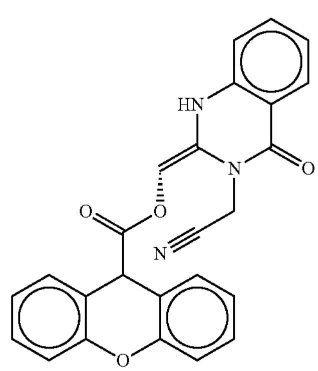 | 423.42 3.84 0 5 | Aldrich 37962771 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
|---|---|---|---|
| 11 | 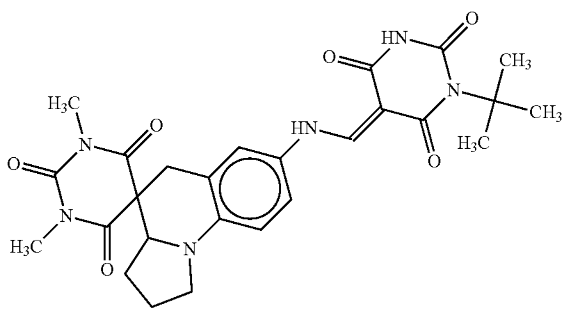 | 522.552 1.482 139.44 3 | IBScreen STOCK5S-88502 Vitas-M STL008398 Aldrich 6197539 |
| 12 | 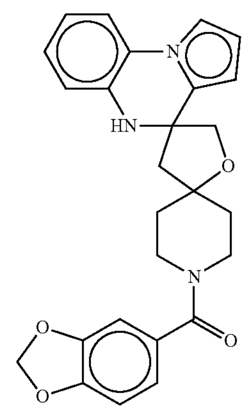 | 443.494 1.375 64.959 2 | Asinex ADD1381423 Aldrich 332977936 |
| 13 | 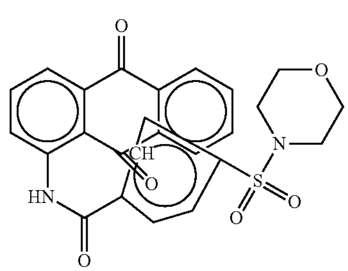 | 476.501 2.69 109.85 5 | ChemDIv 0831-0061 Enamine T0500-4956 ChemBridge 5921867 Life Chemicals F0013-0061 UkrOrg-Synthesis PB-90097274 Aldrich 28250997 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
|---|---|---|---|
| 14 | 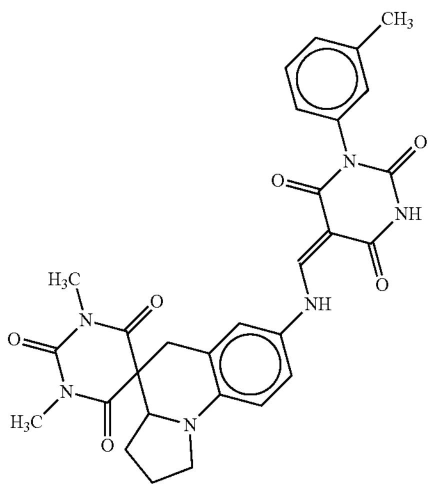 | 556.569 1.513 139.44 3 | IBScreen STOCK5S-97167 Vitas-M STL008308 Aldrich 65055514 |
| 15 | 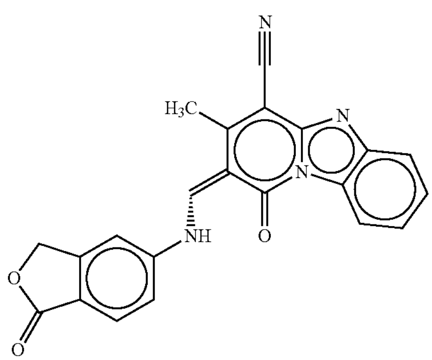 | 382.371 2.67 0 3 | Aldrich 34395518 |
| 16 | 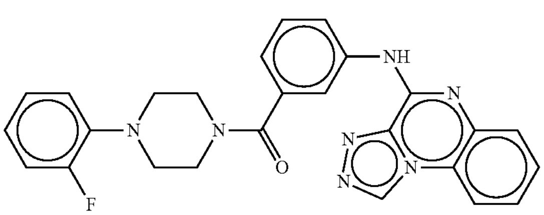 | 467.497 3.091 78.66 5 | ChemDiv C301-3704 Aldrich 61632590 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
| --- | --- | --- | --- |
| 17 | 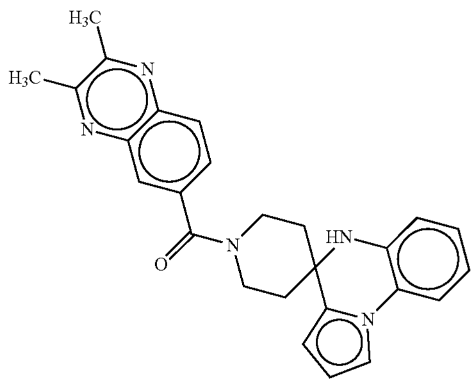 | 423.509 1.69 0 2 | Asinex AEM-11113340 Aldrich 333007571 |
| 18 | 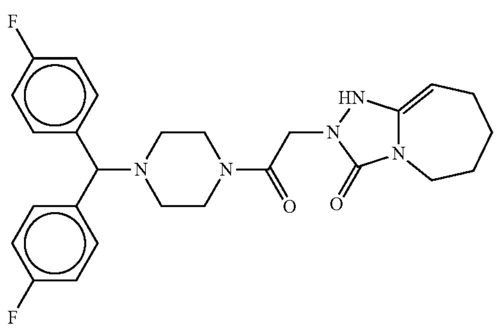 | 481.537 3.4 0 6 | Aldrich 155400319 |
| 19 | 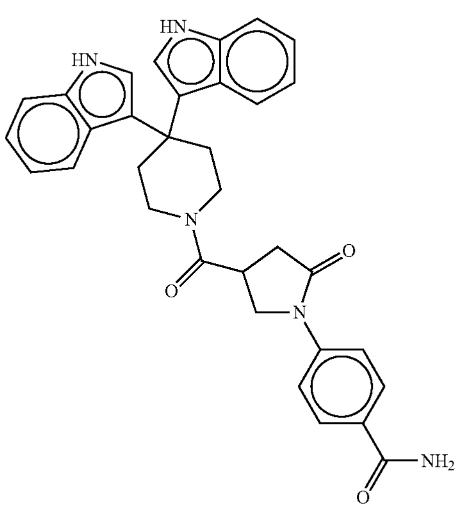 | 545.63 3.16 115.29 6 | Aldrich 363594839 ChemDiv S322-0090 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
|---|---|---|---|
| 20 | 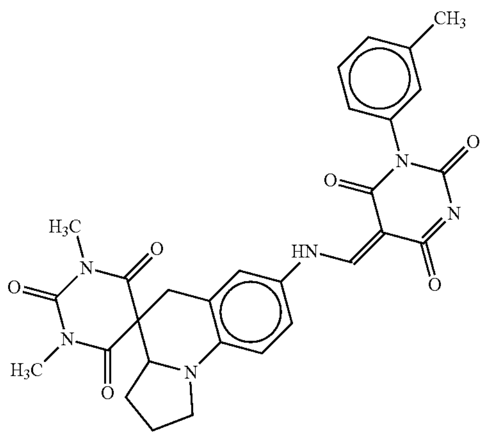 | 556.569 0.345 142.93 1 | Vitas-M STK831323 Pharmeks PHAR123134 |
| 21 | 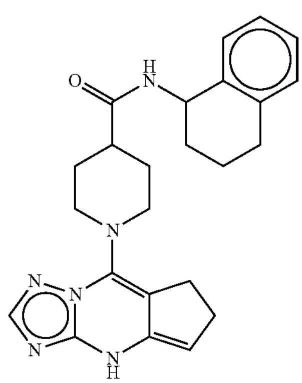 | 416.518 2.34 0 4 | Aldrich 47389253 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW<br>logP<br>TPSA<br>RB | Vendor<br>Catalog No. |
|---|---|---|---|
| 22 | 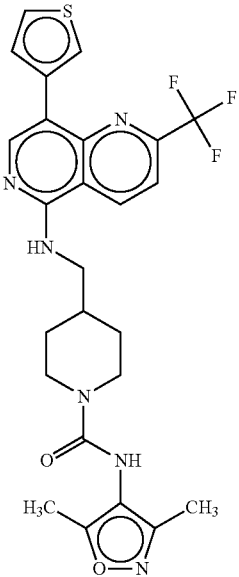 | 530.565<br>2.959<br>124.419<br>8 | Peakdale<br>Molecular<br>1016489<br>Aldrich<br>101282585 |
| 23 | 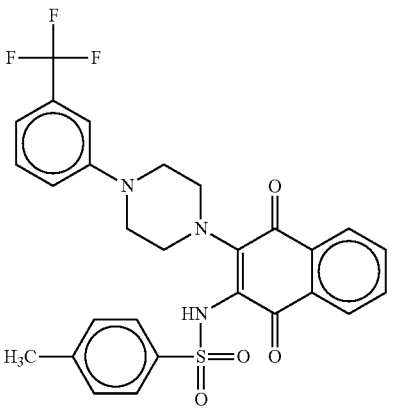 | 555.568<br>3.46<br>0<br>6 | Aldrich<br>29314384 |
| 24 | 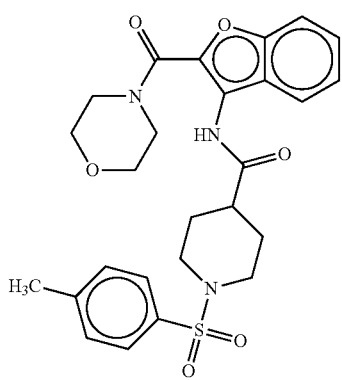 | 511.589<br>2.726<br>117.54<br>7 | ChemDiv<br>E002-2710<br>Aldrich<br>67502577 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
|---|---|---|---|
| 25 | 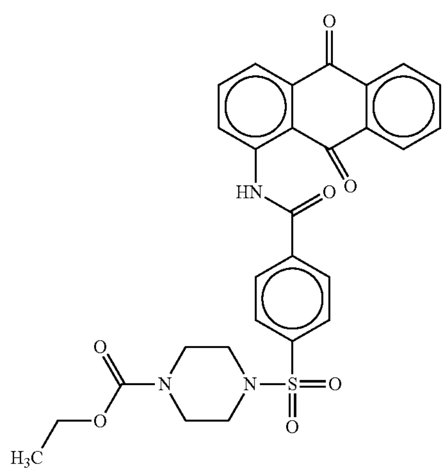 | 547.578 3.347 130.16 8 | ChemDiv 3343-2103 Life Chemicals F0834-1197 Aldrich 29796482 |
| 26 | 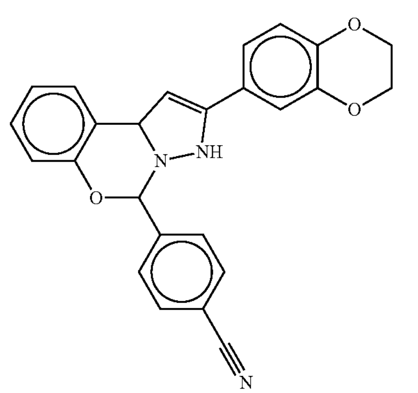 | 409.436 3.04 0 3 | Aldrich 29380733 |
| 27 | 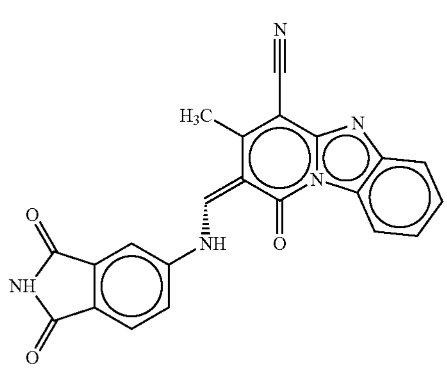 | 395.37 1.72 0 3 | Aldrich 34395522 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
| --- | --- | --- | --- |
| 28 | 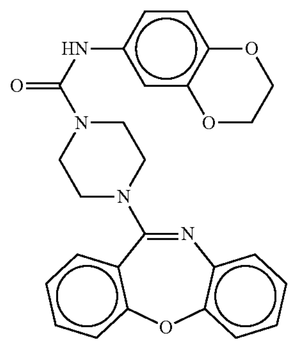 | 456.493 3.802 75.63 4 | ChemDiv F992-0176 Aldrich 111388699 |
| 29 | 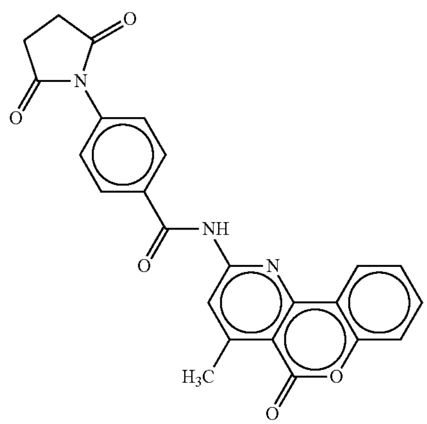 | 427.408 2.479 105.669 4 | Life Chemicals F0614-0106 Aldrich 30873123 |
| 30 | 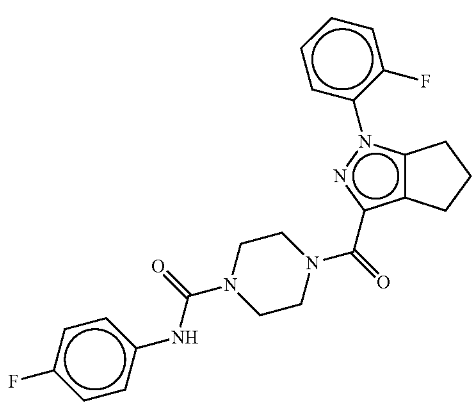 | 451.468 3.5 0 6 | ChemDiv C073-6425 Aldrich 30292264 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
|---|---|---|---|
| 31 | 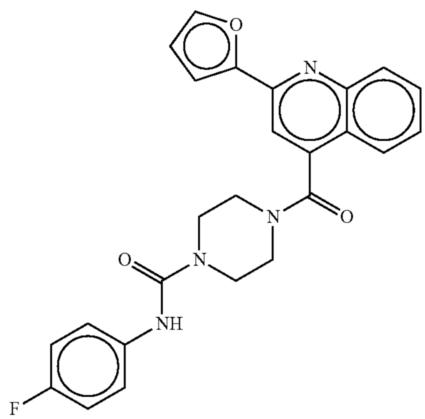 | 444.457 3.68 0 6 | UrkOrg-Synthesis PB1013640304 |
| 32 | 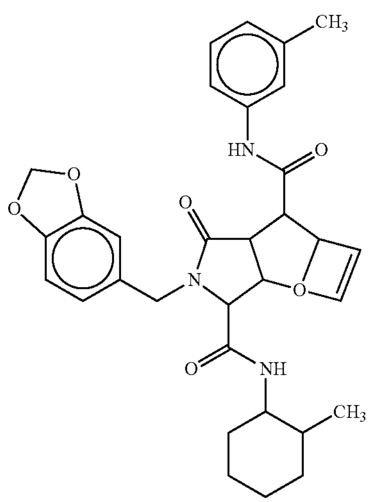 | 557.636 3.543 106.2 8 | ChemDiv C073-6425 Aldrich 30292264 |
| 33 | 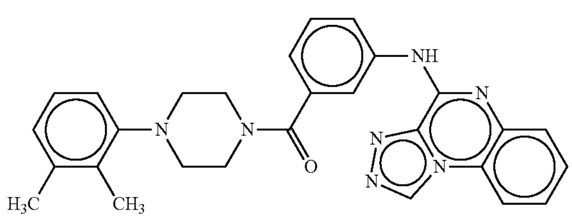 | 477.56 3.886 78.66 5 | ChemDiv C301-4018 Aldrich 61632667 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
|---|---|---|---|
| 34 | 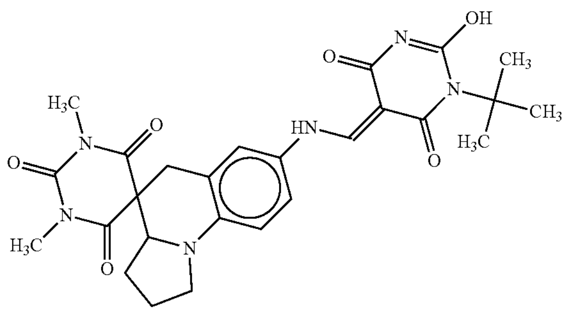 | 522.552 −0.639 142.93 1 | Vitas-M STK593537 Pharmeks PHAR119569 |
| 35 | 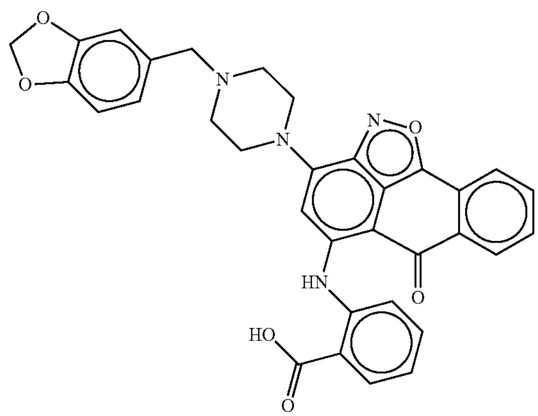 | 574.582 3.472 117.37 6 | ChemDiv C090-0436 Aldrich 30295114 |
| 36 | 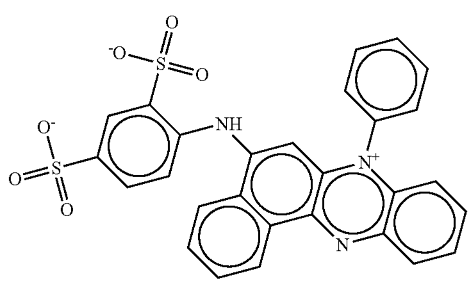 | 556.589 0.69 159.96 5 | Princeton Biomolecular Research OSSL_052610 Vita-M STK332063 ChemBridge 5222126 Aldrich 30209485 Aldrich 27890860 |
| 37 | 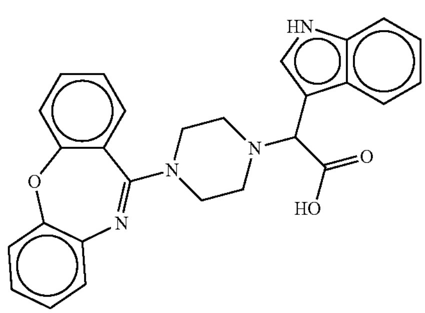 | 452.504 3.037 81.16 4 | IBScreen STOCK6S-58908 Vita-M STK642574 Aldrich 158563519 |

TABLE 1-continued

Illustrative PRODH inhibitors predicted by molecular modeling. RB is number of
rotatable bonds (estimate of flexibility), TPSA is topological polar surface area (a measure of
water solubility). MM-PBSA and Score were 0 or less for all listed compounds. MM-PBSA
is score by Molecular Dynamics - Poisson-Boltzmann Surface Area method, when calculated.
Score is the docking score produced by the algorithm; the more negative this score, the better
the predicted docking. The score was used to rank the compounds and to select the top list of
50 compounds (from a library of >1 million compounds) while also visually inspecting the
bound orientations to exclude any improperly bound candidates.

| No. | Structure | MW logP TPSA RB | Vendor Catalog No. |
|---|---|---|---|
| 38 | 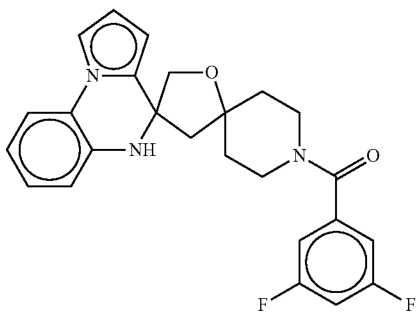 | 435.465<br>1.97<br>46.5<br>2 | Asinex<br>ADD13818439<br>Aldrich<br>332977941 |
| 39 | 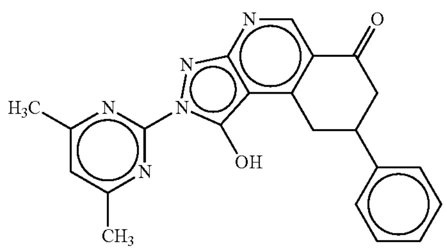 | 385.418<br>3.324<br>93.79<br>1 | Vitas-M<br>STK646137<br>Aldrich<br>161639164<br>Pharmeks<br>PHAR208762 |
| 40 | 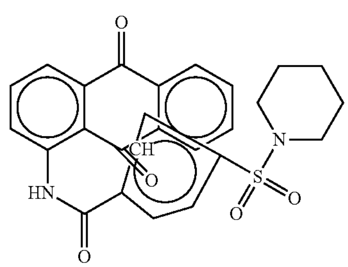 | 474.528<br>3.981<br>100.62<br>5 | ChemDiv<br>0831-0199<br>Enamine<br>T0504-3166<br>UkrOrg-<br>Synthesis<br>PB-90098771<br>Life<br>Chemicals<br>F0013-0199<br>ChemBridge<br>5916196<br>Enamine<br>Z56793324<br>Aldrich<br>27592907 |
| 41 | 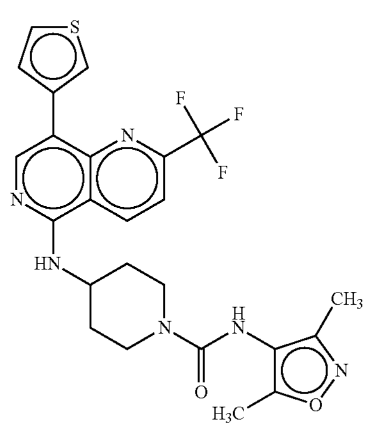 | 516.538<br>2.535<br>124.419<br>7 | Peakdale<br>Molecular<br>1015886<br>Aldrich<br>101281061 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
|---|---|---|---|
| 42 | 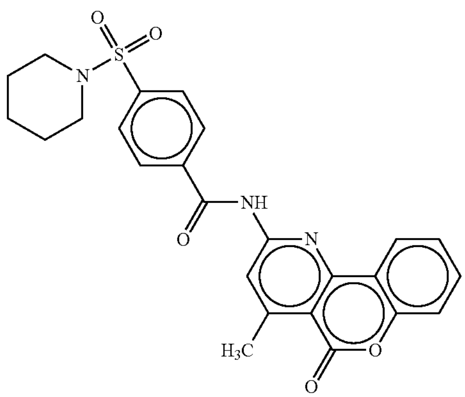 | 477.532 3.52 114.05 5 | Life Chemicals F0614-0096 Aldrich 30873114 |
| 43 | 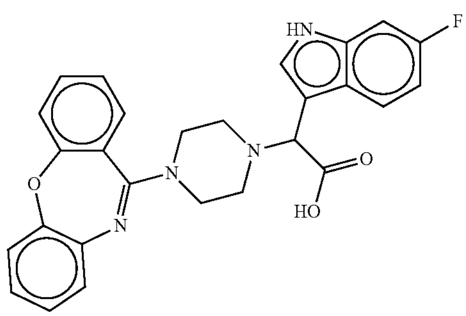 | 470.494 3.348 81.16 4 | IBScreen STOCK6S-66547 Vitas-M STK646470 Aldrich 161652115 Pharmeks PHAR219411 |
| 44 | 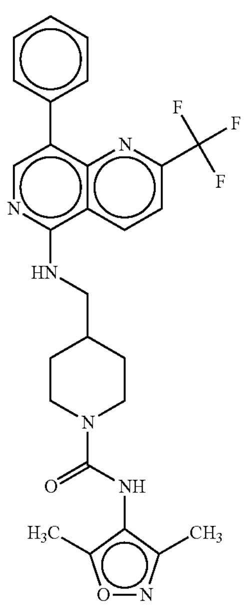 | 524.537 3.289 96.18 8 | Peakdale Molecular 1016522 Aldrich 101282614 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
|---|---|---|---|
| 45 | 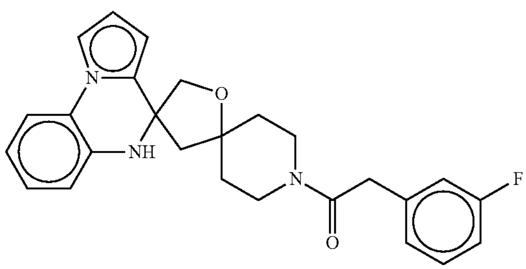 | 431.501 1.945 46.5 3 | Asinex ADD 13818444 Aldrich 332977943 |
| 46 | 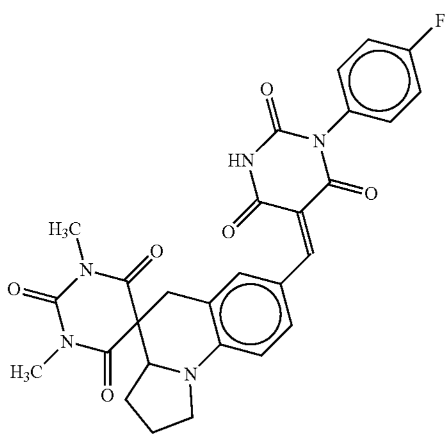 | 545.518 1.407 127.41 2 | IBScreen STOCK5S- 93439 Aldrich 48669543 |
| 47 | 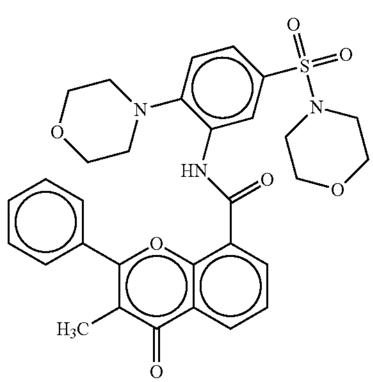 | 589.658 2.356 122.86 7 | Enamine T5275731 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
|---|---|---|---|
| 48 | 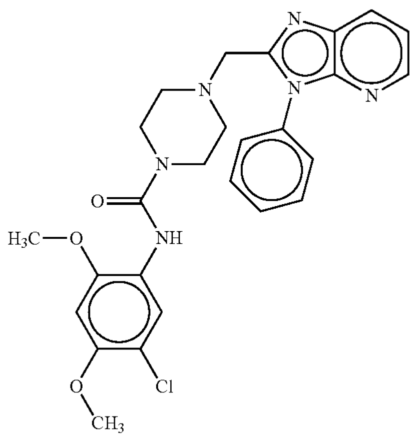 | 506.983 3.56 84.75 3 | ChemDiv G373-3280 Aldrich 117418198 |
| 49 | 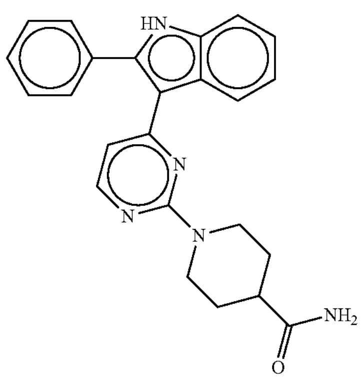 | 397.472 3.67 0 4 | Aldrich 117648873 |
| 50 | 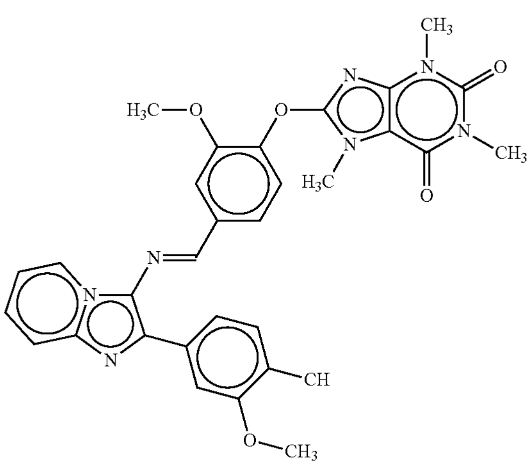 | 581.578 3.98 0 7 | Aldrich 234045784 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
|---|---|---|---|
| 51 | 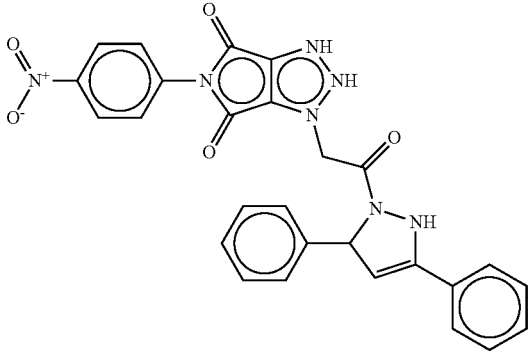 | 523.499 1.72 0 7 | Aldrich 35936878 |
| 52 | 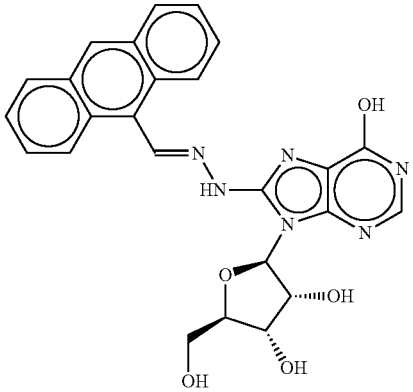 | 486.479 2.85 0 5 | Aldrich 234177489 |
| 53 | 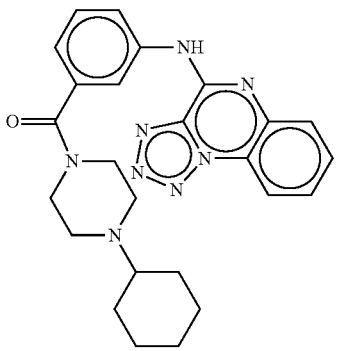 | 456.542 3.779 91.55 5 | ChemDiv C301-3490 ChemDiv C301-3947 Aldrich 61632636 Aldrich 40767028 |

TABLE 1-continued

Illustrative PRODH inhibitors predicted by molecular modeling. RB is number of rotatable bonds (estimate of flexibility), TPSA is topological polar surface area (a measure of water solubility). MM-PBSA and Score were 0 or less for all listed compounds. MM-PBSA is score by Molecular Dynamics - Poisson-Boltzmann Surface Area method, when calculated. Score is the docking score produced by the algorithm; the more negative this score, the better the predicted docking. The score was used to rank the compounds and to select the top list of 50 compounds (from a library of >1 million compounds) while also visually inspecting the bound orientations to exclude any improperly bound candidates.

| No. | Structure | MW logP TPSA RB | Vendor Catalog No. |
|---|---|---|---|
| 54 | 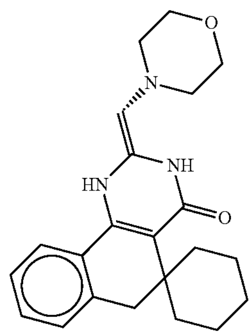 | 365.468 1.9 0 1 | Aldrich 48366905 |
| 55 | 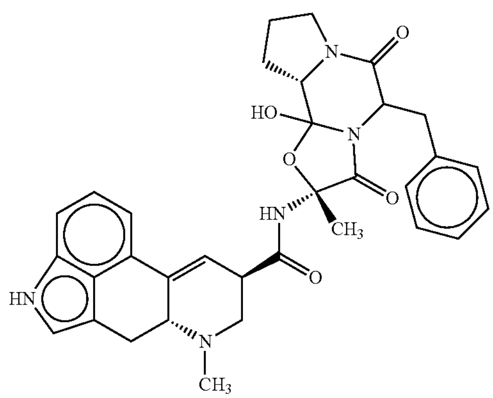 | 581.661 3.205 119.41 5 | Toronto Research Chemicals E599500 |
| 56 | 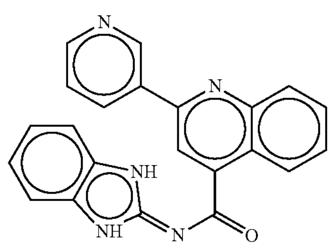 | 365.387 3.649 79.27 2 | Vitas-M STK652409 Pharmeks PHAR232526 |
| 57 | 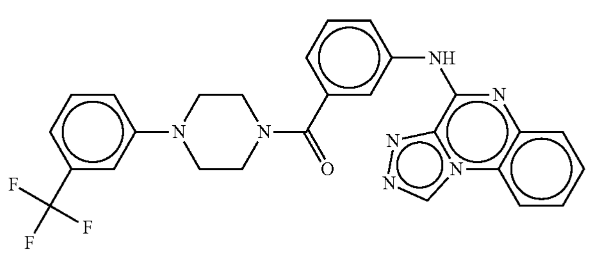 | 517.505 3.835 78.66 6 | ChemDiv C301-3950 Aldrich 61632639 |

Other means of inhibiting proline catabolism include administration of a nucleic acid inhibitor, such as an antisense nucleic acid or siRNA directed against PRODH, PC5DH, and/or GLDH.

Antisense nucleic acids (termed "antisense oligonucleotides) are accepted therapeutic modalities and many thousands of patients have been treated with antisense compounds. Efficacy and sequence specific behavior of antisense compounds in biological systems depend upon a variety of factors, which include their resistance to enzymatic degradation, binding affinity for the target, susceptibility to RNase H cleavage when bound to a target mRNA and efficiency of cellular uptake. In order to achieve the proper balance of these features for efficient modulation of target gene expression, chemical modifications are typically made to the antisense compound.

The original "first generation" antisense compounds employed in the first antisense clinical trials were oligodeoxynucleotides having 2'-deoxy ribonucleotides and phosphorothioate internucleoside linkages. Subsequently, chimeric "second generation" antisense oligonucleotides exhibited a marked improvement in potency over first generation antisense oligonucleotides. Second generation antisense oligonucleotides are chimeric oligonucleotides typically having a 2'-deoxy "gap" region flanked by "wings" having nucleotides with 2'-modified ribonucleotides, referred to as "gapmers." The most widely used of the "second generation" antisense motifs is often referred to as a "MOE gapmer" in which the 2'-modified ribonucleotide is a 2'-O-methoxyethyl (2'-MOE or simply MOE) modification, and each of the internucleotide linkages is a phosphorothioate. Predominantly, second generation oligonucleotides have a length of 20 nucleotides of which the 5 nucleotides at each terminus are 2'-MOE nucleotides and the center ten nucleotides are 2'-deoxyribonucleotides. These second generation oligonucleotides are referred to as "5-10-5 MOE gapmers" have a 5-10-5 wing-gap-wing motif. Chimeric antisense compounds with other arrangements of modifications have also been made. "Hemimers," are chimeric compounds in which there is a single 2'-modified "wing" adjacent to (on either the 5', or the 3' side of) a 2'-deoxy gap have been described (Geary et al., 2001, J. Pharm. Exp. Therap., 296, 898-904). Distribution to peripheral tissues and ultimate uptake into the cells of target organs also is important to the effectiveness of antisense compounds.

The highest concentrations of antisense compounds are typically found in the liver, kidney, spleen and lymph nodes, but can be detected in nearly all organs except for the brain (Geary et al. (2001) Curr. Opin. Investig. Drugs, 2, 562-573; Geary et al. (2001), J. Pharm. Exp. Therap., 296, 890-897).

Recently, double-stranded RNA molecules (dsRNA) have been shown to block gene expression in a highly conserved regulatory mechanism known as RNA interference (RNAi). Two types of small ribonucleic acid (RNA) molecules, microRNA (miRNA) and small interfering RNA (siRNA), are central to RNA interference. These small RNAs can bind to other specific messenger RNA (mRNA) molecules and either increase (in the case of miRNA) or decrease their activity, for example by preventing an mRNA from producing a protein. The RNAi pathway is found in many eukaryotes including animals and is initiated by the enzyme Dicer, which cleaves long double-stranded RNA (dsRNA) molecules into short double stranded fragments of ~20 nucleotide siRNAs. Each siRNA is unwound into two single-stranded (ss) ssRNAs, respectively the passenger strand and the guide strand. The passenger strand is degraded and the guide strand is incorporated into the RNA-induced silencing complex (RISC). The most well-studied outcome is post-transcriptional gene silencing, which occurs when the guide strand pairs with a complementary sequence in a messenger RNA molecule and induces cleavage by Argonaute, the catalytic component of the RISC complex. WO 99/32619 (Fire et al.) discloses the use of a dsRNA of at least 25 nucleotides in length to inhibit the expression of genes in C. elegans. dsRNA has also been shown to degrade target RNA in other organisms, including plants (see, e.g., WO 99/53050, Waterhouse et al.; and WO 99/61631, Heifetz et al.), Drosophila (see, e.g., Yang et al. (2000) Curr. Biol. 10: 1191-1200), and mammals (see WO 00/44895, Limmer; and DE 101 00 586.5, Kreutzer et al.). This natural mechanism has now become the focus for the development of pharmaceutical agents for treating disorders that are caused by the aberrant or unwanted regulation of a gene.

The design of such nucleic acid inhibitors to inhibit a particular gene of known sequence is well within the level of skill in the art. In particular, numerous online algorithms are available that generate specific oligonucleotide sequences that conform to known targeting rules, e.g., avoiding GC-rich regions, avoiding start sites, etc. Custom nucleic acid inhibitors are available from various companies including EZBiolab, Abnova, Qiagen, and others. Suitable delivery methods include liposome- or vector-mediated delivery, and the route of administration will be selected to deliver the nucleic acid inhibitor to the intended target.

p53 Restoration Therapy

A wide variety of approaches to p53 restoration are available include administration of a p53-activating drug to the subject, such as, e.g., a drug that inhibits Mdm2 or Mdmx, a drug that activates p53 directly, a drug that inhibits deacetylation of p53, a drug that inhibits nuclear export of p53. These approaches are reviewed in Lane et al., "p53-based Cancer Therapy," Cold Spring Harb Perspect Biol. 2010 September; 2(9): a001222, which is incorporated by reference herein for this description. Generally, these approaches depend on the presence of at least some p53 in the cancer cells being treated.

Various types of Mdm2 inhibitors are available and include a stapled p53-binding peptide, a nutlin, a benzodiazepinedione, and a spiro-oxindole. Illustrative Mdm2 inhibitors include MI-63, MI-219, MI-888, MI-77301/SAR405838, nutlin-3a, RG7112, RO5963, JNJ-26854165, roscovitine, flavopiridol, DRB, n-phosphonacetyl-1-aspartate PALA), pyrazofurin, and actinomycin D. Examples of direct p53 activators include CP-31398, PRIMA-1, Phi-Kan083, and RITA. Illustrative p53 deacetylation inhibitors include sirtinol, suramin, a tenovin, and 3,2',3',4'-tetrahydroxychalcone. Examples of p53 nuclear export inhibitors include leptomycin B (LMB) derivatives. Any of these drugs may be used alone or in combination with one another in the methods described herein.

p53 restoration may also be achieved using gene therapy, e.g., when the cancer cells do not contain any functional p53. A variety methods are available for transferring potentially therapeutic genes to defined cell populations (see, e.g., Mulligan, (1993) Science, 260: 926-31). These methods include: 1) Direct gene transfer (see, e.g., Wolff et al. (1990) Science 247: 1465-1468). 2) Liposome-mediated DNA transfer (see, e.g., Caplen et al. (1995) Nature Med. 3: 39-46; Crystal (1995) Nature Med. 1: 15-17; Gao and Huang (1991) Biochem. Biophys. Res. Comm., 179: 280-285, and the like). 3) Retrovirus-mediated DNA transfer (see, e.g., Kay et al. (1993) Science, 262: 117-q19; Anderson (1992) Science, 256: 808-813; and the like). 4) DNA Virus-mediated DNA transfer. Such DNA viruses include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors) (see, e.g., Ali et al. (1994) *Gene Therapy*, 1: 367-384; U.S. Pat. Nos. 4,797, 368, and 5,139,941, both incorporated herein by reference). The choice of a particular vector system for transferring the gene of interest will depend on a variety of factors. One important factor is the nature of the target cell population. Adenoviruses have the advantage that they have a broad host range and appear essentially non-oncogenic (see, e.g., Ali et al., supra.). Adenoviruses do not appear to integrate into the host genome. Because they exist extrachromosomally, the risk of insertional mutagenesis is greatly reduced (see, e.g., Ali et al., supra, p. 373). Adeno-associated viruses exhibit similar advantages as adenoviral-based vectors. However, AAVs exhibit site-specific integration on human chromosome 19 (see, e.g., Ali et al., supra, p. 377).

In addition, p53 antisense or siRNA therapy may be employed in cases of cancer characterized by a dominant negative p53 mutation. An "antisense sequence or antisense polynucleotide" is a polynucleotide that is complementary to the target polynucleotide sequence or a subsequence thereof (e.g., a p53 polynucleotide sequence). Suitable antisense molecules include, for example, polynucleotides formed from naturally-occurring bases and/or cyclofuranosyl groups joined by native phosphodiester bonds. The term "oligonucleotide" encompasses moieties that function similarly to oligonucleotides, but that have non-naturally occurring portions. Thus, oligonucleotides may have altered sugar moieties or inter-sugar linkages. Exemplary among these are the phosphorothioate and other sulfur-containing species that are known for use in the art. In accordance with some preferred embodiments, at least one of the phosphodiester bonds of the oligonucleotide has been substituted with a structure which functions to enhance the ability of the compositions to penetrate into the region of cells where the target polynucleotide whose activity is to be modulated is located. It is preferred that such substitutions comprise phosphorothioate bonds, methyl phosphonate bonds, or short-chain alkyl or cycloalkyl structures. In accordance with other preferred embodiments, the phosphodiester bonds are substituted with structures that are, at once, substantially non-ionic and non-chiral, or with structures that are chiral and enantiomerically specific. Persons of ordinary skill in the art will be able to select other linkages for use in the practice of the invention. Antisense oligonucleotides in accordance with this invention preferably comprise from about 3 to about 50 subunits (e.g., bases, in unmodified polynucleotides). It is more preferred that such oligonucleotides and analogs comprise from about 8 to about 25 subunits and still more preferred to have from about 12 to about 25 subunits.

Another approach to reducing the level of a target polynucleotide, such that encoding p53, entails RNA interference (RNAi). RNAi, also termed post-transcriptional gene silencing (PTGS), refers to a mechanism by which double-stranded (sense strand) RNA (dsRNA) specifically blocks expression of its homologous gene when injected, or otherwise introduced into cells. This approach is based on the observation that injection of antisense or sense RNA strands into *C. elegans* cells resulted in gene-specific inactivation (Guo and Kempheus (1995) *Cell* 81: 611-620). While gene inactivation by the antisense strand was expected, gene silencing by the sense strand was unexpected. Surprisingly, it was determined that the gene-specific inactivation was actually due to trace amounts of contaminating dsRNA (Fire et al. (1998) *Nature* 391: 806-811). Since then, this mode of post-transcriptional gene silencing has been demonstrated in a wide variety of organisms: plants, flies, trypanosomes, planaria, hydra, zebrafish, and mice (Zamore et al. (2000) *Cell* 101: 25-33; Gura (2000) *Nature* 404: 804-808). RNAi activity has been associated with functions as disparate as transposon-silencing, anti-viral defense mechanisms, and gene regulation (Grant (1999) *Cell* 96: 303-306). It has been shown that dsRNA is cleaved by a nuclease into 21-23-nucleotide fragments. These fragments, in turn, target the homologous region of their corresponding mRNA, hybridize, and result in a double-stranded substrate for a nuclease that degrades it into fragments of the same size (Hammond et al. (2000) *Nature* 404:293-298; Zamore et al. (2000) *Cell* 101:25-33). Although typically employed to target coding RNA (mRNA), this strategy is equally applicable to non-coding RNA.

Antisense oligonucleotides/analogs and dsRNA can be formulated and administered to cells, tissues, or organisms in accordance with standard practice.

Inhibition of Glutaminase

GLS can be inhibited in a subject by administering to the subject any pharmaceutically acceptable drug that inhibits GLS. The GLS inhibitor can be non-specific or specific for GLS1 or GLS2. Illustrative specific inhibitors of GLS1 include CB-839/Calithera, 968, BPTES, or DON. GLS inhibitors may be used alone or in combination with one another in the methods described herein. Other means of inhibiting GLS include administration of an antisense nucleic acid or siRNA directed against GLS1 or GLS2.

Induction of Tumor Hypoxia.

Figure 3:
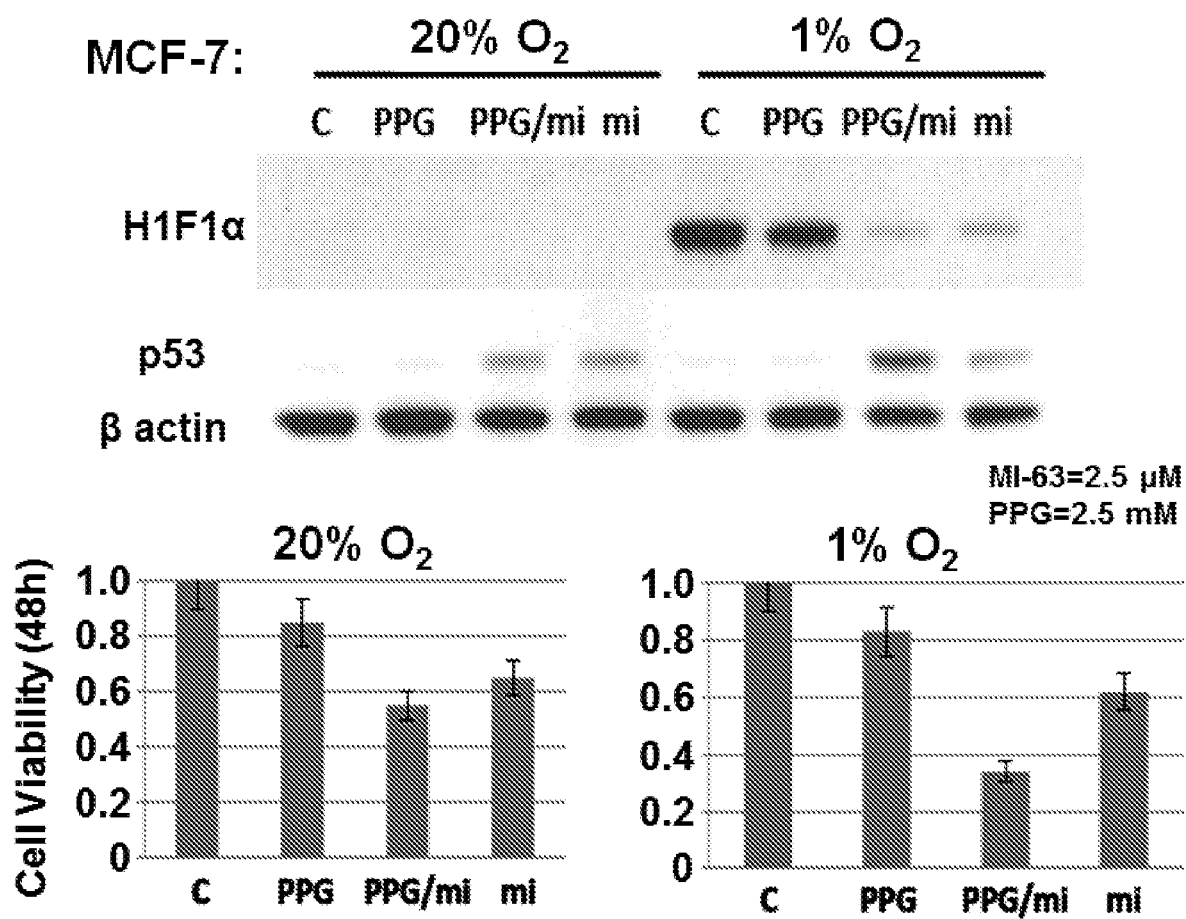
FIG. 3, illustrates that PRODH inhibition combined with hypoxia and p53 restoration increases cancer cell death.
Figure 4A:
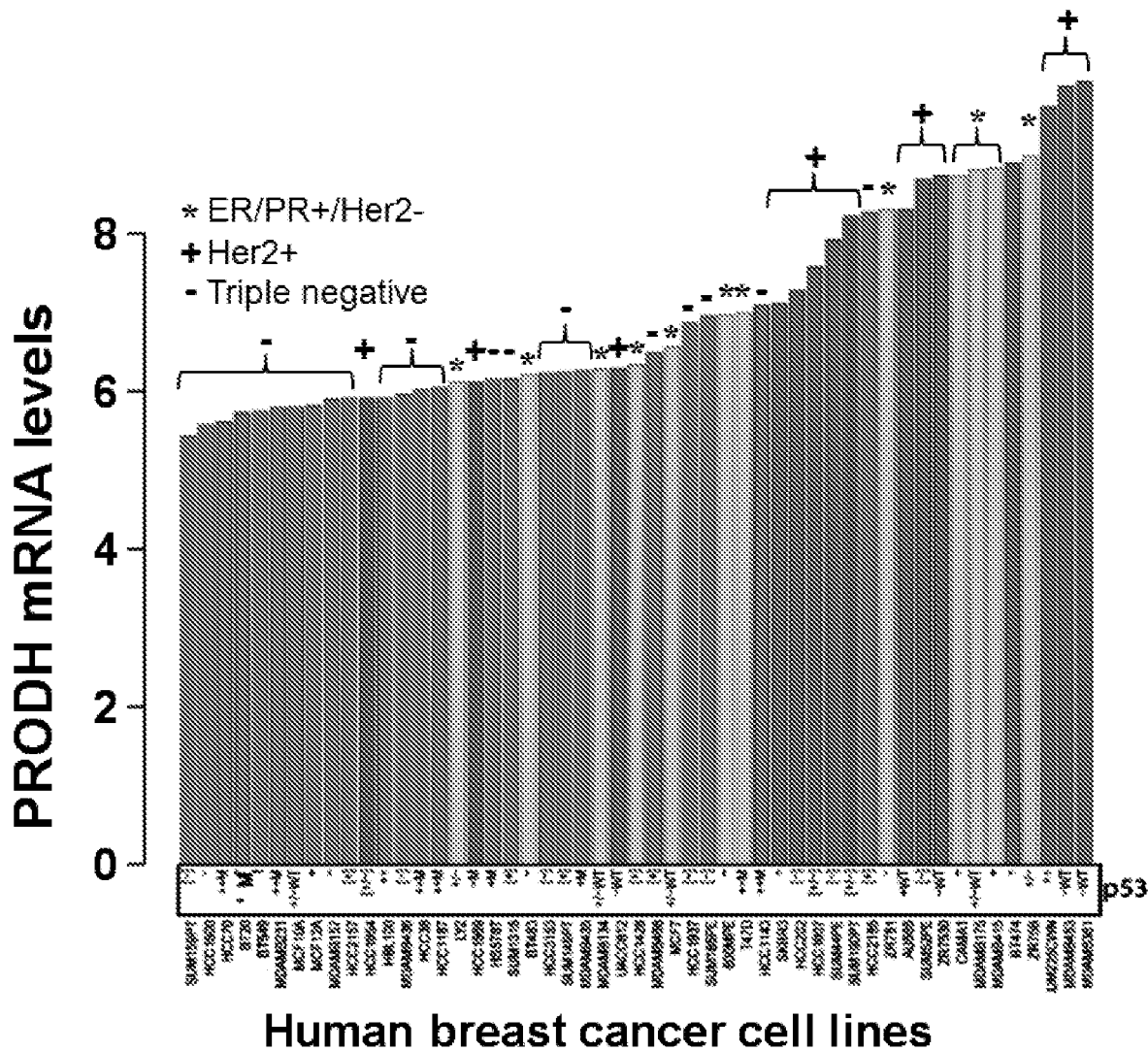
FIG. 4A-4D.
Figure 4B:
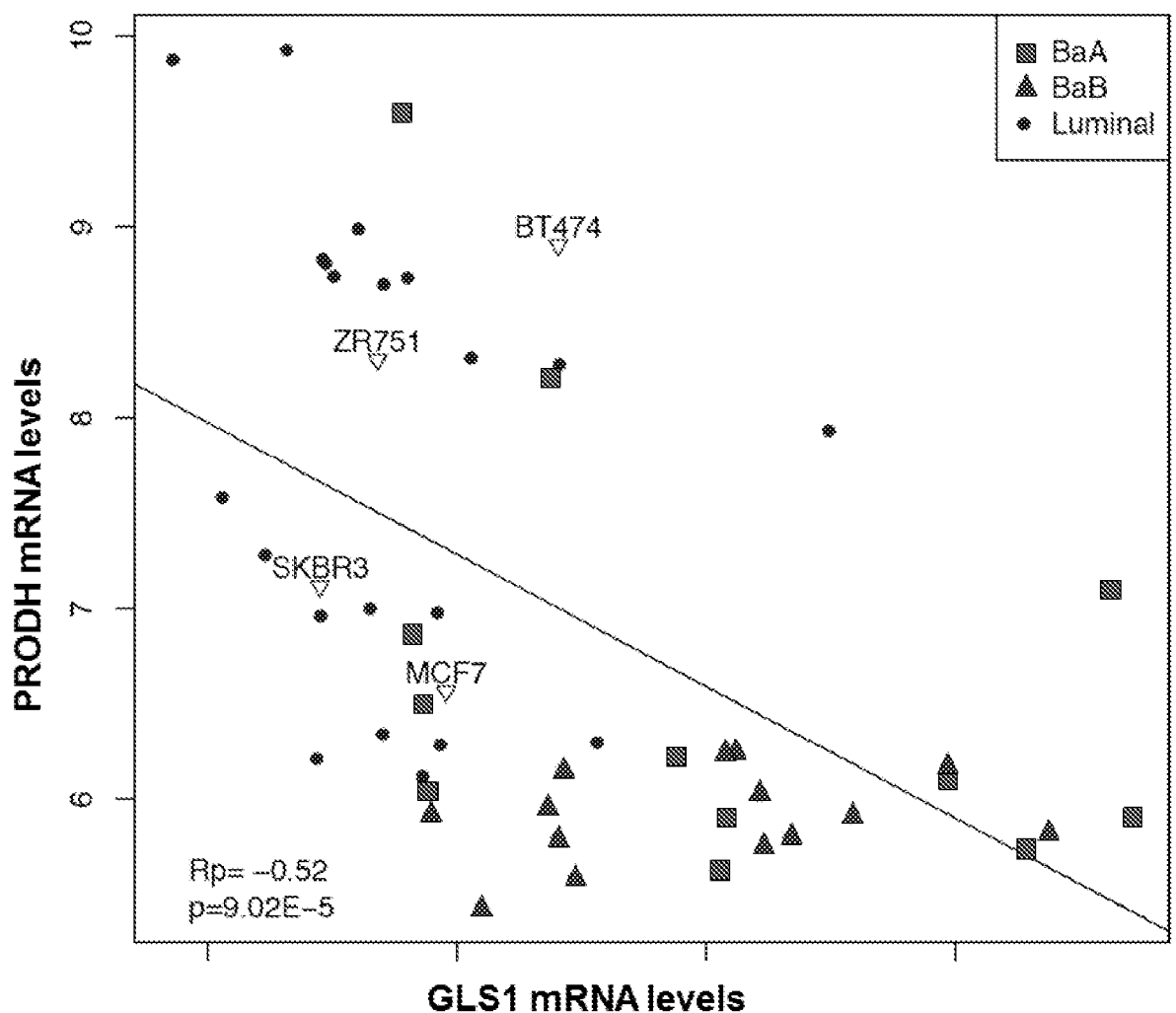
Figure 4C:
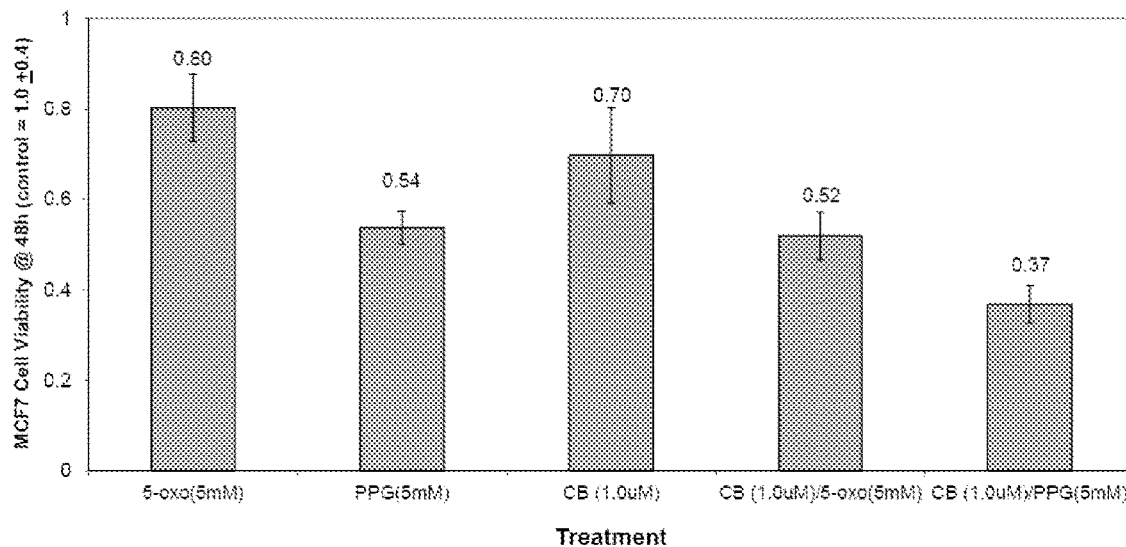
Figure 4D:
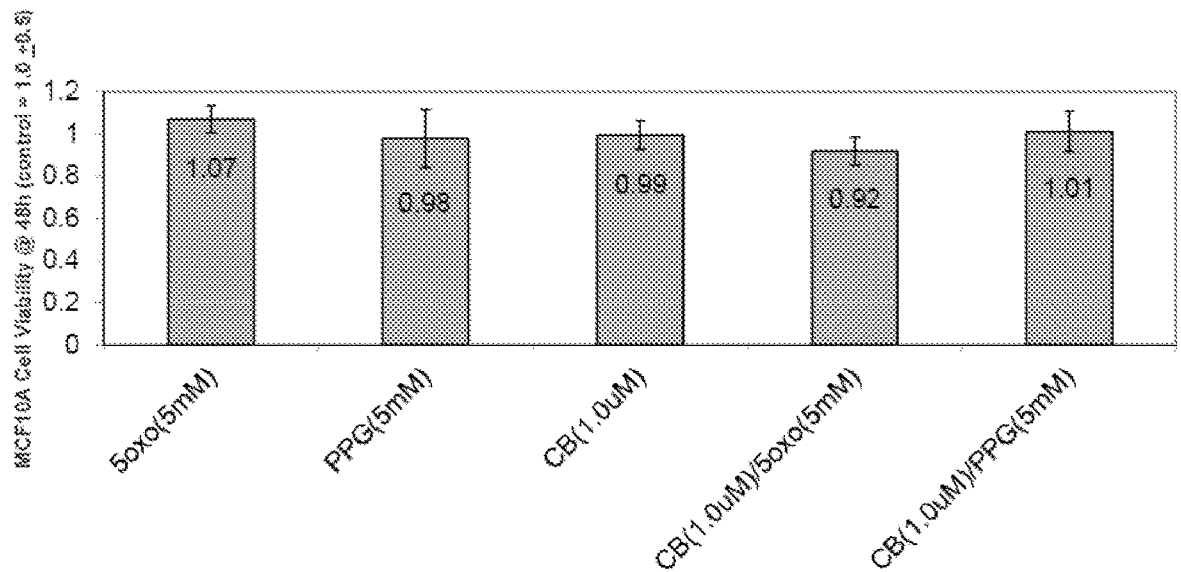

It was also discovered that inhibition of proline catabolism provides an even more striking effect in cells subject to hypoxia (see, e.g., FIG. 3). Thus, the methods are expected to prove even more effective in cancer characterized by hypoxic cells (e.g., as in a solid tumor). It is also believed that the anti-cancer effect of inhibition of proline catabolism can be improved by administration with agents that increase tumor hypoxia (e.g., anti-angiogenic drugs), optionally also in combination with p53 restoration therapy and/or inhibition of GLS.

Accordingly, in certain embodiments, the methods described herein further comprise the use of agents that increase tumor hypoxia. Illustrative agents include, but are not limited to anti-angiogenic drugs. Illustrative, but non-limiting examples of antiangiogenic drugs are shown in Table 2.

TABLE 2

Illustrative, but non-limiting anti-angiogenic therapies that can be used in combination with inhibition of proline catabolism optionally further in combination with p53 restoration and/or GLS inhibition.

| Compound | Target |
|---|---|
| Bevacizumab (AVISTIN ®) | Anti-VEGF antibody |
| Aflibercept (EYLEA ®) | VEGF-trap recombinant fusion protein of VEGF-binding domains from VEGFR |
| Ramucirumab (CYRAZMA ®) | Human monoclonal VEGFR2 antibody inhibits VEGF binding |
| Axtinib (Inlyta ®) | VEGFR1-3, PDGFRβ, and c-Kit |
| Cabozantinib (COMETRIQ ®) | VEGFR1-3, MET |
| Everolimus (AFINITOR ®) | mTOR |
| Pazopanib (VOTRIENT ®) | VEGFR1-3, PDGFR, c-KIT |
| Regorafanib (STIVARGA ®) | VEGFR1-3, PDGFRβ, TIE2 |
| Sorafenib (NEXAVAR ®) | VEGFR1-3, PDGFR, RAF |
| Suntinib (SUTENT ®) | VEGFR1-3, PDGFR, c-KIT, FLT3, RET, CSF-1R |
| Vendatanib (CAPRELSA ®) | VEGFR1-3, EGFR, RET |

Subjects and Cancers

The method described here in can be used to treat any subject susceptible to cancers that rely on the production of glutamate to fuel mitochondrial ATP production. Examples of suitable subjects include mammals, e.g., research animals or pets, such as mice, rats, guinea pigs, rabbits, cats, dogs, as well as monkeys and other primates. In certain embodiments, the subject is human.

Cancers that are amenable to treatment using the methods described herein include those that rely on the production of glutamate to fuel mitochondrial ATP production. Generally, cancers amenable to such treatment contain the proline catabolic enzyme targeted by the method, e.g., at a detectable level. In some embodiments, the cancer is tested to determine whether it contains detectable levels of PRODH, PC5DH, and/or GLDH. If PRODH, PC5DH, or GFDH is detected, the cancer can be treated by inhibiting PRODH, PC5DH, or GFDH, respectively. If two or all three of these enzymes are detected, the cancer can be treated by administering the inhibitors for the combination of enzymes detected. PRODH is the rate-limiting step for anaplerotic use of proline (commonly derived from collagen in the extracellular matrix) to generate mitochondrial ATP under nutrient stress and hypoxic conditions. Because most, if not all, cancers are expected to use this pathway, at least to some extent, its inhibition is expected to be effective, either alone or in a combination therapy described herein, against a broad range of cancers.

In certain embodiments, the cancer is a cancer known to be amenable to p53 restoration therapy, in which case, treatment can include inhibition of proline catabolism in combination with p53 restoration. As noted above, a cancer need not have any functional p53 alleles to be treatable by p53 restoration therapy; however, the presence or absence of at least one functional p53 allele will inform treatment. Therefore, in some embodiments, the cancer can be tested to determine whether it includes cells having at least one functional p53 allele. If so, the cancer can be treated. e.g., by administering a p53-reactivating drug to the subject. If not, p53 function must be provided, e.g., using gene therapy. The vast majority of human cancers are characterized by some disruption in the p53 network, and therefore, p53 restoration in combination with inhibition of proline catabolism is expected to be broadly effective.

In certain embodiments, the cancer is a cancer known to be amenable to inhibition of glutaminase (e.g., GLS1), such as one that is amenable to treatment using CB-839/Calithera, for example.

In particular embodiments in which inhibition of proline catabolism is combined with inhibition of GLS, the cancer is one that contains the proline catabolic enzyme targeted by the method as well as GLS, e.g., both at a detectable levels. In some embodiments, the cancer is tested to determine whether it contains detectable levels of GLS and, optionally to determine whether it contains detectable levels of PRODH, PC5DH, and/or GLDH. The cancer can be treated by administering the inhibitor(s) for the enzyme(s) detected.

In various embodiments, a subject treated according to one of the methods described herein has one or more of the following cancers: adrenal, anal, bile duct, bladder, bone, brain/central nervous system, breast, cervical, colon, endometrial, esophageal, eye, gallbladder, gastrointestinal, hypopharyngeal, kidney (renal cell and renal pelvis), laryngeal, leukemia, liver, lung, melanoma, lymphoma, malignant mesothelioma, multiple myeloma, nasal cavity, pancreatic, paranasal sinus, nasopharyngeal, neuroblastoma, oral cavity, oropharyngeal, osteosarcoma, ovarian, pituitary, prostate, rectal, retinoblastoma, rhabdomyosarcoma, salivary gland, sarcoma, skin (e.g., basal cell, squamous cell, melanoma), small intestine, stomach, testicular, thymus, thyroid, uterine, vaginal, and vulvar cancer.

In various embodiments, a subject treated according to one of the methods described herein has one or more of the following cancers breast cancer, prostate cancer, colon cancer, cervical cancer, ovarian cancer, pancreatic cancer, renal cell (kidney) cancer, glioblastoma, acute lymphoblastic leukemia (ALL), acute myeloid leukemia (AML), Adrenocortical carcinoma, AIDS-related cancers (e.g., kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, bronchial tumors, burkitt lymphoma, carcinoid tumors (e.g., childhood, gastrointestinal), cardiac tumors, chordoma, chronic lymphocytic leukemia (CLL), chronic myelogenous leukemia (CML), chronic myeloproliferative disorders, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CML), multiple myeloma, nasal cavity and paranasal sinus cancer, nasopharyngeal cancer, neuroblastoma, oral cavity cancer, lip and oropharyngeal cancer, osteosarcoma, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, nonmelanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and/or Wilm's tumor.

Increasing Lifespan and/or Healthspan, and/or Reducing Stress.

As explained above, in addition to the discovery that sustained and full inhibition of proline catabolism (e.g. PRODH) induces cancer cell (but not normal cell) apoptosis offering a new cancer therapeutic strategy, it was also a surprising discovery that appropriately timed and transient (hermetic) dosing with an irreversible ("suicide") inhibitor of PRODH can also activate lifespan- and healthspan-inducing mitohormesis in a normal organism increasing its resistance to stress and disease and significantly enhancing its median and overall lifespan.

Accordingly in certain embodiments, methods of increasing lifespan (e.g., as indicated by an increase/improvement in one or more measures/indicators of lifespan) and/or methods of increasing healthspan (e.g., as indicated by an increase/improvement in one or more measures/indicators of healthspan), and/or methods of reducing the physiological stress response (e.g., as indicated by an increase/improvement in one or more measures of physiological stress) are provided where the methods comprise treating the subject with a therapy comprising inhibition of proline catabolism, e.g., as described above.

Because the therapeutic agents described herein (e.g., PRODH inhibitors) are used prophylactically (e.g., to increase healthspan, to increase lifespan, to reduce stress) the therapeutic agents are typically administered in more than one dose and typically over a prolonged period of time (e.g., at least 1 month, at least 6 months, or at least 1 year, or at least 2 years, or at least 5 years, or at least 10 years, or at least 20 years, or at least 40 years, or at least 60 years). In particular embodiments, the methods improve one or more measures of life span and/or health span ("life/health span") at least about 5, 10 15, 20 25, 30 35, 40 45, 50, 55, 60, 65, 70, 75, 80, 85, 90, 95 percent or more, relative to the condition of the subject before treatment or relative to a control population.

Any suitable measure of life/health span can be employed in the methods described herein. In certain embodiments, an improvement in life span and/or health span can be detected as a reduction in frailty, an improvement in function in an age-related disability, the mitigation of a symptom of an age-related disease, and/or a delay in onset of frailty, age-related disability, or age-related disease, relative to the condition of the subject before administration of a compound described here or relative to a control population. For example, a reduction in frailty, an improvement in function in an age-related disability, the mitigation of a symptom of an age-related disease can be measured with reference to the pre-treatment condition of the subject or relative to a control population. Delay in onset of frailty, age-related disability, or age-related disease is typically measured with reference to a control population.

An improvement (i.e., a reduction) in frailty can be measured as increased strength, weight gain, faster mobility, increased energy, increased levels of activity, increased endurance, and/or enhanced behavioral response to a sensory cue. Alternatively or in addition, a decrease in one or more inflammatory biomarkers, an improvement in glucose homeostasis, and a decrease in one of more biomarkers of clotting activation can indicate a reduction in frailty.

The mitigation of a symptom of an age-related disease, such as osteoporosis, arthritis, cataracts, macular degeneration, and cardiovascular disease, can also indicate an improvement in a measure of life/health span in the methods described herein. For example, one or more cardiovascular parameters, such as cholesterol level, triglyceride level, high density lipoprotein level, and/or blood pressure can be measured as an indicator of life/health span.

In particular embodiments, an improvement in a measure of life/health span can be detected as a reduction in, a reversal of, or delay in onset of sarcopenia, relative to the condition of the subject before treatment or relative to a control population. More specifically, reduction and/or reversal of sarcopenia can be measured with reference to the pre-treatment condition of the subject or relative to a control population; whereas delay in onset of sarcopenia is typically measured with reference to a control population.

In certain embodiments, an improvement in a measure of life/health span can be detected as reduction in, a reversal of, or delay in onset of an age-related increase in lipofuscin accumulation, relative to the condition of the subject before administration of a compound described herein or relative to a control population. In particular, reduction and/or reversal of sarcopenia can be measured with reference to the pre-treatment condition of the subject or relative to a control population; whereas delay in onset of excess liposfuscin is typically measured with reference to a control population. Illustrative tissues in which in which lipofuscin accumulated and can be measured include brain, heart, liver, spleen, and kidney.

Alternatively or in addition, improved life/health span can be detected by detecting an enhanced ability to maintain homeostasis during the application of a stressor and/or a reduced time required to return to homeostasis after the application of a stressor. For example, responses to stressors including drug-induced oxidative stress, exposure to heat, and exposure to cold can be measured to determine whether the subject has an enhanced ability to maintain and/or return to homeostasis after being stressed.

In particular embodiments, the measure of life/health span includes the level and/or activity of a molecule that plays a role in protein trafficking, the autophagy pathway, ubiquitination, and/or lysozomal degradation of proteins. An example of the latter is lysosome-associated membrane protein-2 (LAMP-2).

Other indicators of life/health span can include the number of inclusion bodies in muscle tissue, and/or mitochondrial function and/or morphology.

Similarly, any suitable measure of reduction in physiological stress can be used as a measure for the methods of reducing the physiological stress response described herein. Such measures include, but are not limited to cortisol level, cortisol/DHEA ratio, Th1 immunity activity (NK cells, killer T cells), catecholamine levels, chromogranin A levels, free radicals or reactive oxygen species, N-acetylaspartate levels, expression of heat shock proteins, and the like.

The methods method of increasing a measure of lifespan and/or healthspan described herein are typically carried out using subject who is suffering from, or determined to be at risk for a decline in a measure of life/health span. Thus for example, these methods can be performed on a subject suffering from, or determined to be at risk for, frailty, an age-related disability, or an age-related disease. In various embodiments, where the subject is suffering from, or determined to be at risk for, frailty, the subject is determined to have at least two, three, four, five, six, or seven symptoms selected: weakness, weight loss, slowed mobility, fatigue, low levels of activity, poor endurance, and impaired behavioral response to a sensory cue. Alternatively or in addition, the subject may have one or more symptoms selected from an increase in one or more inflammatory biomarkers, glucose homeostasis impairment, and an increase in one of more biomarkers of clotting activation.

In particular embodiments, the subject is suffering from sarcopenia and/or has lipofuscin accumulation in one or more of brain, heart, liver, spleen, and kidney. Alternatively or in addition, the subject may have a reduced ability to maintain homeostasis during the application of a stressor and/or may require an extended time required to return to homeostasis after the application of a stressor. In such embodiments, the reduced ability or extended time is relative to the condition of the subject at a previous time or relative to a normal ability or time.

In particular embodiments, the subject may display an abnormal level and/or activity of a molecule that plays a role in protein trafficking, the autophagy pathway, ubiquitination, and/or lysozomal degradation of proteins (e.g., LAMP-2). Alternatively or in addition, the subject may have abnormal inclusion bodies in muscle tissue and/or an abnormality in mitochondrial function and/or morphology. Such changes may be observed relative to the condition of the subject at a previous time or relative to a normal (e.g., non-aged adult) subject.

Pharmaceutical Formulations and Administration

Pharmaceutical Formulations.

The agents administered in any of the therapies described above (the "active agents") will typically be formulated according standard practice. In some embodiments, a pharmaceutical formulation including a novel PPG analog and a pharmaceutically acceptable carrier is provided. In certain particular embodiments, a combined formulation that includes a drug that inhibits proline catabolism, and either a drug that promotes p53 restoration or a drug that inhibits glutaminase (GLS), or both is provided. Such formulations can readily be prepared where all drugs can be administered by the same route of administration.

The active agent(s) can be administered in the "native" form or, if desired, in the form of salts, esters, amides, prodrugs, derivatives, and the like, provided the salt, ester, amide, prodrug, or derivative is suitable pharmacologically, i.e., effective in the present method. Salts, esters, amides, prodrugs, and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Pharmaceutically acceptable salts of the active agents include those derived from pharmaceutically acceptable, inorganic and organic acids and bases. Examples of suitable acids include hydrochloric, hydrobromic, sulfuric, nitric, perchloric, fumaric, maleic, phosphoric, glycollic, lactic, salicyclic, succinic, gluconic, isethionic, glycinic, malic, mucoic, glutammic, sulphamic, ascorbic acid; toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to alkali such as sodium and ammonium.

For example, acid addition salts are prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Illustrative acid addition salts of the active agents herein are halide salts, such as may be prepared using hydrochloric or hydrobromic acids. Conversely, basic salts of the active agents described herein are prepared in a similar manner using a pharmaceutically acceptable base such as sodium hydroxide, potassium hydroxide, ammonium hydroxide, calcium hydroxide, trimethylamine, or the like. Illustrative basic salts include alkali metal salts, e.g., the sodium salt, and copper salts.

Acid addition salts useful in the methods described herein include the physiologically compatible acid addition salts, most preferably the dihydrochloride. Bis-quaternary salts useful in the methods described herein include the physiologically compatible bis-quaternary salts, such as the methiodide and the dimethiodide.

Preparation of esters typically involves functionalization of hydroxyl and/or carboxyl groups and/or other reactive groups that may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The active agents described herein are typically combined with a pharmaceutically acceptable carrier (excipient), such as are described in Remington's Pharmaceutical Sciences (1980) 16th editions, Osol, ed., 1980. Pharmaceutically acceptable carriers can contain one or more physiologically acceptable compound(s) that act, for example, to stabilize the composition or to increase or decrease the absorption of the active agent(s). A pharmaceutically acceptable carrier suitable for use in the methods described herein is non-toxic to cells, tissues, or subjects at the dosages employed, and can include a buffer (such as a phosphate buffer, citrate buffer, and buffers made from other organic acids), an antioxidant (e.g., ascorbic acid), a low-molecular weight (less than about 10 residues) peptide, a polypeptide (such as serum albumin, gelatin, and an immunoglobulin), a hydrophilic polymer (such as polyvinylpyrrolidone), an amino acid (such as glycine, glutamine, asparagine, arginine, and/or lysine), a monosaccharide, a disaccharide, and/or other carbohydrates (including glucose, mannose, and dextrins), a chelating agent (e.g., ethylenediaminetetratacetic acid (EDTA)), a sugar alcohol (such as mannitol and sorbitol), a salt-forming counterion (e.g., sodium), and/or an anionic surfactant (such as TWEEN™ PLURONICS™, and PEG). In one embodiment, the pharmaceutically acceptable carrier is an aqueous pH-buffered solution.

Other pharmaceutically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

Pharmaceutical formulations described herein can be stored in any standard form, including, e.g., an aqueous solution or a lyophilized cake. Such compositions are typically sterile when administered to subjects. Sterilization of an aqueous solution is readily accomplished by filtration through a sterile filtration membrane. If the composition is stored in lyophilized form, the composition can be filtered before or after lyophilization and reconstitution.

When active agents described herein contain chiral or prochiral centres they can exist in different stereoisomeric forms including enantiomers of (+) and (−) type or mixtures of them. The use of either the individual isomers or the mixtures thereof is contemplated herein.

It will be understood that, when mixtures of optical isomers are present, they may be separated according to the classic resolution methods based on their different physico-chemical properties, e.g. by fractional crystallization of their acid addition salts with a suitable optically active acid or by the chromatographic separation with a suitable mixture of solvents.

Administration

The active agents described herein (e.g., inhibitors of Proline catabolism) can be administered by any convenient route of administration. Where multiple active agents (e.g., a PRODH inhibitor and a p53 restoration agent, and/or a glutaminase inhibitor), are to be administered the different agents may be administered by the same or different routes of administration at the same or at different times as required for the active agents. Where possible, it is generally desirable to administer these multiple agents by the same route of administration, preferably in the same formulation. However, differences in pharmacodynamics, pharmacokinetics, or other considerations may dictate the co-administration of selected compound and additional agent in separate formulations.

In various embodiments, active agents identified can be administered by intravenous, intraarterial, intrathecal, intradermal, intracavitary, oral, rectal, intramuscular, subcutaneous, intracisternal, intravaginal, intraperitonial, topical, buccal, and/or nasal routes of administration. In various embodiments, the active agents described herein can be administered orally, in which case delivery can be enhanced by the use of protective excipients. This is typically accomplished either by complexing the active agent(s) with a composition to render them resistant to acidic and enzymatic hydrolysis or by packaging the agents in an appropriately resistant carrier, e.g. a liposome. Means of protecting agents for oral delivery are well known in the art (see, e.g., U.S. Pat. No. 5,391,377).

Elevated serum half-life can be maintained by the use of sustained-release "packaging" systems. Such sustained release systems are well known to those of skill in the art (see, e.g., Tracy (1998) *Biotechnol. Prog.* 14: 108; Johnson et al. (1996), *Nature Med.* 2: 795; Herbert et al. (1998), *Pharmaceut. Res.* 15, 357).

Suitable pharmaceutical formulations can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, lipid complexes, etc. In another embodiment, one or more components of a solution can be provided as a "concentrate," e.g., in a storage container (e.g., in a premeasured volume) ready for dilution or in a soluble capsule ready for addition to a volume of water.

Other illustrative formulations for topical delivery include, but are not limited to, ointments and creams. Ointments are semisolid preparations, which are typically based on petrolatum or other petroleum derivatives. Creams containing the selected active agent, are typically viscous liquid or semisolid emulsions, often either oil-in-water or water-in-oil. Cream bases are typically water-washable and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base is preferably inert, stable, nonirritating, and nonsensitizing.

In certain embodiments, the agents may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

In certain embodiments, one or more active agents described herein are administered alone or in combination with other therapeutics in implantable (e.g., subcutaneous) matrices, termed "depot formulations."

A major problem with standard drug dosing is that typical delivery of drugs results in a quick burst of medication at the time of dosing, followed by a rapid loss of the drug from the body. Most of the side effects of a drug occur during the burst phase of its release into the bloodstream. Secondly, the time the drug is in the bloodstream at therapeutic levels is very short; most is used and cleared during the short burst.

Drugs (e.g., the active agents described herein) imbedded in various matrix materials for sustained release can mitigate these problems. Drugs embedded, for example, in polymer beads or in polymer wafers have several advantages. First, most systems allow slow release of the drug, thus creating a continuous dosing of the body with small levels of drug. This typically prevents side effects associated with high burst levels of normal injected or pill-based drugs. Secondly, since these polymers can be made to release over hours to months, the therapeutic span of the drug is markedly increased. Often, by mixing different ratios of the same polymer components, polymers of different degradation rates can be made, allowing remarkable flexibility depending on the agent being used. A long rate of drug release is beneficial for people who might have trouble staying on regular dosage, such as the elderly, but also represents an ease of use improvement that everyone can appreciate. Most polymers can be made to degrade and be cleared by the body over time, so they will not remain in the body after the therapeutic interval.

Another advantage of polymer-based drug delivery is that the polymers often can stabilize or solubilize proteins, peptides, and other large molecules that would otherwise be unusable as medications. Finally, many drug/polymer mixes can be placed directly in the disease area, allowing specific targeting of the medication where it is needed without losing drug to the "first pass" effect. This is certainly effective for treating the brain, which is often deprived of medicines that can't penetrate the blood/brain barrier.

A wide variety of approaches to designing depot formulations that provide sustained release of an active agent are known and are suitable for use in the methods described herein. Generally, the components of such formulations are biocompatible and may be biodegradable. Biocompatible polymeric materials have been used extensively in therapeutic drug delivery and medical implant applications to effect a localized and sustained release (see, e.g., Leong et al. (1987) *Adv. Drug Deliv. Rev.*, 1:199-233; Langer (1990) *Science*, 249: 1527-1533; and the like). Such delivery systems offer the potential of enhanced therapeutic efficacy and reduced overall toxicity.

Examples of classes of synthetic polymers that have been studied as possible solid biodegradable materials include polyesters (Pitt et al., "Biodegradable Drug Delivery Systems Based on Aliphatic Polyesters: Applications to Contraceptives and Narcotic Antagonists," Controlled Release of Bioactive Materials, 19-44 (Richard Baker ed. (1980); Poly(amino acids) and pseudo-poly(amino acids) (Pulapura et al. (1992) *J. Biomaterials Appl.*, 6(1): 216-250); polyurethanes (Bruin et al. (1990) *Biomaterials*, 11(4): 291-295); polyorthoesters (Heller et al. (1981) *Polymer Engineering Sci.*, 21(11): 727-731); and polyanhydrides (Leong et al. (1986) *Biomaterials* 7(5): 364-371).

Thus, for example, the active agent(s) can be incorporated into a biocompatible polymeric composition and formed into the desired shape outside the body. This solid implant is then typically inserted into the body of the subject through an incision. Alternatively, small discrete particles composed of these polymeric compositions can be injected into the body, e.g., using a syringe. In an illustrative embodiment, the active agent(s) can be encapsulated in microspheres of poly (D,L-lactide) polymer suspended in a diluent of water, mannitol, carboxymethyl-cellulose, and polysorbate 80. The polylactide polymer is gradually metabolized to carbon dioxide and water, releasing the active agent(s) into the system.

In yet another approach, depot formulations can be injected via syringe as a liquid polymeric composition. Liquid polymeric compositions useful for biodegradable controlled release drug delivery systems are described, e.g., in U.S. Pat. Nos. 4,938,763; 5,702,716; 5,744,153; 5,990, 194; and 5,324,519. After injection in a liquid state or, alternatively, as a solution, the composition coagulates into a solid.

One type of polymeric composition suitable for this application includes a nonreactive thermoplastic polymer or copolymer dissolved in a body fluid-dispersible solvent. This polymeric solution is placed into the body where the polymer congeals or precipitates and solidifies upon the dissipation or diffusion of the solvent into the surrounding body tissues. See, e.g., Dunn et al., U.S. Pat. Nos. 5,278,201; 5,278,202; and 5,340,849 (disclosing a thermoplastic drug delivery system in which a solid, linear-chain, biodegradable polymer or copolymer is dissolved in a solvent to form a liquid solution).

In certain embodiments the active agent(s) can also be adsorbed onto a membrane, such as a silastic membrane, which can be implanted, as described in International Publication No. WO 91/04014. Other illustrative implantable sustained release systems include, but are not limited to Re-Gel®, SQ2Gel®, and Oligosphere® by MacroMed, Pro-Lease® and Medisorb® by Alkermes, Paclimer® and Gliadel® Wafer by Guilford pharmaceuticals, the Duros implant by Alza, acoustic biSpheres by Point Biomedical, the Intelsite capsule by Scintipharma, Inc., and the like.

Dose

In therapeutic applications, one or more of the active agents described herein is/are administered to a subject in an amount sufficient to inhibit cancer growth and/or cause tumor necrosis. In some embodiments, the amount employed is sufficient to cause preferential apoptosis of cancer cells, as compared to normal, non-cancerous cells. Amounts effective for this use may depend upon disease status, the degree of improvement sought, and the general state of the subject's health. Single or multiple administrations of the active agent(s) may be administered depending on the dosage and frequency as required and tolerated by the subject.

The concentration of active agent(s) can vary widely and will be selected primarily based on fluid volumes, viscosities, body weight and the like in accordance with the particular mode of administration selected and the subject's needs. In accordance with standard practice, the clinician can titer the dosage and modify the route of administration as required to obtain the optimal therapeutic effect. Generally, the clinician begins with a low dose and increases the dosage until the desired therapeutic effect is achieved.

Starting doses for a given active agent can, for example be extrapolated from in vitro and/or animal data.

In particular embodiments, concentrations of active agent(s) will typically be selected to provide dosages ranging from about 0.0001 µg/kg/day to about 10 mg/kg/day and sometimes higher. Typical dosages range from about 0.001 µg/kg/day to about 1 mg/kg/day, specifically from about 0.01 µg/kg/day to about 100 µg/kg/day, more specifically from about 0.1 µg/kg/day to about 10 µg/kg/day, e.g., about 1 µg/kg/day. It will be appreciated that such dosages may be varied to optimize a therapeutic regimen in a particular subject or group of subjects, and thus any of these values can represent the upper or lower limit of a suitable dosage range (e.g., about 0.001 µg/kg to about 10 µg/kg).

Assaying PRODH to Determine Responders/Non-Responders to Inhibition of Proline Catabolism/GLS Assay Methods.

In certain embodiments, methods method for determining whether a subject with cancer is a candidate for a cancer treatment method including inhibition of proline catabolism or inhibition of glutaminase (GSL) are provided. In certain embodiments, the methods entail assaying a sample of the cancer for proline dehydrogenase (PRODH) level, and if PRODH is elevated relative to a normal level, identifying the subject as one who is a candidate for a cancer treatment method including inhibition of proline catabolism (e.g., as described above) and/or as one who is likely to have a reduced response to a cancer treatment method consisting of inhibition of GLS1 alone. If PRODH is not elevated relative to a normal level, the method entails, in some embodiments, identifying the subject as one who is a candidate for a cancer treatment method including inhibition of GLS, alone or in combination with another therapy. Normal PRODH levels may vary depending upon the cell or tissue, developmental stage, exposure to stimuli, etc. PRODH has been found to be undetectable in the normal breast tissue assayed. Therefore, in certain particular embodiments, the detection of PRODH in a breast tissue sample (e.g., a tumor biopsy) would qualify as "elevated."

In various embodiments, the method additionally includes assaying the sample for one or more of: P5C dehydrogenase (PC5DH), glutamate dehydrogenase (GLDH), P5C reductase-1 (PYCR1). The presence and/or level of these enzymes can be used to assess the likelihood of success of a proposed strategy for proline inhibition and/or to design a more effective inhibition strategy, e.g., one that entails inhibiting multiple proline catabolic enzymes.

In certain particular embodiments, the methods can additionally entail testing a sample of the cancer to determine whether cancer cells include at least one functional p53 allele. If the cancer cells are determined to include at least one functional p53 allele, in some embodiments, the subject is identified as one who is a candidate for a p53 restoration therapy, e.g., that includes administration of a p-53-activating drug. Alternatively, if the cancer cells are determined to include no functional p53 alleles, in some embodiments, the subject is identified as one who is not a candidate for administration of a p53-reactivating drug, but is a candidate for a gene therapy aimed at providing p53 function. Several approaches have been developed for detection and analyses of p53 allele status, any of which can be employed in the present context. For example, immunoassays have been developed to detect p53 protein levels, molecular analyses are used to detect changes in DNA structure or sequence, and functional assays are used to examine p53 activity. Functional analysis of separated alleles in yeast targets the transactivation capability of the p53 protein expressed in yeast cells. This method uses p53 mRNA isolated from cells and tissues to produce a p53 product by RT-PCR. These approaches are reviewed in Smardová J, et al., "Functional analysis of p53 tumor suppressor in yeast," Differentiation. 2005 July; 73(6):261-77.

The methods can also, optionally, entail assaying the sample for GLS level, and, if GLS is elevated relative to a normal level, identifying the subject as one who is a candidate for a cancer treatment method including inhibition of GLS and/or as one who is likely to have a reduced response to a cancer therapy consisting of inhibition of proline catabolism alone. If GLS is not elevated relative to a normal level, the method entails, in some embodiments, identifying the subject as one who is a candidate for a cancer treatment method including inhibition of proline catabolism. Humans express to glutaminase isozymes: GLS1 and GLS2. In various embodiments, the GLS assay may be non-specific (i.e., may detect any isozyme present) or may be specific for GLS1 or GLS2. GLS2 is found in the mitochondria and can play a role in generating mitochondrial ATP needed by cancer cells. Accordingly, in some embodiments, GLS2 levels may be most informative in the context of the methods described herein.

Sample Collection and Processing

The assay methods described herein are generally carried out on biological samples that include or consist of one or more cancer cells derived from an animal, preferably a mammal, and more preferably a human. In various embodiments, the biological sample can be a biopsy, such as a fine needle aspirate, core biopsy, excisional or incisional biopsy, endoscopic biopsy, laparoscopic, thoracoscopic or mediastinoscopic biopsy, laparotomy or thoracotomy, or skin biopsy. Biopsies may be taken of any of the tissues affected by any of the cancers discussed above. Alternatively, or in addition, the biological sample can be a sample of a bodily fluid, e.g., blood or blood fraction (e.g., serum or plasma), lymph, cerebrospinal fluid, peritoneal fluid, pleural fluid, oral fluid, and urine.

The sample may be pretreated as necessary by dilution in an appropriate buffer solution or concentrated, if desired. Any of a number of standard aqueous buffer solutions and/or protease inhibitors, employing any of a variety of buffers, such as phosphate, Tris, or the like, at physiological pH, can be used.

In some embodiments, sample preparation may include the isolation of single cells (e.g., a population of cells obtained from a biological sample, as described above), followed by assay of each cell individually. In some embodiments, single cells are lysed and their contents analyzed in a manner that permits a determination of the level(s) of one or more analyte(s) in each cell.

Assaying Enzyme Expression and/or Activity Levels

The enzymes described above can be detected and quantified by any of a number of methods well known to those of skill in the art of polypeptide or NADH detection. These may include analytic biochemical methods such as electrophoresis, capillary electrophoresis, high performance liquid chromatography (HPLC), thin layer chromatography (TLC), hyperdiffusion chromatography, mass spectroscopy and the like, or various immunological methods such as fluid or gel precipitin reactions, immunodiffusion (single or double), immunohistochemistry, affinity chromatography, immunoelectrophoresis, radioimmunoassay (RIA), enzyme-linked immunosorbent assays (ELISAs), immunofluorescent assays, Western blotting, and the like.

The forgoing detect the amount of enzyme present by detecting the level of the polypeptide itself. Enzyme presence and/or amount can also be determined in an enzymatic activity assay that measures either the consumption of substrate or production of product over time. Such assays can be continuous or discontinuous. Illustrative continuous assays include spectrophotometric, fluorometric, calorimetric, chemiluminescent, light scattering, and microscale thermophoresis methods. Illustrative discontinuous assays included radiometric and chromatographic methods. The substrates and products of the enzymes described herein are known and provide a basis for designing activity-based assays for any of these enzymes.

Immunoassays

In certain embodiments, the enzyme of interest is detected and/or quantified in the biological sample using any of a number of well-known immunoassays (see, e.g., U.S. Pat. Nos. 4,366,241; 4,376,110; 4,517,288; and 4,837,168). For a general review of immunoassays, see also Methods in Cell Biology Volume 37: Antibodies in Cell Biology, Asai, ed. Academic Press, Inc. New York (1993); Basic and Clinical Immunology 7th Edition, Stites & Terr, eds. (1991).

Conventional immunoassays often utilize a "capture agent" to specifically bind to and often immobilize the analyte on a solid phase. In preferred embodiments, the capture agent is an antibody.

Immunoassays also typically utilize a labeled detection agent to specifically bind to and label the binding complex formed by the capture agent and the analyte. The labeled detection agent may itself be one of the moieties making up the antibody/analyte complex. Alternatively, the labeled detection agent may be a third moiety, such as another antibody, that specifically binds to the capture agent/analyte complex. Other polypeptides capable of specifically binding immunoglobulin constant regions, such as polypeptide A or polypeptide G may also make up the labeled detection agent. These polypeptides are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401-1406, and Akerstrom (1985) *J. Immunol.*, 135: 2589-2542).

Preferred immunoassays for detecting the target polypeptide(s) are either competitive or noncompetitive. Noncompetitive immunoassays are assays in which the amount of captured analyte is directly measured. In competitive assays, the amount of analyte in the sample is measured indirectly by measuring the amount of an added (exogenous) labeled analyte displaced (or competed away) from a capture agent by the analyte present in the sample. In one competitive assay, a known amount of, in this case, labeled analyte is added to the sample, and the sample is then contacted with a capture agent. The amount of labeled analyte bound to the antibody is inversely proportional to the concentration of analyte present in the sample.

The assays of this invention are scored (as positive or negative or quantity of analyte) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of analyte concentration.

Antibodies

Antibodies useful in the immunoassay methods of the invention include polyclonal and monoclonal antibodies.

Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen.

If desired, the antigen may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal.

The antibodies are then obtained from blood samples taken from the animal. The techniques used to produce polyclonal antibodies are extensively described in the literature (see, e.g., Methods of Enzymology, "Production of Antisera With Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies see, for example, Coligan, et al. (1991) *Unit 9, Current Protocols in Immunology*, Wiley Interscience.

For many applications, monoclonal antibodies (mAbs) are preferred. The general method used for production of hybridomas secreting mAbs is well known (Kohler and Milstein (1975) *Nature*, 256:495). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody that bound to cancer cell lines. Confirmation of specificity among mAbs can be accomplished using routine screening techniques (such as the enzyme-linked immunosorbent assay, or "ELISA") to determine the elementary reaction pattern of the mAb of interest.

As used herein, the term "antibody" encompasses antigen-binding antibody fragments, e.g., single chain antibodies (scFv or others), which can be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) *Nature*, 348: 552-554; Hoogenboom et al. (1991) *Nucleic Acids Res.* 19: 4133-4137).

Since the antibody fragments on the surface of the phage are functional, phage-bearing antigen-binding antibody fragments can be separated from non-binding phage by antigen affinity chromatography (McCafferty et al. (1990) *Nature*, 348: 552-554). Depending on the affinity of the antibody fragment, enrichment factors of 20-fold-1,000,000-fold are obtained for a single round of affinity selection. By infecting bacteria with the eluted phage, however, more phage can be grown and subjected to another round of selection. In this way, an enrichment of 1000-fold in one round can become 1,000,000-fold in two rounds of selection (McCafferty et al. (1990) *Nature*, 348: 552-554). Thus, even when enrichments are low (Marks et al. (1991) *J. Mol. Biol.* 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) *J. Mol. Biol.* 222: 581-597). In one embodiment, natural VH and VL repertoires present in human peripheral blood lymphocytes are isolated from unimmunized donors by PCR. The V-gene repertoires can be spliced together at random using PCR to create a scFv gene repertoire which can be cloned into a phage vector to create a library of 30 million phage antibodies (Id.). From a single "naïve" phage antibody library, binding antibody fragments have been isolated against more than 17 different antigens, including haptens, polysaccharides, and proteins (Marks et al. (1991) *J. Mol. Biol.* 222: 581-597; Marks et al. (1993) *Bio/Technology,* 10: 779-783; Griffiths et al. (1993) *EMBO J.* 12: 725-734; Clackson et al. (1991) *Nature,* 352: 624-628). Antibodies have been produced against self-proteins, including, e.g., human thyroglobulin, immunoglobulin, tumor necrosis factor, and CEA (Griffiths et al. (1993) *EMBO J.* 12: 725-734). The antibody fragments are highly specific for the antigen used for selection and have affinities in the 1 nM to 100 nM range (Marks et al. (1991) *J. Mol. Biol.* 222: 581-597; Griffiths et al. (1993) *EMBO J.* 12: 725-734). Larger phage antibody libraries result in the isolation of more antibodies of higher binding affinity to a greater proportion of antigens.

As those of skill in the art readily appreciate, antibodies can be prepared by any of a number of commercial services (e.g., Berkeley Antibody Laboratories, Bethyl Laboratories, Anawa, Eurogenetec, etc.).

Solid Phase

For embodiments of the invention that employ a solid phase as a support for the capture agent, the solid phase can be any suitable porous material with sufficient porosity to allow access by reagents and a suitable surface affinity to bind a capture agent. Microporous structures are generally preferred, but materials with gel structure in the hydrated state may be used as well. Useful solid supports include: natural polymeric carbohydrates and their synthetically modified, crosslinked, or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto, bonded, or laminated to appropriate inert carriers, such as paper, glass, plastic films, fabrics, or the like.

Preferred solid phase materials for flow-through assay devices include filter paper such as a porous fiberglass material or other fiber matrix materials. The thickness of such material is not critical and will be a matter of choice, largely based upon the properties of the sample or analyte being assayed, such as the fluidity of the biological sample.

Alternatively, the solid phase can constitute microparticles. Microparticles useful in the invention can be selected by one skilled in the art from any suitable type of particulate material and include those composed of polystyrene, polymethylacrylate, polypropylene, latex, polytetrafluoroethylene, polyacrylonitrile, polycarbonate, or similar materials.

Microparticles can be suspended in the mixture of soluble reagents and biological sample or can be retained and immobilized by a support material. In the latter case, the microparticles on or in the support material are not capable of substantial movement to positions elsewhere within the support material.

The methods described herein can be adapted for use in systems that utilize microparticle technology including automated and semi-automated systems wherein the solid phase comprises a microparticle. Such systems include those described in pending U.S. App. No. 425,651 and U.S. Pat. No. 5,089,424, which correspond to published EPO App. Nos. EP 0 425 633 and EP 0 424 634, respectively, and U.S. Pat. No. 5,006,309.

In particular embodiments, the solid phase includes one or more electrodes. Capture agent(s) can be affixed, directly or indirectly, to the electrode(s). In one embodiment, for example, capture agents can be affixed to magnetic or paramagnetic microparticles, which are then positioned in the vicinity of the electrode surface using a magnet. Systems in which one or more electrodes serve as the solid phase are useful where detection is based on electrochemical interactions. Exemplary systems of this type are described, for example, in U.S. Pat. No. 6,887,714 (issued May 3, 2005). The basic method is described further below with respect to electrochemical detection.

Other considerations affecting the choice of solid phase include the ability to minimize non-specific binding of labeled entities and compatibility with the labeling system employed. For, example, solid phases used with fluorescent labels should have sufficiently low background fluorescence to allow signal detection.

Following attachment of a specific capture agent, the surface of the solid support may be further treated with materials such as serum, proteins, or other blocking agents to minimize non-specific binding.

Labeling Systems

As discussed above, many immunoassays according to the invention employ a labeled detection agent.

Detectable labels suitable for use in the detection agents of the present invention include any composition detectable by spectroscopic, photochemical, biochemical, immunochemical, electrical, optical, or chemical means. Useful labels in the present invention include magnetic beads (e.g., Dynabeads™), fluorescent dyes (e.g., fluorescein, texas red, rhodamine, green fluorescent protein, and the like, see, e.g., Molecular Probes, Eugene, Oreg., USA), chemiluminescent compounds such as acridinium (e.g., acridinium-9-carboxamide), phenanthridinium, dioxetanes, luminol and the like, radiolabels (e.g., $^3$H, $^{125}$I, $^{35}$S, $^{14}$C, or $^{32}$P), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The label can be attached to the detection agent prior to, or during, or after contact with the biological sample. So-called "direct labels" are detectable labels that are directly attached to or incorporated into detection agents prior to use in the assay. Direct labels can be attached to or incorporated into detection agents by any of a number of means well known to those of skill in the art.

In contrast, so-called "indirect labels" typically bind to the detection agent at some point during the assay. Often, the indirect label binds to a moiety that is attached to or incorporated into the detection agent prior to use. Thus, for example, an antibody used as a detection agent (a "detection antibody") can be biotinylated before use in an assay. During the assay, an avidin-conjugated fluorophore can bind the biotin-bearing detection agent, to provide a label that is easily detected.

In another example of indirect labeling, polypeptides capable of specifically binding immunoglobulin constant regions, such as polypeptide A or polypeptide G, can also be used as labels for detection antibodies. Such polypeptides can thus be labeled and added to the assay mixture, where they will bind to the detection antibody.

Some labels useful in the invention may require the use of an indicator reagent to produce a detectable signal. In an ELISA, for example, an enzyme label (e.g., beta-galactosidase) will require the addition of a substrate (e.g., X-gal) to produce a detectable signal.

Mitochondrial PRODH Bioassays

Mitochondrial PRODH bioassays capable of measuring inhibitor activity are described in Goncalves et al. (2014) *Redox Biol.* 2: 901-909 (which is hereby incorporated by reference herein for this description). These include, inter alia: i) spectrophotometric detection of OAB reacted with proline generated P5C, ii) dual wavelength spectrophotometric detection (A566-A575) of endogenous cytochrome b566 reduction that occurs directly upon mitochondrial PRODH oxidation of proline, and iii) fluorescence spectrometry detection (lex 340 nm, lem 460 nm) of mitochondrial NADH levels as a function of substrate and inhibitor treatment. See details in Example below. The mitochondrial PRODH assay is described therein detects mitochondrial NADH production resulting downstream from PRODH production of P5C and then glutamate, while controlling for other sources of mitochondrial NADH production.

Test Kits

The invention also provides test kit for assaying for one or more of the enzymes described above. Test kits according to the invention include one or more reagents useful for practicing one or more immunoassays according to the invention. A test kit generally includes a package with one or more containers holding the reagents, as one or more separate compositions or, optionally, as admixture where the compatibility of the reagents will allow. The test kit can also include other material(s) that may be desirable from a user standpoint, such as a buffer(s), a diluent(s), a standard(s), and/or any other material useful in sample processing, washing, or conducting any other step of the assay.

Test kits according to the invention preferably include instructions for carrying out one or more of the immunoassays of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

Use of Enzyme Level Information

Once determined, an enzyme level can be recorded in a patient medical record. In certain embodiments, the methods of the invention include making a treatment recommendation or prescription, based at least in part on the enzyme level. This information can also be recorded in a patient medical record. The medical record can be in paper form and/or can be maintained in a computer-readable medium. The medical record can be maintained by a laboratory, physician's office, a hospital, a health maintenance organization, an insurance company, and/or a personal medical record website.

In particular embodiments, the methods of the invention include informing the subject of a result of the enzyme assay and/or of a treatment recommendation or prescription based at least in part on the enzyme level. The patient can be informed verbally, in writing, and/or electronically.

In certain embodiments, the methods of the invention can include prescribing, initiating, and/or altering prophylaxis and/or therapy for cancer based on the enzyme levels detected as described above. For example, in some embodiments, a sample of cancer obtained from a subject is assayed for PRODH level. If the PRODH level is elevated relative to a normal level, the subject can be treated with a drug that inhibits proline catabolism, for example, according to any of the cancer treatment methods described above. In certain embodiments, the sample is additionally tested to determine whether cancer cells include at least one functional p53 allele. If so, the subject can additionally be treated, e.g., with a p-53-activating drug. In particular embodiments, the sample is additionally assayed for GLS level. If the GLS level is elevated relative to a normal level, the subject can additionally be treated with a drug that inhibits GLS, as described above. In various embodiments, the GLS level is assayed in a non-specific assay (i.e., one that does not distinguish among the isoenzymes) or an assay specific for GLS1 or GLS2 is employed.

EXAMPLES

The following examples are offered to illustrate, but not to limit the claimed invention.

Example 1

Targeting Proline Dehydrogenase (PRODH) Induces Synthetic Lethal Interactions with p53 Restoring Drugs and Glutaminase (GLS1) Inhibitors in Breast Cancer One strategy for developing more selective and less toxic anticancer agents is to leverage the "synthetic lethal" metabolic interactions exhibited by loss of function of a key mitochondrial enzyme, proline dehydrogenase (PRODH), critical for cancer cell ATP and glutamate production. Using computational modeling of PRODH's molecular structure to identify and evaluate an initial set of competitive and mechanism-based small molecule PRODH inhibitors capable of these synthetic lethal and synergistic anticancer interactions, we are synthesizing and elucidating the novel mechanism of action of more potent and specific suicide inhibitors of PRODH (see, e.g., FIGS. 5A and 5B), whose enhanced anticancer activity also exploits selective disturbance in mitochondrial proteostasis including activation of the mitochondrial matrix-localized unfolded protein response.

We have shown that the p53 inducible gene and mitochondrial enzyme, proline dehydrogenase (PRODH), critically supports breast cancer cell growth and survival by consuming proline for anaplerotic glutamate production, bypassing glutaminase (GLS1) to fuel oxidative phosphorylation and sustain ATP levels. As a novel therapeutic strategy, we have found that PRODH knockdown, or its enzymatic inhibition by either proline competitive inhibitors like LTHFA and 5-oxo-2-tetrahydrofurancarboxylic acid (5-oxo) or the more potent mechanism-based PRODH "suicide" inhibitor, propargylglycine (PPG), not only impairs breast cancer growth by itself, but when combined with either a p53 restoring drug (MI-63) or a clinical GLS1 inhibitor (CB-839) produces a "synthetic lethal" and synergistic anticancer response against malignant but not normal breast epithelial cells. We synthesized additional potent and specific suicide inhibitors of PRODH that are not only capable of such synthetic lethal interactions, but whose enhanced anticancer activity appears to exploit selective activation of the tumor cell's mitochondrial matrix-localized unfolded protein response, causing rapid induction of PRODH protein degradation.

Specific Aspects

As with other malignancies, a hallmark of breast cancer is its metabolic reprogramming. About 75% of all newly diagnosed breast cancers express wildtype (wt) p53 and are therefore vulnerable to p53 restoring drugs like small molecule MDM2 inhibitors (e.g., nutlin-3a, MI-63) that induce early and very significant differences in mitochondrial bioenergetics and global metabolic pool changes between malignant (e.g., MCF7, ZR-75-1, ZR-75-30, DU4475) and non-malignant (e.g., MCF-10A) breast cells, leading to cancer-selective apoptosis or irreversible growth arrest. In contrast, tumor cells bearing mutated (mut) p53, especially triple-negative breast cancer cell lines, are often glutamine addicted for mitochondrial glutamate production and anapleurosis to meet their biosynthetic and energy demands, rendering them particularly susceptible to glutaminase (GLS1) inhibitors (e.g., CB-839). We have now shown that the p53 inducible gene and mitochondrial enzyme, proline dehydrogenase (PRODH), critically supports breast cancer cell growth and survival by consuming proline to bypass GLS1 for anapleurotic glutamate production to fuel oxidative phosphorylation and sustain ATP levels. As a novel therapeutic strategy, we have found that PRODH knockdown or its enzymatic inhibition by either proline competitive inhibitors, L-THFA or 5-oxo-2-tetrahydrofurancarboxylic acid (5-oxo), or a more potent mechanism-based "suicide" inhibitor of PRODH, N-propargylglycine (PPG), not only impairs breast cancer growth by itself, but when combined with either a p53 restoring MDM2 inhibitor (MI-63) or a GLS1 inhibitor (CB-839) yields a "synthetic lethal" response with synergistic induction of cancer (but not normal) cell apoptosis. We have synthesized additional potent and specific suicide inhibitors of PRODH, capable of synthetic lethal interactions with either p53 restoring or GLS1 inhibiting drugs for future combinatorial treatment of all forms of breast cancer as well as many other malignancies similarly susceptible to these agents.

Figure 5A:
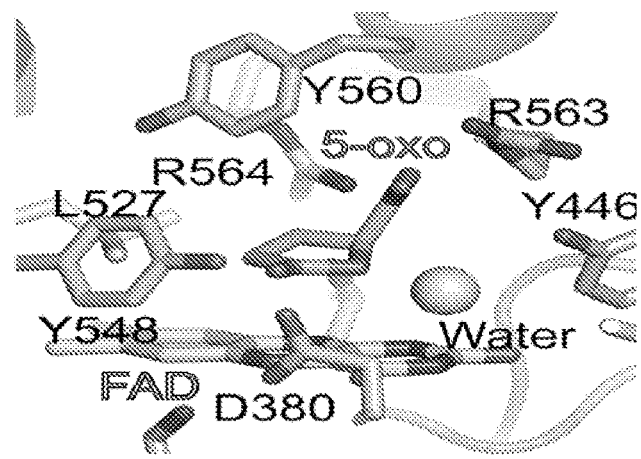
FIGS. 5A and 5B illustrate modeling of irreversible and reversible PRODH inhibitors.
Figure 5A:
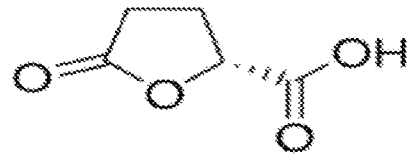
Figure 5A:
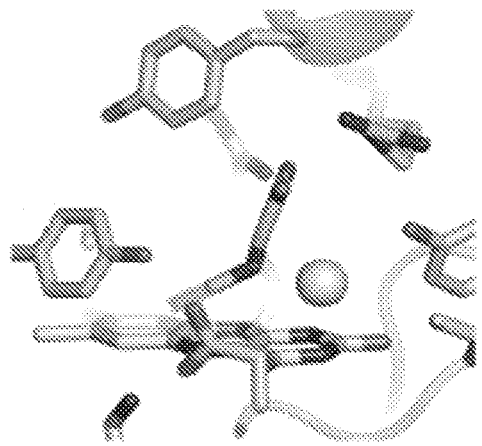
Figure 5A:
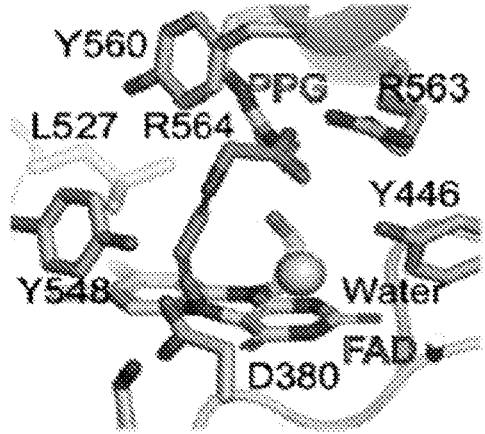
Figure 5B:
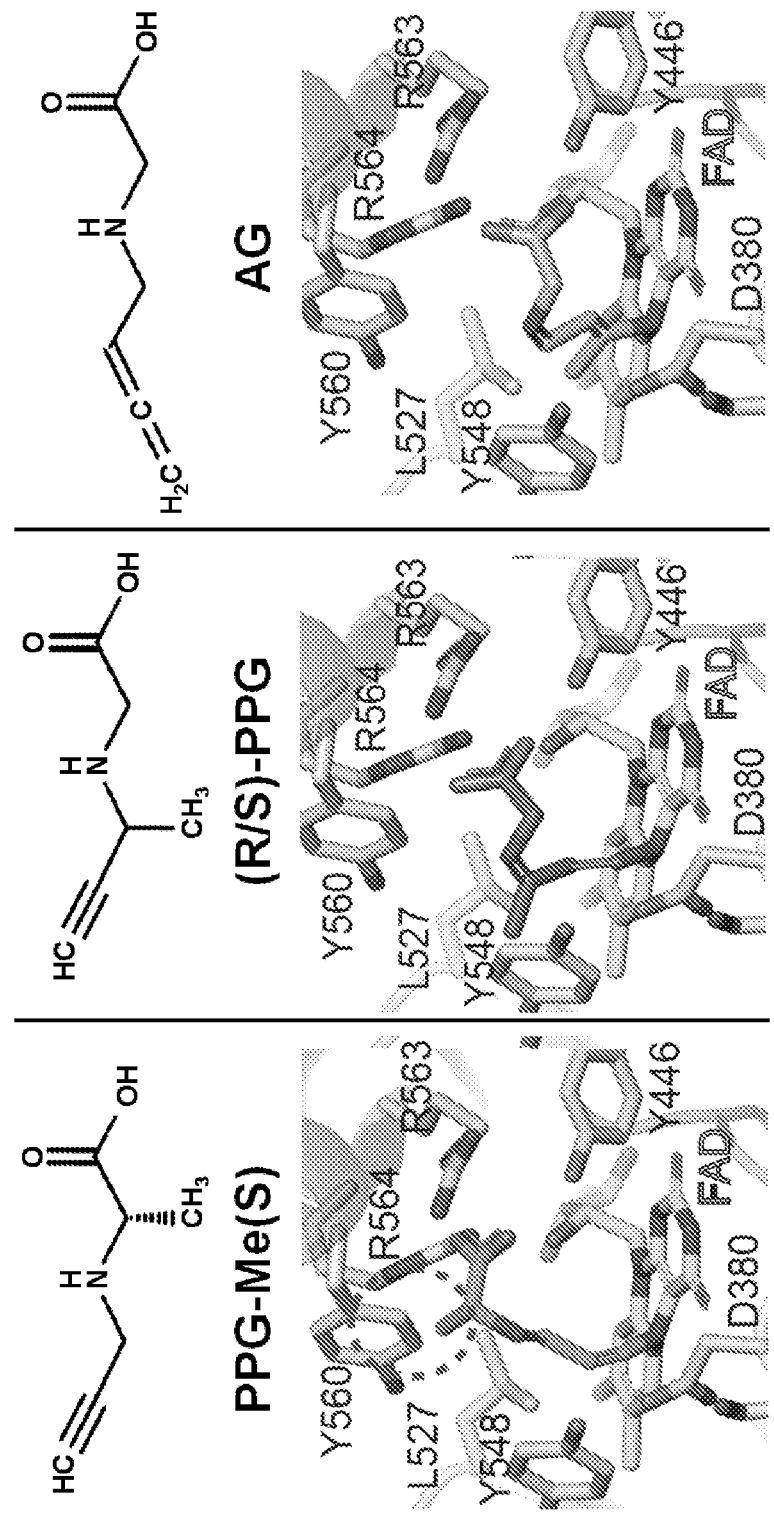

Having employed siRNA knockdown of PRODH and other key proline catabolizing mitochondrial enzymes to assure that PRODH is the most critical rate limiting step whose inactivation is sufficient for our desired synthetic lethal interactions, we have and are presently exploiting model-directed design to synthesize and mechanistically evaluate more potent and selective drug-like PRODH inhibitors. As illustrated in FIGS. 5A and 5B we have focused synthesis and mechanism-of-action studies on a set of propargylic (PPGlike) analogs that not only inhibit PRODH enzymatic activity more effectively than the competitive inhibitors LTHFA and 5-oxo, but also possess the unique property of inducing specific intra-mitochondrial PRODH protein degradation, presumably by activating the mitochondrial matrix-localized unfolded protein response ($UPR_{mt}$).

Figure 6:
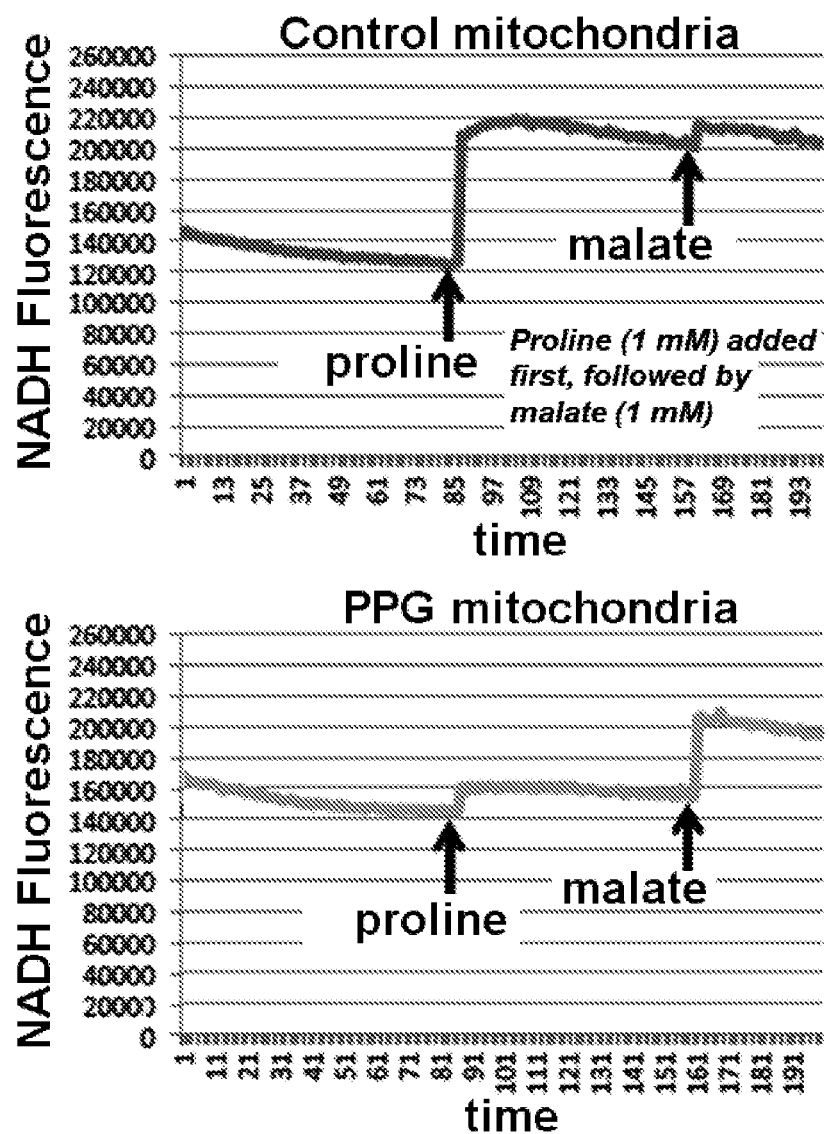
FIG. 6 shows use of an NADH-generating mitochondrial PRODH bioassay to compare PRODH inhibitor effects. Mitochondria freshly isolated from PPG pretreated (15 h) and washed (30 min) ZR-75-1 cells remain unable to metabolize proline, although malate metabolism is not affected. Comparable immediate enzymatic inhibition induced by a reversible PRODH inhibitor (5-oxo) is completely lost (reversed) by the same washout.

PRODH enzyme activity-inhibiting doses of specific and reversible/competitive inhibitors like (S)-5-oxo or L-THFA can be immediately and readily washed out with L-proline exposure, restoring full enzymatic activity. In contrast, PRODH enzyme exposure to a comparably specific irreversible/suicide inhibitor like PPG, even when administered at the same initial enzyme activity-inhibiting dose (or comparable Ki) quickly reacts within the enzyme pocket (covalently linking to the nearby FAD co-substrate and/or an amino acid lining the PRODH pocket), preventing pocket washout by excess additional L-proline while also simultaneously distorting the PRODH structure and permanently disabling each bound PRODH enzyme within the mitochondria. In FIG. 6 mitochondria freshly isolated from human ZR-75-1 cancer cells pretreated (×15 h) with PPG (1-5 mM), thoroughly washed and then exposed to exogenous proline, remained completely unable to metabolize proline (forming NADH) yet the same treated mitochondria are fully capable of metabolizing malate (forming NADH).

Figure 7:
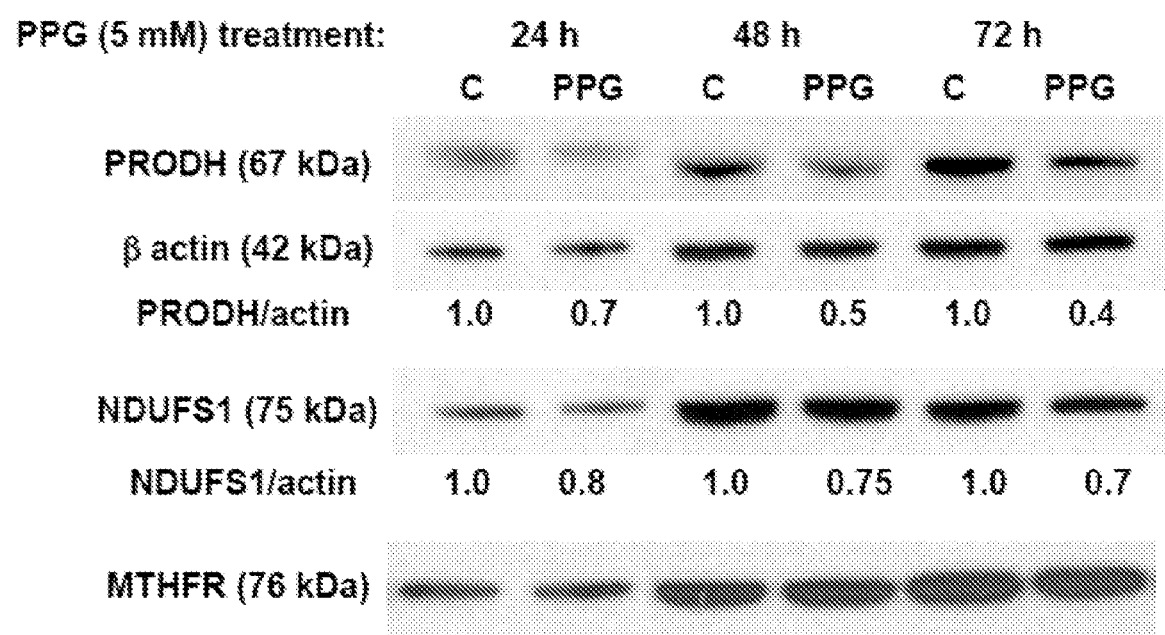
FIG. 7: The PRODH suicide inhibitor, PPG, following its rapid inhibition of PRODH enzyme activity induces a time-dependent selective degradation of PRODH protein (30-60%) within 24-72 h of ZR-75-1 culture treatment. Mitochondrial complex-1 protein NDUFS1 also declines, but the cytoplasmic FAD containing protein MTHFR does not, and tracks with total cell actin levels. This illustrates differential mitochondrial consequences produced by irreversible versus competitive PRODH inhibitors. Unlike cancer cell death associated with competitive PRODH inhibitors like (S)-5-oxo, and as shown in MCF7 cells after 24-72 h treatment with an irreversible "suicide" inhibitor like PPG (5 mM), there is initial selective degradation of mitochondrial PRODH followed by loss of other mitochondrial proteins (e.g. NDUFS1), days before any detectable degradation of other cytosolic FAD-containing proteins (e.g. MTHRF). In normal cells not susceptible to the toxic consequences of PRODH inhibition, the suicide inhibitor's distortion of PRODH structure can activate mitohormesis and subsequently enhance cell stress resistance.

Beyond preventing enzymatic function a covalently bound PRODH suicide inhibitor (e.g. PPG) elicits, presumably by structural distortion or permanent disablement of the PRODH protein molecule, a mitochondrial response that does not similarly occur following comparable PRODH enzyme inhibition by a reversible/competitive inhibitor; this intracellular response is referred to as altered mitochondrial proteostasis. As shown in FIG. 7, this mitochondrial proteostatic response to PPG is characterized by early and progressive (beginning within 24 h, progressing to 72 h or later) degradation of the bound and inhibited mitochondrial PRODH protein, accompanied by some degree of mitochondrial destruction (e.g. loss of other mitochondrial proteins like NDUFS1), but not whole cell destruction or even loss of any extra-mitochondrial proteins/enzymes like the FAD-containing enzyme MTHFR. For normal cells, which usually express minimal PRODH levels and whose energy and synthetic needs are not dependent on proline catabolism, a PPG induced mitochondrial proteostatic response does not lead to cell apoptosis but instead may signal a mitohormetic response that can result in increased cell resistance to stress and, if appropriately timed, may also enhance whole organism viability and longevity. In contrast, for proline-addicted cancer cells exposed to a competitive PRODH inhibitor, mitochondrial proteostasis does not occur although some degree of dose-dependent apoptosis may result from the loss of glutamate and ATP production; instead, for the same proline-addicted cancer cells exposed to a PPG-like suicide inhibitor at a dose causing comparable PRODH enzyme activity-inhibition, induction of the mitochondrial proteostatic response in addition to loss of ATP and glutamate production results in a significantly enhanced apoptotic response and cancer-inhibiting effect, as well as a stronger synthetic lethal interaction with p53 upregulation, glutaminase inhibition and/or hypoxia.

To demonstrate synthetic lethality, these and other PPG-like analogs with optimal PRODH inhibiting and degrading potential can be administered with either p53 restoring MI-63, or GLS1 inhibiting CB-839, using appropriate luminal and triple-negative breast cancer cell line models and assessing cell proliferation and apoptotic responses.

Having successfully employed our structural model of human PRODH to identify more effective competitive inhibitors like 5-oxo, this model is leveraged to extend the specificity and affinity of the suicide inhibitor PPG. Since modeling of PPG within the PRODH catalytic site predicts full accommodation and covalent reaction with PRODH's FAD moiety, a set of R-substituted PPG-like analogs are designed to be synthesized and evaluated for their capacity to inhibit proline metabolism using our new mitochondrial PRODH activity assay, and confirm the predicted FAD-linked suicide mechanism.

The synthetic lethality potential of the new set of PPG-like PRODH suicide inhibitors can be compared with our PRODH competitive inhibitors (L-THFA, 5-oxo), given in dose-dependent combinations with MI-63 and CB-839, using a panel of p53 wt malignant (MCF7, ZR-75-1, DU4475), p53 wt non-malignant (MCF10A) and p53mut malignant (BT474, T47D, SKBr3, MDA-231) breast epithelial cell lines, assess anti-proliferative and pro-apoptotic cell responses, and link these to PRODH protein degradation.

Significance

Proline Metabolism Supports Breast Cancer Cell Survival.

From prokaryotes to the highest eukaryotes, proline is cabolized by a unique and structurally conserved flavoprotein, proline dehydrogenase (PRODH) (1. Servet et al. (2012) *Front. Biosci.* 17: 607-620; Phang et al. (2012) *Front. Oncol.* 2: 60; Bender et al. (2005) *Am. J. Hum. Genet.* 76: 409-420; Lee et al. (2003) *Nat. Struct. Biol.* 10: 109-114). In eukaryotes PRODH associates with the inner mitochondrial membrane and catalyzes the first and rate limiting catabolic step to yield the intermediate metabolite, pyrroline-5-carboxylate (P5C), with transfer of two electrons to the electron transport chain where they can produce ATP and/or reactive oxygen species (ROS), as illustrated in FIG. 1. Proline's high metabolic potential of ~30 ATP equivalents/mol is exploited by many insects like the Tsetse fly, carrier of African sleeping sickness whose flight is fueled by proline oxidation, prompting early efforts to find PRODH inhibitors to control that scourge (Servet et al. (2012) *Front. Biosci.* 17: 607-620; Hargrove (1976) *J. Insect Physiol.* 22: 309-3135).

PRODH's potential importance in cancer emerged when it was uncovered by Vogelstein's group as one of the most strongly upregulated genes by the p53 wt tumor suppressor protein, although its identity was unknown at that time and it was simply referred to as "p53-induced gene 6" (PIG6) (Polyak et al. (1997) *Nature* 389: 300-305). PRODH's functional importance in tumor mitochondria grew out of later studies spearheaded largely by J W Phang, who was interested in the in vivo role of exogenous proline from breakdown of extracellular matrix collagen in sustaining intracellular ATP by anaplerotic contribution to the TCA cycle (Phang et al. (2012) *Front. Oncol.* 2: 60; Pandhare et al. (2009) *J. Cell Biochem.* 107: 759-768). Phang's studies first suggested that PRODH's capacity to generate reactive oxygen species (ROS) and induce apoptosis qualified it as a tumor suppressor, providing rationale for its induction by p53 (Donald et al. (2001) *Cancer Res.* 61(5):1810-1815; Liu and Phang (2012) *Autophagy* 8: 1407-1409). Later studies pointed to PRODH's potential to promote cancer cell survival via its ATP production (Liu et al. (2012) *Cancer Res.* 72: 3677-3686; Liu et al. (2012) *Proc. Natl. Acad. Sci. USA,* 109: 8983-8988); and our recent report comparing PRODH and proline oxidation between insect cells and cancer cell lines definitively showed that while PRODH can induce mitochondrial ROS production it does so almost exclusively at other mitochondrial sites (e.g., complex I, ⟨-KG dehydrogenase complex) and via its anaplerotic glutamate production, not directly by PRODH itself (Goncalves et al. (2014) *Redox Biol.* 2: 901-909). Our latest studies also prove that PRODH expression supports, and is often absolutely essential for, cancer cell growth and survival (see, e.g., FIG. 2).

PRODH Inhibition Exploits Synthetic Lethal Interactions with p53 Restoration and Glutamine Addiction.

Restoration of p53 function represents a promising therapeutic strategy with the clinical emergence of new agents including MDM2 inhibitors like nutlin-3a, MI-63 (Vassilev et al. (2004) *Science,* 303: 844-848; Shangary et al. (2008) *Proc. Natl. Acad. Sci. USA,* 105: 3933-3938; Shangary and Wang (2008) *Clin. Cancer Res.* 14: 5318-5324; Ray-Coquard et al. (2012) *Lancet Oncol.* 13: 1133-1140) and other p53 reactivating drugs (Wade et al. (2013) *Nature Rev. Cancer,* 13: 83-96, 2013; Burmakin et al. (2013) *Clin. Cancer Res.* 19: 5092-5103). But, the development of resistance to p53 restoration as shown in several experimental models (Aziz et al. (2011) *Oncogene* 30: 4678-4686) also reveals our incomplete understanding of how p53 not only regulates cell growth, survival and senescence but also reprograms cancer cell metabolism including mitochondrial glutamate production by PRODH and GLS2 induction (Gottlieb et al. (2009) *Cold Spring Harb Perspect Biol* 2:a001040).

Figure 2:
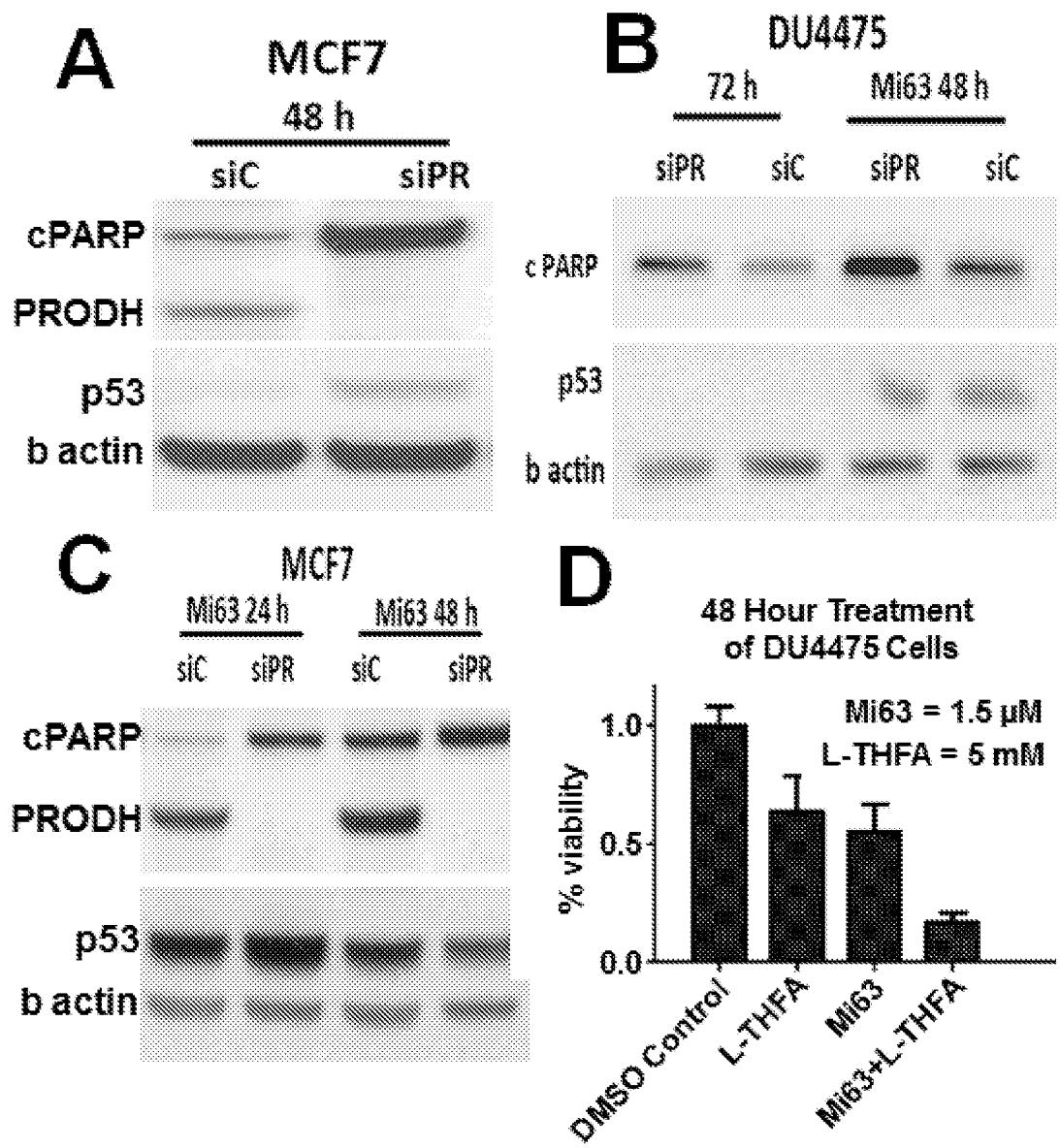
FIG. 2, panels A-D: PRODH siRNA knockdown (siPR) in MCF7 (panel A) and DU4475 (panel B) induces apoptosis detected by cleaved (panel c) PARP on Western blots, less so in ZR-75-1 cells whose higher PRODH levels are more difficult to reduce by siRNA knockdown (panel A). When combined with MI-63 (24-48 h) restoration of p53 wt, PRODH knockdown in the DU4475 (panel B) and MCF7 (panel C) cells produces synthetic lethality with marked increase in apoptosis (c PARP). (Panel D) Viability assay demonstrates synthetic lethality effectiveness of L-THFA combined with MI-63 in DU4477.

Our recent studies have shown that p53 wt restoration by the MDM2 inhibitor MI-63 triggers early and very different mitochondrial bioenergetic and global metabolic pool changes between malignant (e.g., MCF7, ZR-75-1, ZR-75-30, DU4475) and non-malignant (e.g., MCF-10A) mammary epithelial systems (Yau et al. (2011) *Amer. Assoc. Cancer Res.* 52: a3797, 2011; Yau et al. (2012) *Amer. Assoc. Cancer Res.* 53: a5160). Having first observed that PRODH siRNA knockdown promotes apoptosis in p53 wt breast cancer cells, we then evaluated PRODH knockdown in combination with MI-63 induced p53 restoration. As shown in FIG. 2, p53 restoration combined with PRODH knockdown significantly enhances apoptosis in MCF7 and DU4475 (and other) breast cancer models relative to either treatment alone. Knockdown of P5CDH (the next enzymatic step in proline catabolism) produced a similar but less pronounced pro-apoptotic response in combination with MI-63, convincing us that PRODH is the most appropriate therapeutic target for synthetic lethality. Of translational relevance, both competitive (e.g., L-THFA, 5-oxo) and mechanism-based suicide (e.g., PPG) inhibitors of PRODH induce similar synthetic lethal interactions with p53 wt restoration in our various breast cancer models. Equally relevant, since PRODH provides a bypass source of mitochondrial glutamate for glutamine-addicted (e.g., GLS1 overexpressing) cancers, particularly those most sensitive to clinically emergent GLS1 inhibitors like CB-839 (Katt and Cerione (2014) *Drug Discov. Today,* 19: 450-457; Gross et al. (2014) *Mol. Cancer Ther.* 13: 890-901), our new data also supports the fact that PRODH inhibition induces a synthetic lethal anticancer response in combination with GLS1 inhibition among our various breast cancer models. Moreover, as shown in FIG. 4, and Tables 3 and 4 we find that PRODH and GLS1 transcript levels are strongly inversely correlated across 51 different breast cancer cell lines (Neve et al. (2006) *Cancer Cell.* 10: 515-527) representing all human breast cancer subtypes, suggesting that one or the other of these mitochondrial pathways is needed to feed cancer's anaplerotic addiction to glutamate. These data strongly support our therapeutic approach and it is believed that PRODH inhibitors capable of synthetic lethal responses in combination with either p53 restoring or GLS1 inhibiting drugs, can treat virtually all forms of breast cancer as well as many other malignancies similarly susceptible to such agents.

TABLE 3

Summary table showing primarily synergistic growth inhibiting interactions in different breast cancer lines at 72 h after combined treatment with PRODH (5-oxo) and GLS1 (CB-839) inhibitors.

| Cell Line Phenotype | | | | Combinations with Glutaminase Inhibitor (CB-839) | |
|---|---|---|---|---|---|
| P53 | PRODH Expression | GLS1 Expression | Cell Line | +5-oxo (5 mM) | +Nutlin-3a (5 µM) |
| Mutated | ++ | + | BT474 | Additive | No interaction |
| Wildtype | + | + | MCF7 | Synergistic | Additive |
| Wildtype | +/− | +++ | DU4475 | Synergistic | Synergistic |
| Wildtype | +++ | +/− | ZR75-1 | Synergistic | Additive |

TABLE 4

Summary table showing synergistic lethality of PRODH inhibition combined with GLS1 inhibition.

| Cell Line Phenotype | | | | Treatment Interaction |
|---|---|---|---|---|
| P53 | PRODH Expression | GLS1 Expression | Cell Line | +5-oxo (1 µM) + CB839 (1 µM) |
| Mutated | ++ | + | BT474 | Additive |
| Wildtype | + | + | MCF7 | Synergistic |
| Wildtype | +/− | +++ | DU4475 | Synergistic |
| Wildtype | +++ | +/− | ZR75-1 | Synergistic |

The quest for PRODH inhibitors goes back nearly 40 years when this was considered a possible approach to eradicate tsetse flies and prevent African trypanosomiasis. While the first mechanism-based PRODH inhibitor was proposed in 1993 (Tritsch et al. (1993) *Biochim Biophys Acta,* 1202: 77-81), further progress in this effort was stymied until a decade ago when Tanner's group generated the first crystal structures of bacterial forms of PRODH (Lee et al. (2003) *Nat. Struct. Biol.* 10: 109-114). Tanner's most recent crystal structure of bacterial PRODH bound to the competitive inhibitor, L-THFA, was reported only two years ago (Luo et al. (2012) *Biochemistry* 51: 10099-10108), and provides the current basis for our computer modeling of human PRODH. Interestingly, four years earlier his group described a possible mechanism-based PRODH inhibitor, N-propargylglycine (PPG); unfortunately, bacterial PRODH is so structurally dissimilar to higher order and mammalian PRODHs that the proposed inactivating mechanism by PPG is implausible for anticancer research as it depends on key bacterial residues not present in either insect or human PRODH (White et al. (2008) *Biochemistry* 47: 5573-5580). However, using our new human model of PRODH and drawing upon other structural and mechanistic studies employing propargylic (PPG-like) analogs like Rasagiline (N-propargyl-1 (R)-aminoindan), an FDA-approved selective and irreversible inhibitor of the FAD-containing monoamine oxidase (MAO)-B currently used to treat Parkinson's disease (Binda et al. (2005) *J. Med. Chem.* 48: 8148-8154), we now propose a unique synthetic route and suicide-based mechanism for the development of an entirely new family of propargylic PRODH inhibitors. From our updated knowledge about PRODH expression in human breast cancers, its known induction by p53 wt and its inverse relationship to GLS1 expression as a bypass mechanism to produce mitochondrial glutamate, we also believe that the most important clinical impact from a new drug-like PRODH inhibitor will ultimately be seen in combination therapy with either a p53 restoring drug or with a GLS1 inhibitor, both emergent classes of novel cancer therapeutics that we show here are fully capable of engaging in a synthetic lethal anticancer interaction with effective PRODH inhibition.

New cancer treatments based on the restoration or reactivation of p53 wt function were first envisioned over a decade ago, and multiple pharmacological strategies have since emerged from preclinical studies that now show great clinical promise (12-17), particularly against malignancies like breast cancers in which 75% of all newly diagnosed cases express wildtype p53 (TCGA Network (2012). *Nature* 490: 61-70). Pharmacologically restored p53, unlike endogenously stabilized p53 that develops following cellular stress, lacks the array of posttranslational modifications that are thought to not only suppress proteolytic degradation of p53 but also direct its "genome guardian" responses toward either activation of apoptosis or cell preservation and repair by cell cycle arrest (Saha et al. (2010) *Clin. Pathol.* 63:204-209). In this context we understand that pharmacologically restored p53 is "naïve" with regard to its programmed response activating both cell death and survival mechanisms, enabling our synthetic lethal approach to become manifest by therapeutically inhibiting one essential cancer-associated p53 survival response, namely PRODH induction, and tipping the balance in cancer (but not normal) cells toward a greatly enhanced p53 apoptotic response. Using a close chemical prototype (MI-63) of the spiro-oxindole now entering clinical trials (SAR299155; Ascenta/Sanofi-Aventis) against a panel of malignant and non-malignant breast epithelial cells, we have shown that p53 restoration in malignant cells destined to undergo apoptosis initially show global metabolic pool shifts and mitochondrial bioenergetic changes that differ significantly from responses seen in non-malignant cells (Yau et al. (2011) *Amer. Assoc. Cancer Res.* 52: a3797). Among these early changes are consequential p53 effects on proline oxidation, including at least a 5-fold induction of PRODH protein levels (with no change in P5CDH) and a coordinate decrease in P5C reductase (PYCR1) levels. Likewise, p53 induced metabolic changes linking proline metabolism to the urea cycle (OAT) and to glutaminolysis (GLS2) and the TCA cycle have been observed in our model systems (Yau et al. (2012) *Amer. Assoc. Cancer Res.* 53: a5160). In particular, the noted glutamine addiction of many cancers with upregulated mitochondrial glutaminolysis, mediated either by Myc-induced GLS1 or p53-induced GLS2 (which are inversely expressed), has attracted considerable recent attention (Katt and Cerione (2014) *Drug Discov. Today,* 19: 450-457), particularly given the promising preclinical and clinical effectiveness of new GLS1 inhibitors like CB-839 (Calithera) (Gross et al. (2014) *Mol. Cancer Ther.* 13: 890-901). Our latest observations (FIG. 4) showing that PRODH and GLS1 are inversely expressed and that their combined inhibition leads to synergistic growth inhibition, presumably by more efficient mitochondrial glutamate deprivation, supports this other equally important synthetic lethal opportunity for an effective PRODH inhibitor, beyond what we envisioned in connection with p53 restoration.

Approach

Having employed siRNA knockdown of PRODH and other key proline catabolizing mitochondrial enzymes to assure that PRODH is the most critical rate limiting step whose inactivation is sufficient for our desired synthetic lethal interactions, we are exploiting model-directed design to synthesize and mechanistically evaluate more potent and selective drug-like PRODH inhibitors. Our synthesis and mechanism-of-action studies are focused on a set of propargylic (PPG-like) analogs that not only inhibit PRODH enzymatic activity more effectively than our competitive inhibitors, L-THFA and 5-oxo, but as suicide inhibitors also possess the unique property of inducing specific intra-mitochondrial PRODH protein degradation, presumably by activating the mitochondrial matrix-localized unfolded protein response ($UPR_{mt}$). To demonstrate synthetic lethality, PPG-like analogs with optimal PRODH inhibiting and degrading potential can be administered with either p53 restoring MI-63, or GLS1 inhibiting CB-839, using appropriate luminal and triple-negative breast cancer cell line models and assessing their cell proliferation and apoptotic responses.

Mitochondrial PRODH Bioassay to Assess New Enzymatic Inhibitors.

We have optimized our mitochondrial preparation technique and developed three different mitochondrial PRODH bioassays capable of measuring inhibitor activity which are now reported (Goncalves et al. (2014) *Redox Biol.* 2: 901-909); these include: i) spectrophotometric detection of OAB reacted with proline generated P5C, ii) dual wavelength spectrophotometric detection (A566-A575) of endogenous cytochrome b566 reduction that occurs directly upon mitochondrial PRODH oxidation of proline, and iii) fluorescence spectrometry detection (lex 340 nm, lem 460 nm) of mitochondrial NADH levels as a function of substrate and inhibitor treatment.

Briefly, in an exemplary protocol, cells are harvested from 2 to 4500 $cm^2$ dishes at 90% confluence, washed three times in ice-cold STE (250 mM sucrose, 5 mM Tris-HCl, 2 mM EGTA, pH7.4), scraped off, suspended in 50 ml STE and centrifuged for 10 min at 500 g. The pellet is resuspended in STE supplemented with 1% (w/v) fatty acid-free bovine serum albumin and homogenized (up to 20 strokes). The suspension is brought to 50 ml and centrifuged for 5 min at 1000 g. The supernatant is centrifuged for 10 min at 11,000 g. The pellet is resuspended in STE and centrifuged for 10 min at 10,000 g. The mitochondrial pellet is resuspended in STE and kept on ice. Protein is determined by Bradford assay(Biorad).

For spectrophotometric detection of OAB reacted with proline generated P5C, mitochondria (0.1 mg protein/ml) are incubated for 10 min in KHE (120 mM KCl, 3 mM HEPES, 5 mM $KH_2PO_4$, pH7.2) containing 1 mM ADP, 5 µM carbonylcyanide, 4-(trifluoro-methoxy)phenylhydrazone (FCCP), 2.5 µg/ml oligomycin and 5 mM o-aminobenzaldehyde(oAB). 5 mM proline is added +/−4 µM rotenone or 2 µM myxothiazol. At 30 min the reaction is stopped by adding 0.5% (v/v) trichloroacetic acid. pH is brought to 7.1 using KOH. Tubes are centrifuged for 10 min at 10,000 g and the supernatants are transferred to new tubes containing an extra 5 mM oAB to fully develop the assay. $A_{440}$ of the P5C-oAB complex is measured and the concentration is calculated using $\epsilon_M$=2580. $A_{440}$ without mitochondria or proline is typically about 14% of the standard value.

The reduction state of endogenous cytochrome $b_{566}$ can be measured using 0.75 mg mitochondrial protein/ml in KHE plus 2.5 µg/ml oligomycin and 1 mM ADP with constant stirring at 25° C. in an Olis DW2-dual wavelength spectrophotometer at $A_{566}$-$A_{575}$ nanometers. Cytochrome $b_{566}$ is assumed to be 0% reduced after 5 min without added substrate, then 4 µM rotenone, 5 mM malonate and 2 µM antimycinA are added to report reduction caused by endogenous substrates. 5 mM proline is subsequently added and % cytochrome b566 reduction was determined relative to the 0% and 100% values. Cytochrome b566 is assumed to be 100% reduced after addition of 5 mM succinate plus 5 mM glycerolphosphate.

NAD(P)H is measured using 0.3 mg mitochondrial protein/ml at 37° C. in KHEPMB (KHE containing 5 mM $K_2HPO_4$, 2 mM $MgCl_2$, 0.3% (w/v) fatty acid-free bovine serum albumin) plus 1 mM ADP and 2.5 µg/ml oligomycin. The reduction state of endogenous NAD(P)H Is determined by autofluorescence using the Pherastar microplate reader at λexcitation=340 nm, λemission=460 nm. NAD(P)H was assumed to be 0% reduced after 5 min without added substrate, then rotenone was added. The 100% reduced level was established with saturating substrate (e.g., 5 mM malate, glutamate and proline) and 4 µM rotenone. Intermediate values were determined as % reduced NAD(P)H relative to the 0% and 100% values.

For screening purposes, the NADH fluorescence bioassay can be routinely used as it is the most sensitive and amenable to higher throughput. Using these assays it was demonstrated that mitochondria freshly isolated from PPG pre-treated (15 h) and washed (30 min) ZR-75-1 cells are unable to metabolize proline, although malate metabolism was not affected. Reversible PRODH inhibitor (5-oxo) effect was completely lost by washout (see, FIG. 6).

Designing and Synthesizing New PPG-Like PRODH Enzyme Inhibitors.

While the crystal structure of human PRODH has not been determined, a number of bacterial PRODH crystal structures with L-THFA bound in the catalytic site have been reported and therefore provide a scaffold to model human PRODH for the purpose of in silico evaluation of candidate PRODH inhibitors (Lee et al. (2003) *Nat. Struct. Biol.* 10: 109-114: Luo et al. (2012) *Biochemistry* 51: 10099-10108; Zhang et al. (2004) *Biochemistry,* 43: 12539-12648; Srivastava et al. (2010) *Proc. Natl. Acad. Sci. USA,* 107: 2878-2883). We have opted to leverage the stereospecificity, shape and size of the natural L-proline substrate as a basic scaffold for fitting within our human PRODH catalytic site model (and potentially interacting with endogenous FAD) to generate: i), more effective enantiomeric analogs of the reversible competitive inhibitor L-THFA, and ii), a set of mechanism-based suicide inhibitors based on PPG. Of note, while the FAD moiety is ubiquitously utilized by numerous other enzymes involved in redox reactions, FAD association with the TIM barrel structure adopted by PRODH occurs in only one other known instance, thus rendering PRODH's catalytic site a relatively unique molecular target (Zhang et al. (2004) *Biochemistry,* 43: 12539-12648).

As shown in FIG. 5A (top left panel), (S)-(+)-5-oxo-2-tetrahydrofurancarboxylic acid (5-oxo) was identified as a potentially new competitive inhibitor capable of greater H-bond affinity to the catalytic site's tyrosine (Y548) and arginine (R564, R563) residues; and subsequent testing of the S versus R isomers of 5-oxo in our mitochondrial PRODH bioassay clearly showed the stereospecificity of S-5-oxo. Based on the earlier report that N-propargylglycine (PPG) could act as a mechanism-based inhibitor of bacterial PRODH, and unable to commercially obtain this compound, we synthesized it as previously described (White et al. (2008) *Biochemistry* 47: 5573-5580). Comparing equimolar inhibitor concentrations (2 mM) in our PRODH bioassay, the mechanism-based PPG inhibitor shows significantly greater PRODH enzymatic inhibition over S-5-oxo, and based upon studies evaluating other propargylic (PPG-like) inhibitors against other flavoenzymes like MAO-B, we have modeled the post-reactive catalytic site covalent linkage of PPG to FAD's N5 as shown in FIG. 5A (bottom panel). As shown in FIG. 5B, we have synthesized members of a family of PPG-like structures, preserving their reactive propargylic mechanism but adding various hydrophobic substituents (e.g., R=Me, i-Pr, i-Bu), while also creating chiral α-carbon structures for stereospecificity. It is believed these new chemical entities have never been reported.

Our model initially predicted that the (S) enantiomer of PPG-Me might interfere with Y560 (FIG. 5B, bottom left, dash circle). However, following synthesis of this entity its lack of PRODH inhibiting activity using the mitochondrial assay described herein. In contrast, upon synthesis of (R/S)-PPG (FIG. 5B, middle) we have shown that it retains PRODH inhibiting activity in this same assay, demonstrating the model's prediction that hydrophobic group placement (e.g., methyl group) within the PPG like scaffold is important for pocket affinity and further identifying an optimal site for location of the hydrophobic group.

Given this site accommodation and in keeping with results, we expect that, in certain embodiments, the S-enantiomers of the PPG analogs will be more specific and better inhibitors than the comparable D-enantiomers however it is recognized that in certain embodiments, D-enantiomers can have useful activity. Without being bound to a particular theory, it is believed that the new PPG analogs described herein may be more effective than PPG as a PRODH inhibitor. T The various analogs described herein can readily be synthesized and can readily be assessed/validated for their enzyme inhibiting specificity and potency using the PRODH bioassay(s) described herein, and, optionally, running full inhibitor concentration ranges to determine Ki values. The analogs can also be further validated, as desired, by testing in various breast cancer cell lines models, e.g., as shown herein. to demonstrate the ability to inhibit cell viability/growth (Cell Titre Glo assay) and induce apoptosis (Western blotting for cleaved PARP and/or caspase, verified by FCM demonstration of sub-G0 cell populations and/or microscopic imaging of annexin-V staining), as performed previously (Wilson-Edell et al. (2014) *Breast Cancer Res. Treat.* 144: 287-298). FIGS. 2, 4, and 7 exemplify our use of these assays.

Confirm the Predicted FAD-Linked Suicide Mechanism.

Using a commercially available tagged PRODH expression vector (Origene) to transiently transfect MCF7 cells, cells treated with PPG for varying (3-12 h) intervals will be lysed and the tagged PRODH protein immunoprecipitated. Changes in the molecular weight of FAD due to its covalent linkage with PPG (FIG. 5A) can be determined from the immunoprecipitate by mass spectrometry (MS).

Aspect 2 Experimental Approach and Expectations.

We first evaluated the ability of L-tetrahydro-2-furoic acid (L-THFA), originally shown to be a competitive proline inhibitor against the bacterial PRODH orthologous protein PutA (Zhu et al. (2002) *Arch Biochem. Biophys.* 408:131-136), to synergistically interact with MI-63 against MCF7 and DU4475 cells. As shown in FIG. 2D, treatment of DU4475 breast cancer cells with L-THFA and MI-63 enhances both apoptosis (~4-fold over MI-63 treatment alone measured by c PARP production) and synergistically reduces viable cell growth in culture. With our later realization that PRODH inhibition might also produce a synthetic lethal interaction with GLS1 inhibition, we then tested both S-5-oxo and PPG in combination with CB-839 and demonstrated additive growth inhibition within 48 h and synergistic growth inhibition within 72 h against multiple breast cancer cell lines, while also showing lack of any growth inhibition against non-malignant MCF10A cells (FIG. 4). Given the combinatorial effectiveness of a low affinity PRODH inhibitor like L-THFA ($K_i$=0.3 mM), we expect that more effective PRODH enzymatic inhibitors from Aspect 1 will produce even greater synthetic lethal interactions with both MI-63 and CB-839. The enantiomeric PPG-like inhibitors of PRODH enzymatic activity from Aspect 1 will be compared with S-5-oxo and PPG for their capacity to promote synthetic lethal interactions with MI-63 and CB-839 in each of the four breast cancer cell lines by apoptosis and cell growth assays. To conclusively demonstrate synergistic interactions between inhibitors in our growth inhibition studies, we will test multiple drug concentrations over both 48 and 72 h under replicate conditions and calculate Combination Indices using Calcusyn (Biosoft, Cambridge, UK) software, as we have previously demonstrated (Wilson-Edell et al. (2014) *Breast Cancer Res. Treat.* 144: 287-298). To better understand the antitumor mechanism of PPG we will further explore our surprising observation that PPG promotes PRODH protein degradation within 24 h of exposure (FIG. 7), most likely mediated by the $UPR_{mt}$(38). Initial experiments will employ a battery of antibodies against FAD containing proteins to expand assessment of those impacted by PPG treatment as shown in FIG. 7. To confirm early (6-24 h) cell signaling from the mitochondrial matrix secondary to $UPR_{mt}$, phosphorylated (p)-JNK will be evaluated and compared to the p-PERK-mediated extra-mitochondrial ER protein unfolding ($UPR_{ER}$) response.

What is claimed is:

1. An analog of N-propargylglycine (PPG) that is capable of occupying the proline binding pocket of proline dehydrogenase (PRODH) and forming a covalent bond with PRODH or a flavin adenine dinucleotide (FAD) cofactor of PRODH, wherein the PPG analog comprises a compound with the formula:

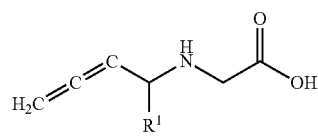

wherein $R^1$ is selected from the group consisting of H, $C_1$-$C_4$ alkyl, halogen, and $C_1$-$C_4$ haloalkyl.

2. The PPG analog of claim 1, wherein $R^1$ is selected from the group consisting of H, methyl, ethyl, isopropyl, isobutyl, Br, Cl, F, $CF_3$, and $CCl_3$.

3. The PPG analog of claim 1, wherein $R^1$ is H.

4. The PPG analog of claim 1, wherein $R^1$ is methyl.

5. The PPG analog of claim 1, wherein the PPG analog is a substantially pure S-enantiomer.

6. A pharmaceutical formulation comprising:
a PPG analog of claim 1; and
a drug that promotes p53 restoration; and/or
a drug that inhibits glutaminase (GLS).

7. The pharmaceutical formulation of claim 6, wherein $R^1$ is selected from the group consisting of H, methyl, ethyl, isopropyl, isobutyl, Br, Cl, F, $CF_3$, and $CCl_3$.

8. The pharmaceutical formulation of claim 7, wherein $R^1$ is H.

9. The pharmaceutical formulation of claim 7, wherein $R^1$ is methyl.

10. The pharmaceutical formulation of claim 6, wherein said PPG analog is a substantially pure S-enantiomer or a substantially pure R-enantiomer.

11. A pharmaceutical formulation comprising:
a PPG analog of claim 1; and
a pharmaceutically acceptable carrier.

12. The pharmaceutical formulation of claim 11, wherein $R^1$ is H.

13. The pharmaceutical formulation of claim 12, wherein $R^1$ is methyl.

14. The pharmaceutical formulation of claim 11, wherein said formulation is a unit dosage formulation.

15. The pharmaceutical formulation of claim 11, wherein said formulation is formulated for administration via a route selected from the group consisting of oral administration, transdermal administration, parenteral administration, aerosol administration, administration via inhalation, intravenous or intra-arterial administration, local administration via injection or cannula, and rectal administration.

16. The pharmaceutical formulation of claim 11, wherein said formulation is formulated for oral administration.

17. The pharmaceutical formulation of claim 11, wherein said formulation is formulated for administration into or near a solid tumor.

18. The pharmaceutical formulation claim 11, wherein said formulation is formulated for oral administration.

19. The PPG analog of claim 1, wherein the PPG analog is a substantially pure R-enantiomer.

* * * * *